US007176278B2

(12) United States Patent
Prior

(10) Patent No.: US 7,176,278 B2
(45) Date of Patent: Feb. 13, 2007

(54) MODIFIED TRANSFERRIN FUSION PROTEINS

(75) Inventor: Christopher P. Prior, King of Prussia, PA (US)

(73) Assignee: BioRexis Technology, Inc., Wilmington, DE (US)

( * ) Notice: Subject to any disclaimer, the term of this patent is extended or adjusted under 35 U.S.C. 154(b) by 291 days.

(21) Appl. No.: 10/378,094

(22) Filed: Mar. 4, 2003

(65) Prior Publication Data

US 2003/0221201 A1    Nov. 27, 2003

Related U.S. Application Data

(63) Continuation-in-part of application No. 10/231,494, filed on Aug. 30, 2002.

(60) Provisional application No. 60/406,977, filed on Aug. 30, 2002, provisional application No. 60/334,059, filed on Nov. 30, 2001, provisional application No. 60/315,745, filed on Aug. 30, 2001.

(51) Int. Cl.
*A61K 38/26* (2006.01)
*A61K 38/40* (2006.01)
*C07K 5/00* (2006.01)

(52) U.S. Cl. ............... 530/308; 530/394; 530/402; 424/192.1; 435/69.7

(58) Field of Classification Search ............ 530/394, 530/402, 378.3; 424/192.1; 435/69.7
See application file for complete search history.

(56) References Cited

U.S. PATENT DOCUMENTS

| | | | |
|---|---|---|---|
| 4,289,689 A | 9/1981 | Friesen et al. | |
| 4,738,931 A | 4/1988 | Sugano et al. | |
| 4,816,449 A | 3/1989 | Hahn | 514/17 |
| 5,026,651 A | 6/1991 | Bowman et al. | 435/320.1 |
| 5,091,513 A | 2/1992 | Huston et al. | 530/387.3 |
| 5,262,177 A | 11/1993 | Brown et al. | 435/35.1 |
| 5,442,043 A | 8/1995 | Fukuta et al. | 530/303 |
| 5,455,030 A | 10/1995 | Ladner et al. | 424/135.1 |
| 5,464,933 A | 11/1995 | Bolognesi et al. | |
| 5,518,889 A | 5/1996 | Ladner et al. | 435/7.93 |
| 5,571,691 A | 11/1996 | Conneely et al. | 435/69.1 |
| 5,571,896 A | 11/1996 | Conneely et al. | 530/400 |
| 5,656,272 A | 8/1997 | Le et al. | 424/133.1 |
| 5,672,683 A | 9/1997 | Friden et al. | |
| 5,817,789 A | 10/1998 | Heartlein et al. | |
| 5,876,969 A | 3/1999 | Fleer et al. | |
| 5,948,613 A | 9/1999 | Teng et al. | 435/6 |
| 5,977,307 A | 11/1999 | Friden et al. | |
| 5,986,067 A | 11/1999 | Funk et al. | |
| 6,027,921 A | 2/2000 | Heartlein et al. | 435/69.7 |
| 6,066,469 A | 5/2000 | Kruzel et al. | 435/69.1 |
| 6,069,193 A * | 5/2000 | Vargas et al. | 524/2 |
| 6,245,737 B1 | 6/2001 | Boyd et al. | |
| 6,262,026 B1 | 7/2001 | Heartlein et al. | 514/12 |
| 6,277,817 B1 | 8/2001 | Kruzel et al. | 514/8 |
| 6,348,568 B1 | 2/2002 | Barney et al. | |
| 6,380,362 B1 | 4/2002 | Watson et al. | 530/350 |
| 6,420,346 B1 | 7/2002 | Karin | 514/44 |
| 6,455,687 B1 | 9/2002 | Kruzel et al. | 536/23.5 |
| 6,458,924 B2 * | 10/2002 | Knudsen et al. | 530/324 |
| 2001/0025026 A1 | 9/2001 | Heartlein et al. | 514/12 |
| 2003/0199672 A1 | 10/2003 | Knudsen et al. | |
| 2003/0221201 A1 | 11/2003 | Prior et al. | 800/7 |
| 2003/0226155 A1 | 12/2003 | Sadeghi et al. | 800/7 |
| 2004/0023334 A1 | 2/2004 | Prior | 435/69.7 |

FOREIGN PATENT DOCUMENTS

| | | |
|---|---|---|
| EP | 0314317 | 5/1989 |
| EP | 0413662 | 2/1991 |
| EP | 0978565 A1 | 2/2000 |
| EP | 1408050 A1 | 4/2004 |
| WO | WO 95/02421 | 1/1995 |
| WO | WO 99/43707 A1 | 9/1999 |
| WO | WO 99/46283 A1 | 9/1999 |
| WO | WO 01/04156 A1 | 1/2001 |
| WO | WO 01/36643 A1 | 5/2001 |
| WO | 01/46254 | 6/2001 |
| WO | WO 01/79258 | 10/2001 |
| WO | WO 02/46227 | 6/2002 |
| WO | WO 02/46227 A2 | 6/2002 |

(Continued)

OTHER PUBLICATIONS

Xiao et al. (Mar. 2001) Biological activities of glucagon-like peptide-1 analogues in vitro and in vivo. Biochemistry, vol. 40, No. 9, pp. 2860-2869.*

(Continued)

*Primary Examiner*—Jon Weber
*Assistant Examiner*—Samuel W. Liu
(74) *Attorney, Agent, or Firm*—Cooley Godward LLP.

(57) ABSTRACT

The present invention discloses fusion proteins comprising transferrin, lactoferrin or melanotransferrin fused to glucagon-like peptide 1 (GLP-1). In one embodiment of the invention, the fusion protein displays increased serum half-life as compared to a GLP-1 peptide in an unfused state. The invention includes a pharmaceutical composition comprising the GLP-1 fusion protein of the invention and a carrier. The fusion protein of the invention can be administered to a subject for treatment of diseases or conditions treatable by GLP-1, including, but not limited to, diabetes, obesity, congestive heart failure and inflammatory bowel syndrome.

47 Claims, 6 Drawing Sheets

FOREIGN PATENT DOCUMENTS

| | | |
|---|---|---|
| WO | WO 03/016349 A1 | 2/2003 |
| WO | WO 03/020746 | 3/2003 |
| WO | WO 03/082898 | 10/2003 |
| WO | WO 2004/019872 | 3/2004 |
| WO | WO 2004/020404 | 3/2004 |
| WO | WO 2004/020405 | 3/2004 |
| WO | WO 2004/020454 | 3/2004 |
| WO | WO 2004/020588 | 3/2004 |
| WO | WO 2004/078777 | 9/2004 |

OTHER PUBLICATIONS

Xia et al. (2000) Hypoglycemic effect of insulin-transferrin conjugate in streptozotocin-induced diabetic rats. J. Pharmacol. Exp. Ther. vol. 295, No. 2, pp. 594-600.*

Adrian et al. "Human transferrin: Expression and iron modulation of chimeric genes intransgenic mice" J. Biol. Chem. 265(22): 13344, 1990.

Gallop et al. "Applications of combinatorial technologies to drug discovery. 1. Background and peptide combinatorial libraries" J. Med. Chem. 37(9): 1234, 1994.

Gallwitz B et al. (1996) "GLP-1/GIP chimeric peptides define the structural requirements for specific ligand-receptor interaction of GLP-1" Regul Pept. 63(1):17-22, 1996.

MacGillivray et al. "The primary structure of human serum transferrin" J. Biol. Chem. 258(6): 3543, 1983.

Salmon et al. "Production of human lactoferrin in transgenic tobacco plants" Protein Exp. Purif. 13: 127, 1998.

Ward et al. "A system for production of commercial quantities of human lactoferrin: a broad spectrum natural antibiotic" Biotechnology 13:498, 1995.

Batra et al., "Single Chain Immunotoxins Directed at the Human Transferrin Receptor Containing Pseudomonas Exotoxin A or Diphtheria Toxin: Anti-TFR(Fv)-PE40 and DT 388-Anti-TFR(Fv)", Mol. Cell. Biol., 11:2200-2205, 1991.

Brinkman et al., "A recombinant immunotoxiin that is active on prostate cancer cells and that is composed of the Fv region of monoclonal antibody PR1 and a truncated form of *Pseudomonas* exotoxin", Prc. Natl. Sci. Acad. Sci. USA, vol. 90, pp. 547-551, Jan. 1993.

Chaudhary et al., "A recombinant immunotoxin consisting of two antibody variable domains fused to *Pseudomonas* exotoxin", Nature, 339:394-397, 1989.

Database A GENESEQ (Compugen LTD), Accession No. AAR66492, (Jacobs et al), Nov. 25, 1994.

Hoo et al., "Characterization of a single-chain T-cell receptor expressed in *Escherichia coli*", Proc. Nat. Acad. Sci. USA, 89:4759-4763, 1993.

Huston et al., "Protein engineering of antibody binding sites: Recovery of specific activity in an anti-digoxin single-chain Fv analogue produced in *Escherichia coli*", Proc. Nat. Acad. Sci. USA; 85 (16):5879-5883, 1988.

Liang et al., "Production and Characterization of Monoclonal Antibodies Against Recombinant Human Tumor Necrosis Factor/ Cachetin", Biochem Biophys Res. Comm. 137:847-854, 1986.

Nicholls, "Characterization of Single-chain Antibody (sFv)-Toxin Fusion Proteins Produced in Vitro in Rabbit Reticulocyte Lysate", J. Biological Chem., 268: 5302-5308, 1993.

Prince et al., "Efficient Endocytosis of the Cystic Fibrosis Transmembrane Conductance Regulator Requires a Tyrosine-Based signal, " J Biol Chem 274(6):3602-3609, 1999.

Sheridan et al., "Solid-phase Synthesis and Cyclization of a Large Branched Peptide from IgG Fc with Affinity for FcRI", J. Pept. Sci, 1999, 5(12):555-562.

Traunecker et al., "Bispecific single chain molecules (Janusins) target cytotoxic lymphocytes on HIV infected cells", EMBO J., 10(12):3655-3659, 1991.

Arndt, T., "Carbohydrate-Deficient Transferrin as a Marker of Chronic Alcohol Abuse: A Critical Review of Preanalysis, Analysis, and Interpretation," *Clinical Chemistry* 47:13-27, 2001.

Ali et al., "Transferrin Trojan Horses as a Rational Approach for the Biological Delivery of Therapeutic Peptide Domains," *J Biol Chem* 274(34):24066-24073, 1999.

Newton et al., "Antitransferrin Receptor antibody-RNase Fusion Protein Expressed in the Mammary Gland of transgenic mice," *J Immunological Methods* 231:159-167, 1999.

Park et al., "Production and characterization of Fusion Proteins Containing Transferrin and Nerve Growth Factor," *J Drug Targeting* 6(1):53-64, 1998.

Prince et al., "Efficient Endocytosis of the Cystic Fibrosis Transmembrane Conductance Regulator Requires a Tyrosine-Based signal," *J Biol Chem* 274(6):3602-3609, 1999.

Regoeczi et al., "Rat Aglycotransferrin and Human Monoglycotransferrin: Production and Metabolic Properties," *Archives of Biochemistry and Biophysics* 268(2): 637-642, 1989.

Shin et al., "Transferrin-Antibody Fusion Proteins are Effective in Brain Targeting," *Proc Natl Acad Sci USA* 92:2820-2824, 1995.

Bradley et al., "Identification of the cellular receptor for anthrax toxin," *Nature* 414:225-229, 2001.

Bradley et al., "Anthrax toxin receptor proteins," *Biochemical Pharmacology* 65:309-314, 2003.

Cha et al., "Receptor-based antidote for diphtheria," *Infection and Immunity* 70(5):2344-2350, 2002.

Drucker, "Biological actions and therapeutic potential of the glucagon-like peptides," *Gastroenterology* 122:531-544, 2002.

Kozaki et al., "Characterization of *Clostridium botulinum* type B neurotoxin associated with infant botulism in Japan," *Infection and Immunity* 66(10):4811-4816, 1998.

Li et al., "Isolation of synaptotagmin as a receptor for types A and E botulinum neurotoxin and analysis of their comparative binding using a new microtiter plate assay," *J Natural Toxins* 7(3):215-226, 1998.

Nishiki et al., "Identification of protein receptor for *Clostridium botulinum* type B neurotoxin in rat brain synaptosomes," *J Biol Chem* 269(14):10498-10503, 1994.

Wrighton et al., "Small peptides as potent mimetics of the protein hormone erythropoietin," *Science* 273(5274):458-464, 1996.

Xia et al., "Hypoglycemic effect of insulin-transferrin conjugate in streptozocin-induced diabetic rats," *J Pharmacology and Environmental Therapeutics* 295(2);594-600, 2000.

Hosoi et al., "Structural Characterization of Fibroblast Human Interferon-$\beta_1$," *Journal of Interferon Research* 8:375-384, 1988.

Johnson et al., "Identification of a 13 Amino Acid Peptide Mimetic of Erythropoietin and Description of Amino Acids Critical for the Mimetic Activity of EMP1," *Biochemistry* 37:3699-3710, 1998.

Naglich et al., "Expression Cloning of a Diphtheria Toxin Receptor: Identity with a Heparin-Binding EGF-like Growth Factor Precursor," *Cell* 69:1051-1061, 1993.

Aldred et al., "Synthesis of rat transferrin in *Escherichia coli* containing a recombinant bacteriophage," *Biochem. Biophys. Res. Commun.* 122:960-965, 1984.

Ali et al., "High-yield production of functionally active human serum transferrin using a baculovirus expression system, and its structural characterization," *Biochem. J.* 319:191-195, 1996.

Batra et al., "Recombinant anti-erbB2 immunotoxins containing *Pseudomonas* exotoxin," *Proc. Nat. Acad. Sci. USA* 89:5867-5871, Jul. 1992.

Deacon et al., "Dipeptidyl peptidase IV resistant analogues of glucagon-like peptide-1 which have extended metabolic stability and improved biological activity," *Diabetologia* 41:271-278, 1998.

Hoefkens et al., "influence of transferrin glycans on receptor binding and iron-donation," *Glycoconjugate J.* 14:289-295, 1997.

O'Harte et al., "$NH_2$-Terminally Modified Gastric Inhibitory Polypeptide Exhibits Amino-Peptidase Resistance and Enhanced Antihyperglycemic Activity," *Diabetes* 48:758-765, 1999.

Pedersen et al., "Removal of N-terminal Polyhjistidine Tags from recombinant Proteins Using Engineered Aminopeptidases," *Protein Express. Purif.* 15:389-400, 1999.

Siegel et al., "Biological activity of GLP-1-analogues with N-terminal modifications," *Regulatory Peptides* 79:93-102, 1999.

Zhao et al., "Inhibition of Dipeptidyl Peptidase IV (DPP IV) by 2-(2-Amino-1-fluoro-propylidene)-cyclopentanecarbonitrile, a Fluoroolefin Containing Peptidomimetic," *Bioorg. Med. Chem.* 11:207-215, 2003.

Vogt, "Communication pursuant to Article 96(2) EPC," from EP 02757486.2, 7 pages, European Patent Office, Munich, Germany (mailed Jun. 1, 2006).

Sommer, B., "Supplementary Partial European Search Report," from EP 03749159.4, 4 pages, European Patent Office, Munich, Germany (mailed May 30, 2006).

Parise, F., et al., "Construction and *in Vitro* Functional Evaluation of a Low-Density Lipoprotein Receptor/Transferrin Fusion Protein as a Therapeutic Tool for Familial Hypercholesterolemia," *Human Gene Therapy* 10:1219-1228 (1999).

Adelhorst et al., "Structure-Activity Studies of Glucagon-like Peptide-1," *J. Biol. Chem.* 269(9):6275-6278 (1994).

Kawai et al., "The Biological Effects of Glucagon-Like Peptide-1 (GLP-1) and its Structure-Activity Relationship," *Biomed. Res.* 9(Suppl. 3):213-217 (1988).

Knudsen et al., "Potent Derivatives of Glucagon-like Peptide-1 with Pharmacokinetic Properties Suitable for Once Daily Administration," *J. Med. Chem.* 43:1664-1669 (2000).

Mojsov, "Structural requirements for biological activity of glucagon-like peptide-1," *Int'l. J. Pept. Prot. Res.* 40(3/4):333-343 (1992).

Mossier, "Supplementary Partial European Search Report," from EP 04717362.0, 12 pages, European Patent Office, Munich, Germany (mailed Aug. 8, 2006).

Ohneda et al., "The Structure-Function Relationship of GLP-1 Related Peptides in the Endocrine Function of Canine Pancreas," *Tohoku J. Exp. Med.* 165:209-221 (1991).

Kieffer et al., "Degradation of Glucose-Dependent Insulinotropic Polypeptide and Truncated Glucagon-Like Peptide 1 *in Vitro* and *in Vivo* by Dipeptidyl Peptidase IV," *Endocrinology* 136(8):3585-3596 (1995).

Wagner et al., "Delivery of drugs, proteins, and genes into cells using trasferrin as a ligand for receptor-medicated endocytosis", Advance Drug Delivery Reviews 14(1994) pp. 113-135.

Partial European Search Report dated Apr. 18, 2006 (EP Application No. 03 79 1808) 6 pgs.

* cited by examiner

FIG. 1
Alignment of N and C domains of Transferrin to show Iron Binding residues.

```
N  --VPD---KTVRWCAVSEHEATKCQSFRDHMKSVIPSDGPSVACVKKASYLDCIRAIAAN
C  PEATDECKPVKWCALSHHERLKCDEWS------VNSVG-KIECVSAETTEDCIAKIMNG

*                                    *
N  EADAVTLDAGLVYDAYLAPNNLKPVVAEFYG----SKEDPQTFYYAVAVVKK-DSGFQMN
C  EADAMSLDGGFVYIAGKCG--LVPVLAENYNKSDNCEDTPEAGYFAVAVVKKSASDLTWD

‡  ‡‡‡
N  QLRGKKSCHTGLGRSAGWNIPIGLLYCDLPEPRKPLEKAVANFFSGSCAPCADGTDFPQL
C  NLKGKKSCHTAVGRTAGWNIPMGLLYNKINHCR--FD----EFFSEGCAPGSKKD--SSL

*
N  CQLCPGCG---CSTLN--QMFGYSGAFKCLKDGAGDVAFVKHSTIFEN--------LANK
C  CKLCMGSGLNLCEPNNKEGYYGYTGAFRCLVE-KGDVAFVKHQTVPQNTGGKNPDPWAKN

*
N  ADRDQYELLCLDNTRKPVDEYKDCHLAQVPSHTVVARSMGGKEDLIWELLNQAQEHFGK-
C  LNEKDYELLCLDGTRKPVEEYANCHLARAPNHAVVTR--KDKEACVHKILRQQQHLFGSN

†
N  --DKSKEFQLFSSPHGKDLLFKDSAHGFLKVPPRMDAKMYLGYEYVTAIRNLREGTC---
C  VTDCSGNFCLFRSET-KDLLFRDDTVCLAKLHDRNTYEKYLGEEYVKAVGNLRKCSTSSL

N  ---------
C  LEACTFRRP
```

☐: similarity
▨: identity
Amino acid residues involved in iron binding (*)

| N domain | C domain |
|---|---|
| Asp 63 | Asp 392 |
| Tyr 95 | Tyr 426 |
| Tyr 188 | Tyr 514 |
| His 249 | His 585 |

Indirectly involved in iron binding (†)

| | |
|---|---|
| Lys 296 | Arg 632 |

Binding of carbonate ion (‡)

| | |
|---|---|
| Thr 120 | Thr 452 |
| Arg 124 | Arg 456 |
| Ala 126 | Ala 458 |
| Gly 127 | Gly 459 |

FIG. 2A-1
Alignment of Tf Sequences

FIG. 2A-2
Alignment of Tf Sequences

PEPTIDE DELIVERY USING RECOMBINANT TRANSFERRIN

MODIFIED TRANSFERRIN FUSION PROTEINS

RELATED APPLICATIONS

This application is a Continuation-In-Part Application of Ser. No. 10/231,494, filed Aug. 30, 2002, which claims the benefit of U.S. Provisional Application 60/315,745, filed Aug. 30, 2001 and U.S. Provisional Application 60/334,059, filed Nov. 30, 2001, all of which are herein incorporated by reference in their entirety.

FIELD OF THE INVENTION

The present invention relates to therapeutic proteins or peptides and soluble toxin receptor fragments with extended serum stability or serum half-life fused to or inserted in a transferrin molecule modified to reduce or inhibit glycosylation, iron binding and/or transferrin receptor binding. Specifically, the present invention includes IFN-β, GLP-1, EMP1, and T-20 fused to or inserted in a transferrin molecule or a modified transferrin molecule. The present invention also includes an anti-toxin fusion protein comprising a fragment of synaptotagmin 1 fused to or inserted in a transferrin molecule or a modified transferrin molecule.

BACKGROUND OF THE INVENTION

Therapeutic proteins or peptides in their native state or when recombinantly produced are typically labile molecules exhibiting short periods of serum stability or short serum half-lives. In addition, these molecules are often extremely labile when formulated, particularly when formulated in aqueous solutions for diagnostic and therapeutic purposes.

Few practical solutions exist to extend or promote the stability in vivo or in vitro of proteinaceous therapeutic molecules. Polyethylene glycol (PEG) is a substance that can attach to a protein, resulting in longer-acting, sustained activity of the protein. If the activity of a protein is prolonged by the attachment to PEG, the frequency that the protein needs to be administered is decreased. PEG attachment, however, often decreases or destroys the protein's therapeutic activity.

Therapeutic proteins or peptides have also been stabilized by fusion to a heterologous protein capable of extending the serum half-life of the therapeutic protein. For instance, therapeutic proteins fused to albumin and antibody fragments may exhibit extended serum half-live when compared to the therapeutic protein in the unfused state. See U.S. Pat. Nos. 5,876,969 and 5,766,88.

Another serum protein, glycosylated human transferrin (Tf) has also been used to make fusions with therapeutic proteins to target delivery intracellularly or to carry heterologous agents across the blood-brain barrier. These fusion proteins comprising glycosylated human Tf have been used to target nerve growth factor (NGF) or ciliary neurotrophic factor (CNTF) across the blood-brain barrier by fusing full-length Tf to the either agent. See U.S. Pat. Nos. 5,672,683 and 5977,307. In these fusion proteins, the Tf portion of the molecule is glycosylated and binds to two atoms of iron, which is required for Tf binding to its receptor on a cell and, according to the inventors of these patents, to target delivery of the NGF or CNTF moiety across the blood-brain barrier. Transferrin fusion proteins have also been produced by inserting an HIV-1 protease sequence into surface exposed loops of glycosylated transferrin to investigate the ability to produce another form of Tf fusion for targeted delivery to the inside of a cell via the Tf receptor (Ali et al. (1999) *J. Biol. Chem.* 274(34):24066–24073).

Serum transferrin (Tf) is a monomeric glycoprotein with a molecular weight of 80,000 daltons that binds iron in the circulation and transports it to various tissues via the transferrin receptor (TfR) (Aisen et al. (1980) *Ann. Rev. Biochem.* 49: 357–393; MacGillivray et al. (1981) *J. Biol. Chem.* 258: 3543–3553, U.S. Pat. No. 5,026,651). Tf is one of the most common serum molecules, comprising up to about 5–10% of total serum proteins. Carbohydrate deficient transferrin occurs in elevated levels in the blood of alcoholics and exhibits a longer half life (approximately 14–17 days) than that of glycosylated transferrin (approximately 7–10 days). See van Eijk et al. (1983) *Clin. Chim. Acta* 132:167–171, Stibler (1991) *Clin. Chem.* 37:2029–2037 (1991), Arndt (2001) *Clin. Chem.* 47(1):13–27 and Stibler et al. in "Carbohydrate-deficient consumption", Advances in the Biosciences, (Ed Nordmann et al.), Pergamon, 1988, Vol. 71, pages 353–357).

The structure of Tf has been well characterized and the mechanism of receptor binding, iron binding and release and carbonate ion binding have been elucidated (U.S. Pat. Nos. 5,026,651, 5,986,067 and MacGillivray et al. (1983) *J. Biol. Chem.* 258(6):3543–3546).

Transferrin and antibodies that bind the transferrin receptor have also been used to deliver or carry toxic agents to tumor cells as cancer therapy (Baselga and Mendelsohn, 1994), and transferrin has been used as a non-viral gene therapy vector to vehicle to deliver DNA to cells (Frank et al., 1994; Wagner et al., 1992). The ability to deliver proteins to the central nervous system (CNS) using the transferrin receptor as the entry point has been demonstrated with several proteins and peptides including CD4 (Walus et al., 1996), brain derived neurotrophic factor (Pardridge et al., 1994), glial derived neurotrophic factor (Albeck et al.), a vasointestinal peptide analogue (Bickel et al., 1993), a betaamyloid peptide (Saito et al., 1995), and an antisense oligonucleotide (Pardridge et al., 1995).

Transferrin fusion proteins have not, however, been modified or engineered to extend the serum half-life of a therapeutic protein or peptide or to increase bioavailability by reducing or inhibiting glycosylation of the Tf moiety or to reduce or prevent iron and/or Tf receptor binding.

SUMMARY OF THE INVENTION

As described in more detail below, the present invention includes modified Tf fusion proteins comprising at least one therapeutic protein, polypeptide or peptide entity, wherein the Tf portion is engineered to extend the serum half-life or bioavailability of the molecule. The invention also includes pharmaceutical formulations and compositions comprising the fusion proteins, methods of extending the serum stability, serum half-life and bioavailability of a therapeutic protein by fusion to modified transferrin, nucleic acid molecules encoding the modified Tf fusion proteins, and the like. Another aspect of the present invention relates to methods of treating a patient with a modified Tf fusion protein.

Preferably, the modified Tf fusion proteins comprise a human transferrin Tf moiety that has been modified to reduce or prevent glycosylation and/or iron and receptor binding.

The present invention provides fusion proteins comprising therapeutic proteins fused to or inserted into the transferrin or modified transferrin molecules. Preferably, the therapeutic proteins of the present invention include β-interferon (β-IFN), glucagon-like peptide (GLP-1), EPO (erythropoietin) mimetic peptide (EMP1), and T-20.

The present invention also provides fusion proteins comprising a soluble toxin receptor fragment that bins a toxin fused to or inserted into the transferrin or modified transferrin molecules. The soluble toxin receptor may be synaptotagmin 1 and the soluble fragment is amino acids 1–53.

BRIEF DESCRIPTION OF THE DRAWINGS

FIG. 1 shows an alignment of the N and C Domains of Human (Hu) transferrin (Tf) with similarities and identities highlighted. The sequence of the N domain is SEQ ID NO.: 68, and the sequence of the C Domain is SEQ ID NO.: 69.

Figure 2A-1:
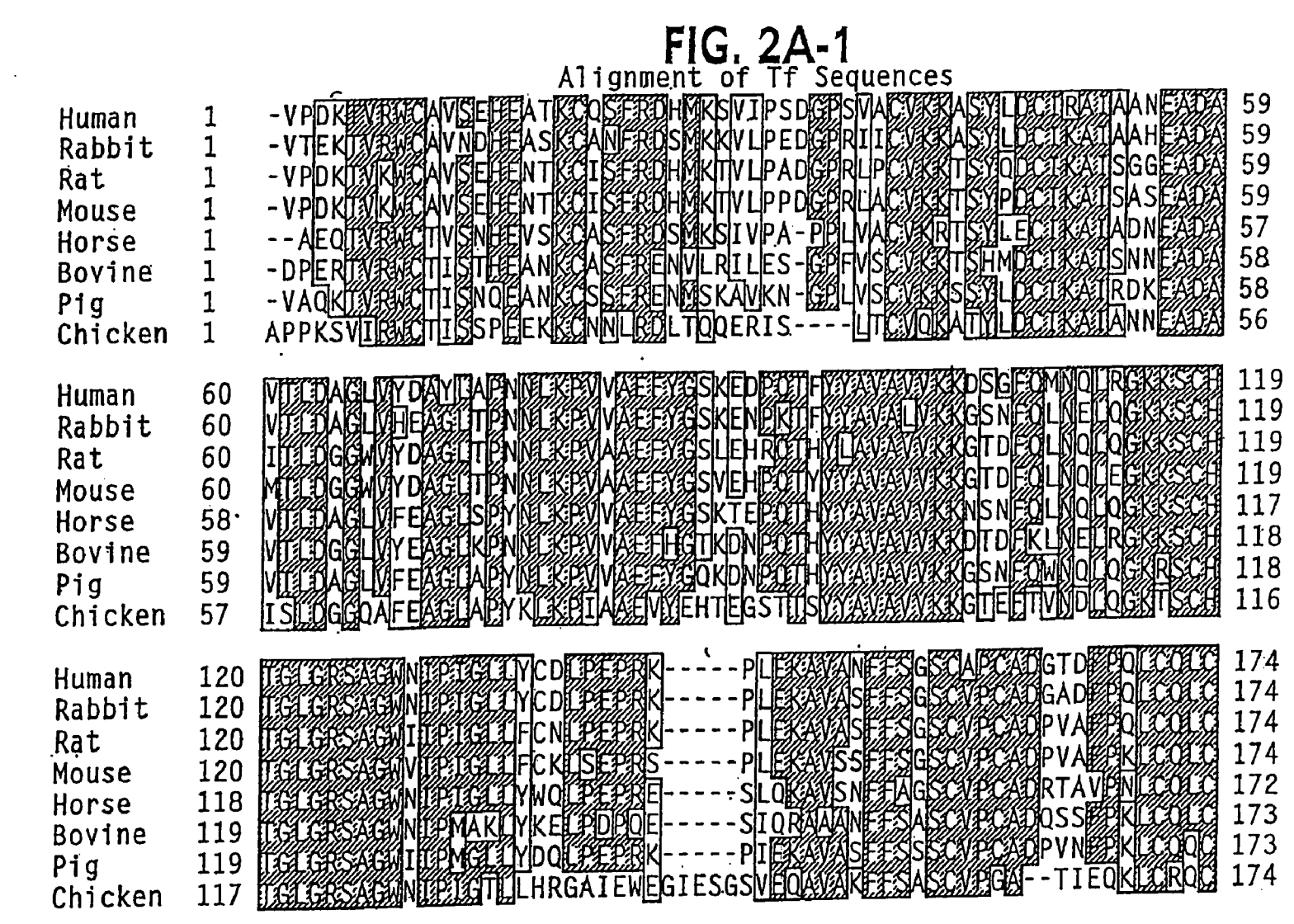
Figure 2A-2:
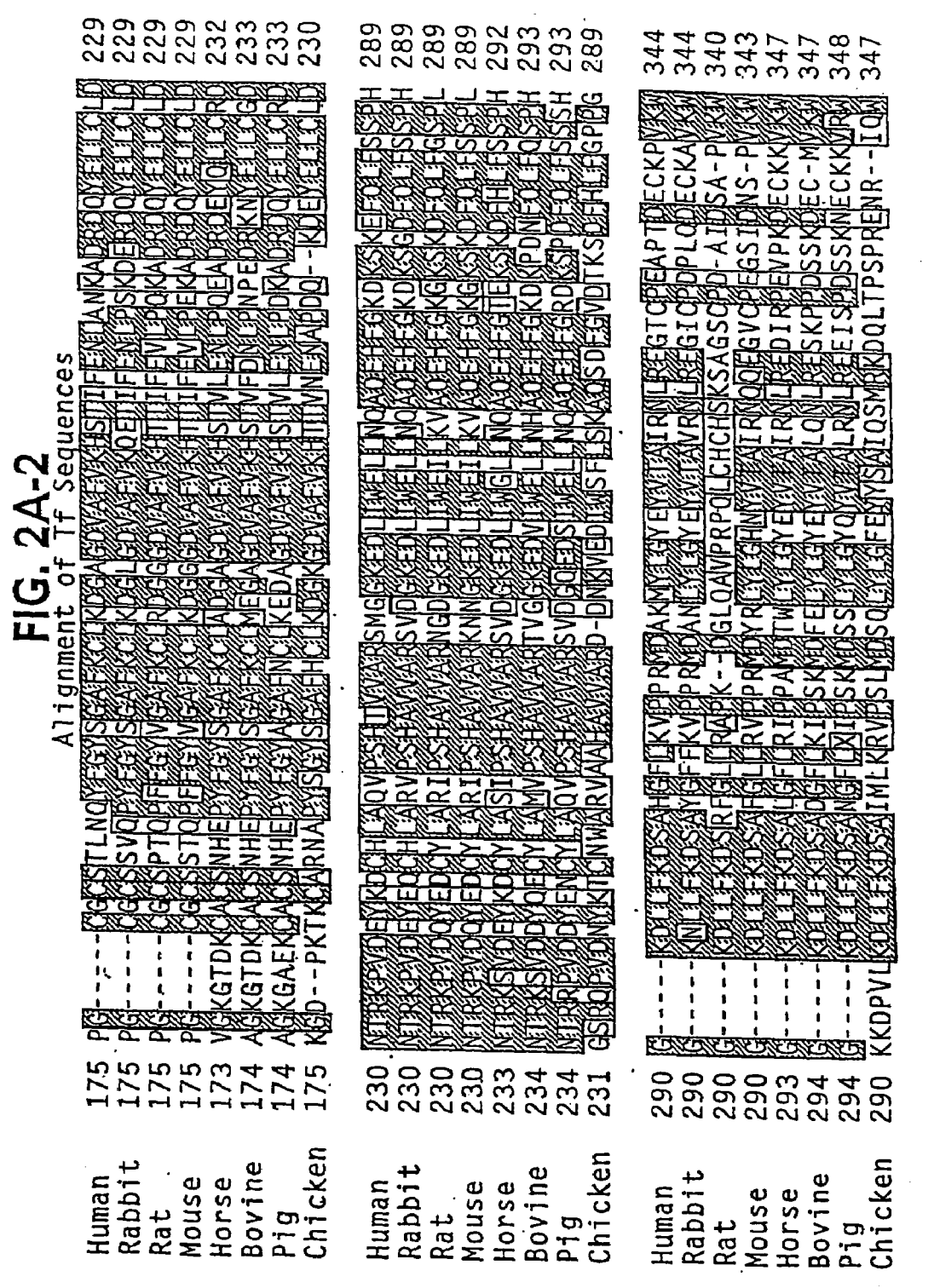
Figure 2B-1:
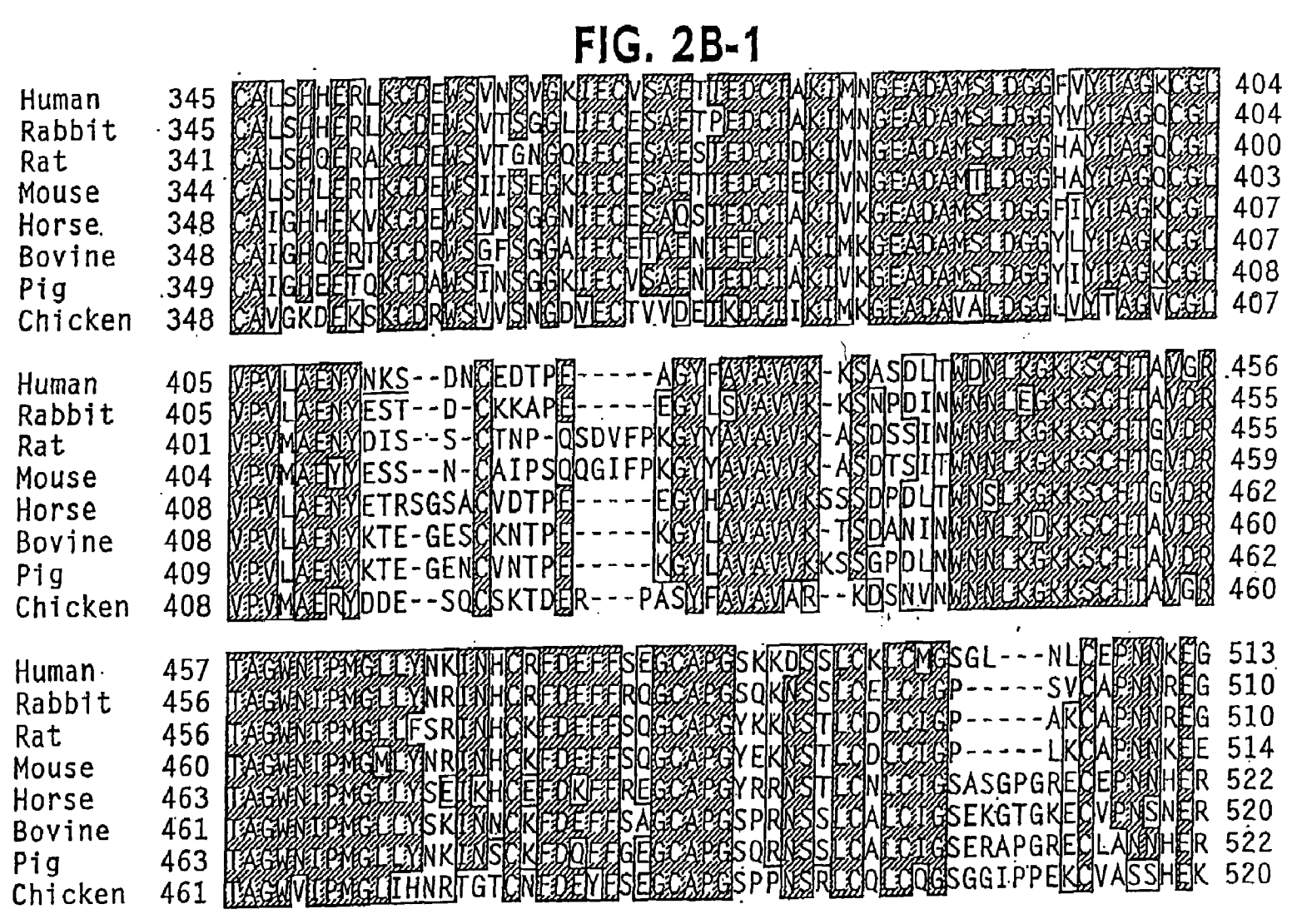
Figure 2B-2:
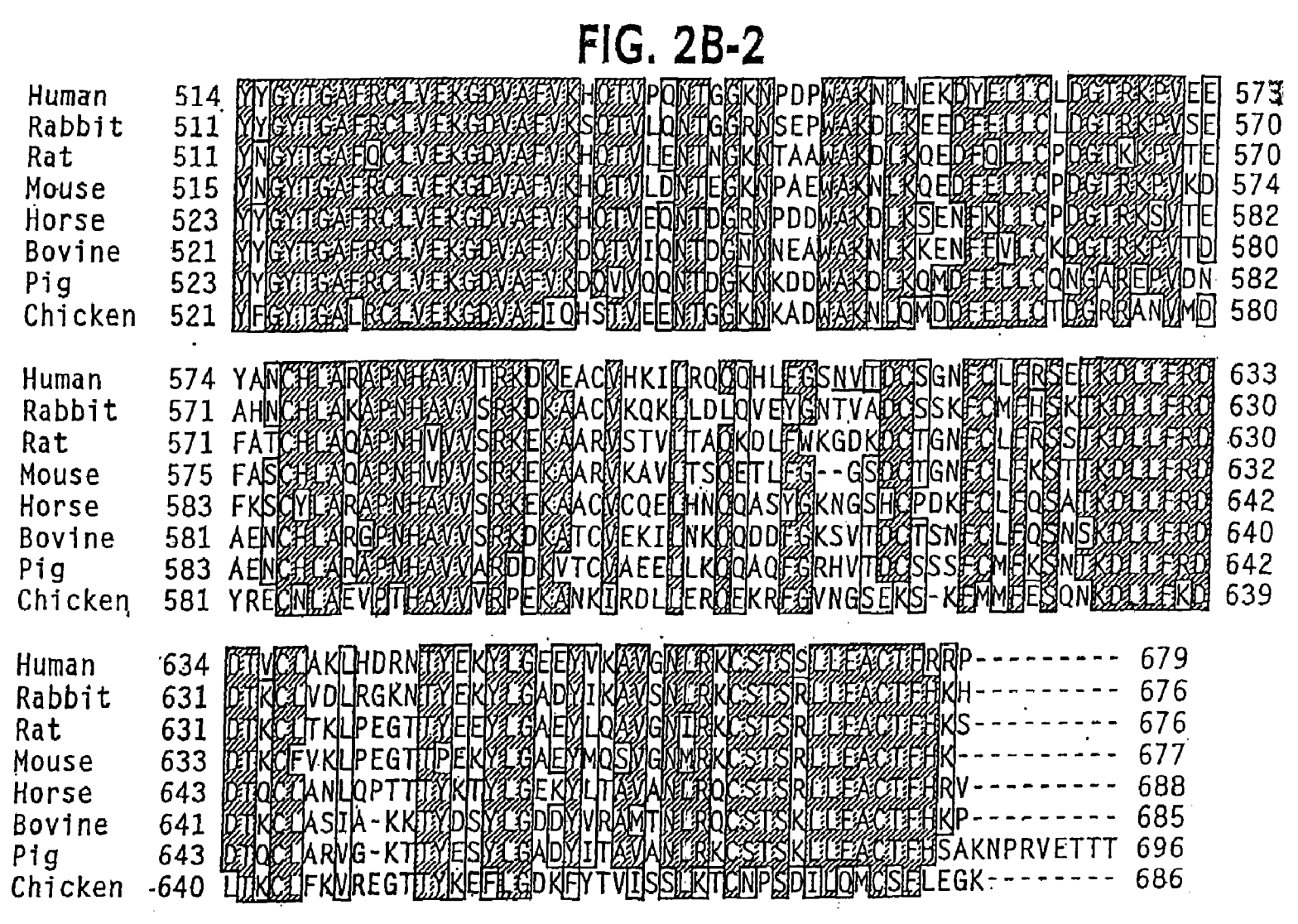

FIGS. 2A–2B show an alignment of transferin sequences from different species. Light shading: Similarity; Dark shading: Identity. The human sequence is SEQ ID NO.: 3; the rabbit sequence is SEQ ID NO.: 70, the rat sequence is SEQ ID NO.: 71, the mouse sequence is SEQ ID NO.: 72, the horse sequence is SEQ ID NO.: 73, the bovine sequence is SEQ ID NO.: 74, the pig sequence is SEQ ID NO.: 75, and the chicken sequence is SEQ ID NO.: 76.

DETAILED DESCRIPTION

General Description

Figure 3:
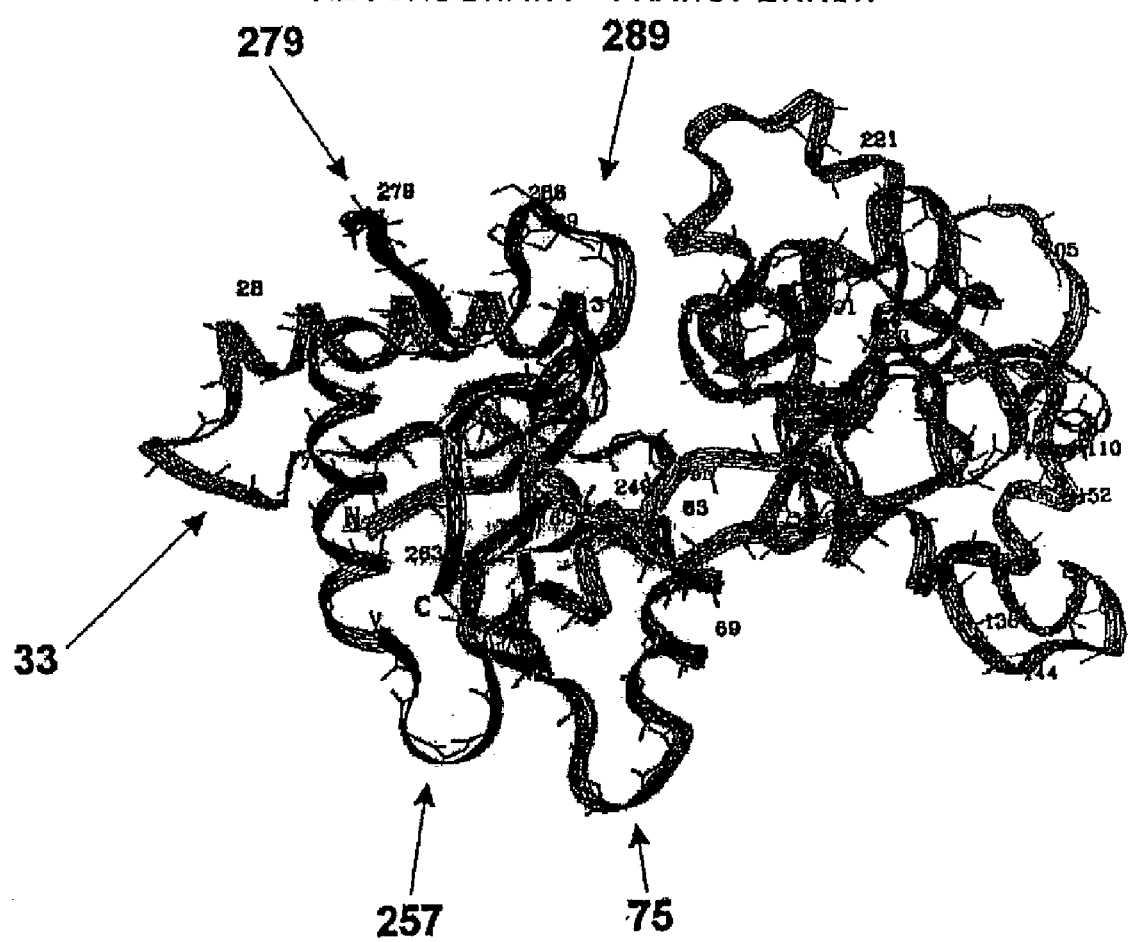
FIG. 3 shows the location of a number of Tf surface exposed insertion sites for therapeutic proteins, polypeptides or peptides.

The present invention is based in part on the finding by the inventors that therapeutic proteins can be stabilized to extend their serum half-life and/or activity in vivo by genetically fusing the therapeutic proteins to transferrin, modified transferrin, or a portion of transferrin or modified transferrin sufficient to extend the half-life of the therapeutic protein in serum. The modified transferrin fusion proteins include a transferrin protein or domain covalently linked to a therapeutic protein or peptide, wherein the transferrin portion is modified to contain one or more amino acid substitutions, insertions or deletions compared to a wild-type transferrin sequence. In one embodiment, Tf fusion proteins are engineered to reduce or prevent glycosylation within the Tf or a Tf domain. In other embodiments, the Tf protein or Tf domain(s) is modified to exhibit reduced or no binding to iron or carbonate ion, or to have a reduced affinity or not bind to a Tf receptor (TfR).

The therapeutic proteins contemplated by the present invention include, but are not limited to polypeptides, antibodies, peptides, or fragments or variants thereof. Preferably, the therapeutic proteins of the present invention include β-interferon, glucagon-like peptide-1 (GLP-1), EPO mimetic peptide (EMP1), and T-20.

The present invention also contemplates anti-toxin fusion proteins comprising a soluble toxin receptor fragment fused or inserted into transferrin or modified transferrin. Preferably, the soluble toxin receptor fragment binds a specific toxin. In one embodiment, the soluble toxin receptor fragment is amino acids 1–53 (SEQ ID NO: 4) of synaptotagmin 1.

The present invention therefore includes transferrin fusion proteins, therapeutic compositions comprising the fusion proteins, and methods of treating, preventing, or ameliorating diseases or disorders by administering the fusion proteins. A transferrin fusion protein of the invention includes at least a fragment or variant of a therapeutic protein and at least a fragment or variant of modified transferrin, which are associated with one another, preferably by genetic fusion (i.e., the transferrin fusion protein is generated by translation of a nucleic acid in which a polynucleotide encoding all or a portion of a therapeutic protein is joined in-frame with a polynucleotide encoding all or a portion of modified transferrin) or chemical conjugation to one another. The therapeutic protein and transferrin protein, once part of the transferrin fusion protein, may be referred to as a "portion", "region" or "moiety" of the transferrin fusion protein (e.g., a "therapeutic protein portion" or a "transferrin protein portion").

In one embodiment, the invention provides a transferrin fusion protein comprising, or alternatively consisting of, a therapeutic protein and a modified serum transferrin protein. In other embodiments, the invention provides a transferrin fusion protein comprising, or alternatively consisting of, a biologically active and/or therapeutically active fragment of a therapeutic protein and a modified transferrin protein. In other embodiments, the invention provides a transferrin fusion protein comprising, or alternatively consisting of, a biologically active and/or therapeutically active variant of a therapeutic protein and modified transferrin protein. In further embodiments, the invention provides a transferrin fusion protein comprising a therapeutic protein, and a biologically active and/or therapeutically active fragment of modified transferrin. In another embodiment, the therapeutic protein portion of the transferrin fusion protein is the active form of the therapeutic protein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Definitions

As used herein, the term "biological activity" refers to a function or set of activities performed by a therapeutic molecule, protein or peptide in a biological context (i.e., in an organism or an in vitro facsimile thereof). Biological activities may include but are not limited to the functions of the therapeutic molecule portion of the claimed fusion proteins, such as, but not limited to, the induction of extracellular matrix secretion from responsive cell lines, the induction of hormone secretion, the induction of chemotaxis, the induction of mitogenesis, the induction of differentiation, or the inhibition of cell division of responsive cells. A fusion protein or peptide of the invention is considered to be biologically active if it exhibits one or more biological activities of its therapeutic protein's native counterpart.

As used herein, an "amino acid corresponding to" or an "equivalent amino acid" in a transferrin sequence is identified by alignment to maximize the identity or similarity between a first transferrin sequence and at least a second transferrin sequence. The number used to identify an equivalent amino acid in a second transferrin sequence is based on the number used to identify the corresponding amino acid in the first transferrin sequence. In certain cases, these phrases may be used to describe the amino acid residues in human transferrin compared to certain residues in rabbit serum transferrin.

As used herein, the terms "fragment of a Tf protein" or "Tf protein," or "portion of a Tf protein" refer to an amino acid sequence comprising at least about 5%, 10%, 20%, 30%, 40%, 50%, 60%, 70%, 80%, 90%, 95%, 96%, 97%, 98%, 99% or 100% of a naturally occurring Tf protein or mutant thereof.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, a "heterologous polynucleotide" or a "heterologous nucleic acid" or a "heterologous gene" or a "heterologous sequence" or an "exogenous DNA segment" refers to a polynucleotide, nucleic acid or DNA segment that originates from a source foreign to the particular host cell, or, if from the same source, is modified from its original form. A heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. As an example, a signal sequence native to a yeast cell but attached to a human Tf sequence is heterologous.

As used herein, an "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

As used herein, two or more DNA coding sequences are said to be "joined" or "fused" when, as a result of in-frame fusions between the DNA coding sequences, the DNA coding sequences are translated into a polypeptide fusion. The term "fusion" in reference to Tf fusions includes, but is not limited to, attachment of at least one therapeutic protein, polypeptide or peptide to the N-terminal end of Tf, attachment to the C-terminal end of Tf, and/or insertion between any two amino acids within Tf.

As used herein, the term "modified transferrin" as used herein refers to a transferrin molecule that exhibits at least one modification of its amino acid sequence, compared to wildtype transferrin.

As used herein, the term "modified transferrin fusion protein" as used herein refers to a protein formed by the fusion of at least one molecule of modified transferrin (or a fragment or variant thereof) to at least one molecule of a therapeutic protein (or fragment or variant thereof), preferably an antibody variable region.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605–2608; Cassol et al. (1992); Rossolini et al. (1994) Mol. Cell. Probes 8:91–98). The term nucleic acid is used interchangeably with gene, cDNA, and mRNA encoded by a gene.

As used herein, a DNA segment is referred to as "operably linked" when it is placed into a functional relationship with another DNA segment. For example, DNA for a signal sequence is operably linked to DNA encoding a fusion protein of the invention if it is expressed as a preprotein that participates in the secretion of the fusion protein; a promoter or enhancer is operably linked to a coding sequence if it stimulates the transcription of the sequence. Generally, DNA sequences that are operably linked are contiguous, and in the case of a signal sequence or fusion protein both contiguous and in reading phase. However, enhancers need not be contiguous with the coding sequences whose transcription they control. Linking, in this context, is accomplished by ligation at convenient restriction sites or at adapters or linkers inserted in lieu thereof.

As used herein, the term "promoter" refers to a region of DNA involved in binding RNA polymerase to initiate transcription.

As used herein, the term "subject" can be a human, a mammal, or an animal. The subject being treated is a patient in need of treatment.

As used herein, the term "recombinant" refers to a cell, tissue or organism that has undergone transformation with recombinant DNA.

As used herein, a targeting entity, protein, polypeptide or peptide refers to such molecules that binds specifically to a particular cell type (normal e.g., lymphocytes or abnormal e.g., cancer cell) and therefore may be used to target a transferrin fusion protein or compound (drug, or cytotoxic agent) to that cell type specifically.

As used herein, "therapeutic protein" refers to proteins, polypeptides, antibodies, peptides fragments or variants thereof, having one or more therapeutic and/or biological activities. Therapeutic proteins encompassed by the invention include but are not limited to proteins, polypeptides, peptides, antibodies and biologics. The terms peptides, proteins, and polypeptides are used interchangeably herein and include soluble toxin receptors. Additionally, the term "therapeutic protein" may refer to the endogenous or naturally occurring correlate of a therapeutic protein. By a polypeptide displaying a "therapeutic activity" or a protein that is "therapeutically active" is meant a polypeptide that possesses one or more known biological and/or therapeutic activities associated with a therapeutic protein such as one or more of the therapeutic proteins described herein or otherwise known in the art. As a non-limiting example, a "therapeutic protein" is a protein that is useful to treat, prevent or ameliorate a disease, condition or disorder. Such a disease, condition or disorder may be in humans or in a non-human animal, e.g., veterinary use.

As used herein, "therapeutically effective amount" refers to that amount of the transferrin fusion protein comprising a therapeutic molecule which, when administered to a subject in need thereof, is sufficient to effect treatment. The amount of transferrin fusion protein which constitutes a "therapeutically effective amount" will vary depending on the therapeutic protein used, the severity of the condition or disease, and the age and body weight of the subject to be treated, but can be determined routinely by one of ordinary skill in the art having regard to his/her own knowledge and to this disclosure.

As used herein, the term "toxin" refers to a poisonous substance of biological origin.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation.

As used herein, the term "transgene" refers to a nucleic acid that is inserted into an organism, host cell or vector in a manner that ensures its function.

As used herein, the term "transgenic" refers to cells, cell cultures, organisms, bacteria, fungi, animals, plants, and progeny of any of the preceding, which have received a foreign or modified gene and in particular a gene encoding a modified Tf fusion protein by one of the various methods of transformation, wherein the foreign or modified gene is from the same or different species than the species of the organism receiving the foreign or modified gene.

"Variants or variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide. As used herein, "variant", refers to a therapeutic protein portion of a transferrin fusion protein of the invention, differing in sequence from a native therapeutic protein but retaining at least one functional and/or therapeutic property thereof as described elsewhere herein or otherwise known in the art.

As used herein, the term "vector" refers broadly to any plasmid, phagemid or virus encoding an exogenous nucleic acid. The term is also to be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, *Proc. Natl. Acad. Sci. U.S.A.* 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "wild type" refers to a polynucleotide or polypeptide sequence that is naturally occurring.

Transferrin and Transferrin Modifications

The present invention provides fusion proteins comprising therapeutic protein or soluble toxin receptor fragment and transferrin or modified transferrin. Preferably, the therapeutic proteins provided by the present invention include β-IFN, GLP-1, EMP1, and T-20. Preferably, the soluble toxin receptor fragment is amino acids 1–53 (SEQ ID NO: 4) of synaptotagmin 1. Any transferrin may be used to make modified Tf fusion proteins of the invention.

Wild-type human Tf (Tf) is a 679 amino acid protein, of approximately 75 kDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety, as well as SEQ ID NOS: 1, 2 and 3. The two domains have diverged over time but retain a large degree of identity/similarity (FIG. 1).

Each of the N and C domains is further divided into two subdomains, N1 and N2, C1 and C2. The function of Tf is to transport iron to the cells of the body. This process is mediated by the Tf receptor (TfR), which is expressed on all cells, particularly actively growing cells. TfR recognizes the iron bound form of Tf (two of which are bound per receptor), endocytosis then occurs whereby the TfR/Tf complex is transported to the endosome, at which point the localized drop in pH results in release of bound iron and the recycling of the TfR/Tf complex to the cell surface and release of Tf (known as apoTf in its un-iron bound form). Receptor binding is through the C domain of Tf. The two glycosylation sites in the C domain do not appear to be involved in receptor binding as unglycosylated iron bound Tf does bind the receptor.

Each Tf molecule can carry two iron atoms. These are complexed in the space between the N1 and N2, C1 and C2 subdomains resulting in a conformational change in the molecule. Tf crosses the blood brain barrier (BBB) via the Tf receptor.

In human transferrin, the iron binding sites comprise at least of amino acids Asp 63 (Asp 82 of SEQ ID NO: 2 which comprises the native Tf signal sequence); Asp 392 (Asp 411 of SEQ ID NO: 2); Tyr 95 (Tyr 114 of SEQ ID NO: 2); Tyr 426 (Tyr 445 of SEQ ID NO: 2); Tyr 188 (Tyr 207 of SEQ ID NO: 2); Tyr 514 or 517 (Tyr 533 or Tyr 536 SEQ ID NO:2); His 249 (His 268 of SEQ ID NO: 2); His 585 (His 604 of SEQ ID NO: 2), the hinge regions comprise at least N domain amino acid residues 94–96, 245–247 and/or 316–318 as well as C domain amino acid residues 425–427, 581–582 and/or 652–658., the carbonate binding sites comprise at least of amino acids Thr 120 (Thr 139 of SEQ ID NO: 2); Thr 452 (Thr 471 of SEQ ID NO: 2); Arg 124 (Arg 143 of SEQ ID NO: 2); Arg 456 (Arg 475 of SEQ ID NO: 2); Ala 126 (Ala 145 of SEQ ID NO: 2); Ala 458 (Ala 477 of SEQ ID NO: 2); Gly 127 (Gly 146 of SEQ ID NO: 2); Gly 459 (Gly 478 of SEQ ID NO: 2).

In one embodiment of the invention, the transferrin fusion protein includes a modified human transferrin, although any animal Tf molecule may be used to produce the fusion proteins of the invention, including human Tf variants, cow, pig, sheep, dog, rabbit, rat, mouse, hamster, echnida, platypus, chicken, frog, hornworm, monkey, as well as other bovine, canine and avian species (see FIG. 2 for a representative set of Tf sequences). All of these Tf sequences are readily available in GenBank and other public databases. The human Tf nucleotide sequence is available (see SEQ ID NOS: 1, 2 and 3 and the accession numbers described above and available at www.ncbi.nlm.nih.gov/) and can be used to make genetic fusions between Tf or a domain of Tf and the therapeutic molecule of choice. Fusions may also be made from related molecules such as lacto transferrin (lactoferrin) GenBank Acc: NM_002343) and melanotransferrin (GenBank Acc. NM_013900, murine melanotransferrin).

Lactoferrin (Lf), a natural defense iron-binding protein, has been found to possess antibacterial, antimycotic, antiviral, antineoplastic and anti-inflammatory activity. The protein is present in exocrine secretions that are commonly exposed to normal flora: milk, tears, nasal exudate, saliva, bronchial mucus, gastrointestinal fluids, cervico-vaginal mucus and seminal fluid. Additionally, Lf is a major constituent of the secondary specific granules of circulating polymorphonuclear neutrophils (PMNs). The apoprotein is released on degranulation of the PMNs in septic areas. A principal function of Lf is that of scavenging free iron in fluids and inflamed areas so as to suppress free radical-mediated damage and decrease the availability of the metal to invading microbial and neoplastic cells. In a study that examined the turnover rate of $^{125}$I Lf in adults, it was shown that LF is rapidly taken up by the liver and spleen, and the radioactivity persisted for several weeks in the liver and spleen (Bennett et al. (1979), *Clin. Sci.* (Lond.) 57: 453–460).

Melanotransferrin is a glycosylated protein found at high levels in malignant melanoma cells and was originally named human melanoma antigen p97 (Brown et al., 1982, Nature, 296: 171–173). It possesses high sequence homology with human serum transferrin, human lactoferrin, and chicken transferrin (Brown et al., 1982, Nature, 296: 171–173; Rose et al., Proc. Natl. Acad. Sci., 1986, 83: 1261–1265). However, unlike these receptors, no cellular receptor has been identified for melanotransferrin. Melanotransferrin reversibly binds iron and it exists in two forms, one of which is bound to cell membranes by a glycosyl phosphatidylinositol anchor while the other form is both soluble and actively secreted (Baker et al., 1992, FEBS Lett, 298: 215–218; Alemany et al., 1993, J. Cell Sci., 104: 1155–1162; Food et al., 1994, J. Biol. Chem. 274: 7011–7017).

In another embodiment, the transferrin portion of the transferrin fusion protein of the invention includes a transferrin splice variant. In one example, a transferrin splice variant can be a splice variant of human transferrin. In one specific embodiment, the human transferrin splice variant can be that of Genbank Accession AAA61140.

In another embodiment, the transferrin portion of the transferrin fusion protein of the invention includes a lactoferrin splice variant. In one example, a human serum lactoferrin splice variant can be a novel splice variant of a neutrophil lactoferrin. In one specific embodiment, the neutrophil lactoferrin splice variant can be that of Genbank Accession AAA59479. In another specific embodiment, the neutrophil lactoferrin splice variant can comprise the following amino acid sequence EDCIALKGEADA (SEQ ID NO: 5), which includes the novel region of splice-variance.

Modified Tf fusions may be made with any Tf protein, fragment, domain, or engineered domain. For instance, fusion proteins may be produced using the full-length Tf sequence, with or without the native Tf signal sequence. Transferrin fusion proteins may also be made using a single Tf domain, such as an individual N or C domain. In some embodiments, the use of a single or double N domain is advantageous as the Tf glycosylation sites reside in the C domain and the N domain, on its own, does not bind iron or the Tf receptor. In other embodiments, fusions of a therapeutic protein to a single or double C domain may be produced, wherein the C domain is altered to reduce, inhibit or prevent glycosylation, iron binding and/or Tf receptor binding. See U.S. Provisional Application 60/406,977, which is herein incorporated by reference in its entirety.

As used herein, a C terminal domain or lobe modified to function as an N-like domain is modified to exhibit glycosylation patterns or iron binding properties substantially like that of a native or wild-type N domain or lobe. In a preferred embodiment, the C domain or lobe is modified so that it is not glycosylated and does not bind iron by substitution of the relevant C domain regions or amino acids to those present in the corresponding regions or sites of a native or wild-type N domain.

As used herein, a Tf moiety comprising "two N domains or lobes" includes a Tf molecule that is modified to replace the native C domain or lobe with a native or wild-type N domain or lobe or a modified N domain or lobe or contains a C domain that has been modified to function substantially like a wild-type or modified N domain.

Analysis of the two domains by overlay of the two domains (Swiss PDB Viewer 3.7b2, Iterative Magic Fit) and by direct amino acid alignment (ClustalW multiple alignment) reveals that the two domains have diverged over time. Amino acid alignment shows 42% identity and 59% similarity between the two domains. However, approximately 80% of the N domain matches the C domain for structural equivalence. The C domain also has several extra disulfide bonds compared to the N domain.

Alignment of molecular models for the N and C domain reveals the following structural equivalents:

| N domain (1–330) | 4–24 | 36–72 75–88 | 94–136 | 138–139 | 149–164 | 168–173 | 178–198 200–214 | 219–255 | 259–260 | 263–268 | 271–275 | 279–280 | 283–288 290–304 | 309–327 |
|---|---|---|---|---|---|---|---|---|---|---|---|---|---|---|
| C domain (340–679) | 340–361 | 365–415 | 425–437 439–468 | 470–471 | 475–490 | 492–497 | 507–542 | 555–591 | 593–594 | 597–602 | 605–609 | 614–615 | 620–640 | 645–663 |

The disulfide bonds for the two domains align as follows:

| N | C |
|---|---|
|  | *C339–C596* |
| C9–C48 | C345–C377 |
| C19–C39 | C355–C368 |
|  | C402–C674 |
|  | C418–C637 |
| C118–C194 | C450–C523 |
| *C137–C331* |  |
|  | C474–C665 |
| C158–C174 | C484–C498 |
| C161–C179 |  |
| C171–C177 | C495–C506 |
| C227–C241 | C563–C577 |
|  | C615–C620 |

Bold
*Italics*

In one embodiment, the transferrin portion of the transferrin fusion protein includes at least two N terminal lobes of transferrin. In further embodiments, the transferrin portion of the transferrin fusion protein includes at least two N terminal lobes of transferrin derived from human serum transferrin.

In another embodiment, the transferrin portion of the transferrin fusion protein includes, comprises, or consists of at least two N terminal lobes of transferrin having a mutation in at least one amino acid residue selected from the group consisting of Asp63, Gly65, Tyr95, Tyr188, and His249 of SEQ ID NO: 3.

In another embodiment, the transferrin portion of the modified transferrin fusion protein includes a recombinant human serum transferrin N-terminal lobe mutant having a mutation at Lys206 or His207 of SEQ ID NO: 3.

In another embodiment, the transferrin portion of the transferrin fusion protein includes, comprises, or consists of at least two C terminal lobes of transferrin. In further embodiments, the transferrin portion of the transferrin fusion protein includes at least two C terminal lobes of transferrin derived from human serum transferrin.

In a further embodiment, the C terminal lobe mutant further includes a mutation of at least one of Asn413 and Asn611 of SEQ ID NO: 3 which does not allow glycosylation.

In another embodiment, the transferrin portion of the transferrin fusion protein includes at least two C terminal lobes of transferrin having a mutation in at least one amino acid residue selected from the group consisting of Asp392, Tyr426, Tyr514, Tyr517 and His585 of SEQ ID NO: 3, wherein the mutant retains the ability to bind metal. In an alternate embodiment, the transferrin portion of the transferrin fusion protein includes at least two C terminal lobes of transferrin having a mutation in at least one amino acid residue selected from the group consisting of Tyr426, Tyr514, Tyr517 and His585 of SEQ ID NO: 3, wherein the mutant has a reduced ability to bind metal. In another embodiment, the transferrin portion of the transferrin fusion protein includes at least two C terminal lobes of transferrin having a mutation in at least one amino acid residue selected from the group consisting of Asp392, Tyr426, Tyr517 and His585 of SEQ ID NO:3, wherein the mutant does not retain the ability to bind metal and functions substantially like an N domain.

In some embodiments, the Tf or Tf portion will be of sufficient length to increase the serum stability, in vitro solution stability or bioavailability of the therapeutic protein or peptide or soluble toxin receptor compared to the serum stability (half-life), in vitro stability or bioavailability of therapeutic protein or peptide or soluble toxin receptor in an unfused state. Such an increase in stability, serum half-life or bioavailability may be about a 30%, 50%, 70%, 80%, 90% or more increase over the unfused therapeutic protein or peptide or soluble toxin receptor. In some cases, the transferrin fusion proteins comprising modified transferrin exhibit a serum half-life of about 10–20 or more days, about 12–18 days or about 14–17 days.

When the C domain of Tf is part of the transferrin fusion protein, the two N-linked glycosylation sites, amino acid residues corresponding to N413 and N611of SEQ ID NO:3 may be mutated for expression in a yeast system to prevent glycosylation or hypermannosylationn and extend the serum half-life of the fusion protein and/or therapeutic protein or peptide or soluble toxin receptor (to produce asialo-, or in some instances, monosialo-Tf or disialo-Tf). In addition to Tf amino acids corresponding to N413 and N611, mutations may be to the adjacent residues within the N-X-S/T glycosylation site to prevent or substantially reduce glycosylation. See U.S. Pat. No. 5,986,067 of Funk et al. It has also been reported that the N domain of Tf expressed in *Pichia pastoris* becomes O-linked glycosylated with a single hexose at S32 which also may be mutated or modified to prevent such glycosylation.

Accordingly, in one embodiment of the invention, the transferrin fusion protein includes a modified transferrin molecule wherein the transferrin exhibits reduced glycosylation, including but not limited to asialo-monosialo- and disialo-forms of Tf. In another embodiment, the transferrin portion of the transferrin fusion protein includes a recombinant transferrin mutant that is mutated to prevent glycosylation. In another embodiment, the transferrin portion of the transferrin fusion protein includes a recombinant transferrin mutant that is fully glycosylated. In a further embodiment, the transferrin portion of the transferrin fusion protein includes a recombinant human serum transferrin mutant that is mutated to prevent glycosylation, wherein at least one of Asn413 and Asn611 of SEQ ID NO:3 are mutated to an amino acid which does not allow glycosylation. In another embodiment, the transferrin portion of the transferrin fusion protein includes a recombinant human serum transferrin mutant that is mutated to prevent or substantially reduce glycosylation, wherein mutations may be to the adjacent residues within the N-X-S/T glycosylation site.

As discussed below in more detail, modified Tf fusion proteins of the invention may also be engineered to not bind iron and/or not bind the Tf receptor. In other embodiments of the invention, the iron binding is retained and the iron binding ability of Tf may be used in two ways, one to deliver a therapeutic protein or peptide(s) to the inside of a cell and/or across the BBB. These embodiments that bind iron and/or the Tf receptor will often be engineered to reduce or prevent glycosylation to extend the serum half-life of the therapeutic protein. The N domain alone will not bind to TfR when loaded with iron, and the iron bound C domain will bind TfR but not with the same affinity as the whole molecule.

In another embodiment, the transferrin portion of the transferrin fusion protein includes a recombinant transferrin mutant having a mutation wherein the mutant does not retain the ability to bind metal. In an alternate embodiment, the transferrin portion of the transferrin fusion protein includes a recombinant transferrin mutant having a mutation wherein the mutant has a weaker binding avidity for metal than wild-type serum transferrin. In an alternate embodiment, the transferrin portion of the transferrin fusion protein includes a recombinant transferrin mutant having a mutation wherein the mutant has a stronger binding avidity for metal than wild-type serum transferrin.

In another embodiment, the transferrin portion of the transferrin fusion protein, includes a recombinant transferrin mutant having a mutation wherein the mutant does not retain the ability to bind to the transferrin receptor. In an alternate embodiment, the transferrin portion of the transferrin fusion protein includes a recombinant transferrin mutant having a mutation wherein the mutant has a weaker binding avidity for the transferrin receptor than wild-type serum transferrin. In an alternate embodiment, the transferrin portion of the transferrin fusion protein includes a recombinant transferrin mutant having a mutation wherein the mutant has a stronger binding avidity for the transferrin receptor than wild-type serum transferrin.

In another embodiment, the transferrin portion of the transferrin fusion protein includes a recombinant transferrin mutant having a mutation wherein the mutant does not retain the ability to bind to carbonate. In an alternate embodiment, the transferrin portion of the transferrin fusion protein includes a recombinant transferrin mutant having a mutation wherein the mutant has a weaker binding avidity for carbonate than wild-type serum transferrin. In an alternate embodiment, the transferrin portion of the transferrin fusion protein includes a recombinant transferrin mutant having a mutation wherein the mutant has a stronger binding avidity for carbonate than wild-type serum transferrin.

In another embodiment, the transferrin portion of the transferrin fusion protein includes a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant retains the ability to bind metal. In an alternate embodiment, a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant has a reduced ability to bind metal. In another embodiment, a recombinant human serum transferrin mutant having a mutation in at least one amino acid residue selected from the group consisting of Asp63, Gly65, Tyr95, Tyr188, His249, Asp392, Tyr426, Tyr517 and His585 of SEQ ID NO: 3, wherein the mutant does not retain the ability to bind metal.

In another embodiment, the transferrin portion of the transferrin fusion protein includes a recombinant human serum transferrin mutant having a mutation at Lys206 or His207 of SEQ ID NO: 3, wherein the mutant has a stronger binding avidity for metal than wild-type human serum transferrin (see U.S. Pat. No. 5,986,067, which is herein incorporated by reference in its entirety). In an alternate embodiment, the transferrin portion of the transferrin fusion protein includes a recombinant human serum transferrin mutant having a mutation at Lys206 or His207 of SEQ ID NO: 3, wherein the mutant has a weaker binding avidity for metal than wild-type human serum transferrin. In a further embodiment, the transferrin portion of the transferrin fusion protein includes a recombinant human serum transferrin mutant having a mutation at Lys206 or His207 of SEQ ID NO:3, wherein the mutant does not bind metal.

Any available technique may be used to produce the transferrin fusion proteins of the invention, including but not limited to molecular techniques commonly available, for instance, those disclosed in Sambrook et al. Molecular Cloning: A Laboratory Manual, 2nd Ed., Cold Spring Harbor Laboratory Press, 1989. When carrying out nucleotide substitutions using techniques for accomplishing site-specific mutagenesis that are well known in the art, the encoded amino acid changes are preferably of a minor nature, that is, conservative amino acid substitutions, although other, non-conservative, substitutions are contemplated as well, particularly when producing a modified transferrin portion of a Tf fusion protein, e.g., a modified Tf protein exhibiting reduced glycosylation, reduced iron binding and the like. Specifically contemplated are amino acid substitutions, small deletions or insertions, typically of one to about 30 amino acids; insertions between transferrin domains; small amino- or carboxyl-terminal extensions, such as an amino-terminal methionine residue, or small linker peptides of less than 50, 40, 30, 20 or 10 residues between transferrin domains or linking a transferrin protein and therapeutic protein or peptide or soluble toxin receptor or a small extension that facilitates purification, such as a poly-histidine tract, an antigenic epitope or a binding domain.

Examples of conservative amino acid substitutions are substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

Non-conservative substitutions encompass substitutions of amino acids in one group by amino acids in another group. For example, a non-conservative substitution would include the substitution of a polar amino acid for a hydrophobic amino acid. For a general description of nucleotide substitution, see e.g. Ford et al. (1991), *Prot. Exp. Pur.* 2: 95–107. Non-conservative substitutions, deletions and insertions are particularly useful to produce Tf fusion proteins of the invention that exhibit no or reduced binding of iron, no or reduced binding of the fusion protein to the Tf receptor and/or no or reduced glycosylation.

Iron binding and/or receptor binding may be reduced or disrupted by mutation, including deletion, substitution or insertion into, amino acid residues corresponding to one or more of Tf N domain residues Asp63, Tyr95, Tyr188, His249 and/or C domain residues Asp 392, Tyr 426, Tyr 514 and/or His 585. Iron binding may also be affected by mutation to amino acids Lys206, Hys207 or Arg632. Carbonate binding may be reduced or disrupted by mutation, including deletion, substitution or insertion into, amino acid residues corresponding to one or more of Tf N domain residues Thr120, Arg124, Ala126, Gly 127 and/or C domain residues Thr 452, Arg 456, Ala 458 and/or Gly 459. A reduction or disruption of carbonate binding may adversely affect iron and/or receptor binding.

Binding to the Tf receptor may be reduced or disrupted by mutation, including deletion, substitution or insertion into, amino acid residues corresponding to one or more of Tf N domain residues described above for iron binding.

As discussed above, glycosylation may be reduced or prevented by mutation, including deletion, substitution or insertion into, amino acid residues corresponding to one or more of Tf C domain residues around the N-X-S/T sites corresponding to C domain residues N413 and/or N611 (See U.S. Pat. No. 5,986,067). For instance, the N413 and/or N611 may be mutated to Glu residues.

In instances where the Tf fusion proteins of the invention are not modified to prevent glycosylation, iron binding, carbonate binding and/or receptor binding, glycosylation, iron and/or carbonate ions may be stripped from or cleaved off of the fusion protein. For instance, available de-glycosylases may be used to cleave glycosylation residues from the fusion protein, in particular the sugar residues attached to the Tf portion, yeast deficient in glycosylation-enzymes may be used to prevent glycosylation and/or recombinant cells may be grown in the presence of an agent that prevents glycosylation, e.g., tunicamycin.

Additional mutations may be made with Tf to alter the three dimensional structure of Tf, such as modifications to the hinge region to prevent Tf folding needed for iron biding and Tf receptor recognition. For instance, mutations may be made in or around N domain amino acid residues 94–96, 245–247 and/or 316–318 as well as C domain amino acid residues 425–427, 581–582 and/or 652–658. In addition, mutations may be made in to or around the flanking regions of these sites to alter Tf structure and function.

In one aspect of the invention, the transferrin fusion protein can function as a carrier protein to extend the half life or bioavailability of the therapeutic protein as well as in some instances, delivering the therapeutic protein inside a cell and/or across the blood brain barrier. In an alternate embodiment, the transferrin fusion protein includes a modified transferrin molecule wherein the transferrin does not retain the ability to cross the blood brain barrier.

In another embodiment, the transferrin fusion protein includes a modified transferrin molecule wherein the transferrin molecule retains the ability to bind to the transferrin receptor and transport the therapeutic protein or peptide or soluble toxin receptor inside cells. In an alternate embodiment, the transferrin fusion protein includes a modified transferrin molecule wherein the transferrin molecule does not retain the ability to bind to the transferrin receptor and transport the therapeutic protein inside cells.

In further embodiments, the transferrin fusion protein includes a modified transferrin molecule wherein the transferrin molecule retains the ability to bind to the transferrin receptor and transport the therapeutic protein inside cells, but does not retain the ability to cross the blood brain barrier. In an alternate embodiment, the transferrin fusion protein includes a modified transferrin molecule wherein the transferrin molecule retains the ability to cross the blood brain barrier, but does not retain the ability to bind to the transferrin receptor and transport the therapeutic protein inside cells.

Modified Transferrin Fusion Proteins

The fusion of proteins of the invention may contain one or more copies of the therapeutic proteins or peptides or soluble toxin receptor attached to the N-terminus and/or the C-terminus of the Tf protein. In some embodiments, the therapeutic protein is attached to both the N- and C-terminus of the Tf protein and the fusion protein may contain one or more equivalents of the therapeutic protein on either or both ends of Tf. In other embodiments, the therapeutic protein is inserted into known domains of the Tf protein, for instance, into one or more of the loops of Tf (see All et al. (1999) *J. Biolog. Chem.* 274(34):24066–24073). In fact, the therapeutic protein may be inserted into all five loops of transferrin to create a pentavalent molecule with increased avidity for the antigen, receptor, or targeting molecule, which the therapeutic protein binds. In other embodiments, the therapeutic protein is inserted between the N and C domains of Tf. Alternatively, the therapeutic protein is inserted anywhere in the transferrin molecule.

Generally, the transferrin fusion protein of the invention may have one modified transferrin-derived region and one therapeutic protein region. Multiple regions of each protein, however, may be used to make a transferrin fusion protein of the invention. Similarly, more than one therapeutic protein may be used to make a transferrin fusion protein of the invention of the invention, thereby producing a multi-functional modified Tf fusion protein.

In one embodiment, the transferrin fusion protein of the invention contains a therapeutic protein or portion thereof or a soluble toxin receptor fused to a transferrin molecule or portion thereof. In another embodiment, the transferrin fusion protein of the inventions contains a therapeutic protein fused to the N terminus of a transferrin molecule. In an alternate embodiment, the transferrin fusion protein of the invention contains a therapeutic protein fused to the C terminus of a transferrin molecule. In a further embodiment, the transferrin fusion protein of the invention contains a transferrin molecule fused to the N terminus of a therapeutic protein. In an alternate embodiment, the transferrin fusion protein of the invention contains a transferrin molecule fused to the C terminus of a therapeutic protein.

In further embodiments, the modified transferrin molecule contains the N terminus of a transferrin molecule fused to what would be the N terminus of a therapeutic protein. In an alternate embodiment, the modified transferrin molecule contains the N terminus of a transferrin molecule fused to the C terminus of a therapeutic protein. In a further alternate embodiment, the modified transferrin molecule contains the C terminus of a transferrin molecule fused to what would be the C terminus of a therapeutic protein. In an alternate embodiment, the modified transferrin molecule contains the C terminus of a transferrin molecule fused to the N terminus of a therapeutic protein.

In other embodiments, the transferrin fusion protein of the inventions contains a therapeutic protein fused to both the N-terminus and the C-terminus of modified transferrin. In another embodiment, the therapeutic proteins fused at the N- and C-termini bind the same therapeutic proteins. In an alternate embodiment, the therapeutic proteins fused at the N- and C-termini are different therapeutic proteins. In another alternate embodiment, the therapeutic proteins fused to the N- and C-termini bind different therapeutic proteins which may be used to treat or prevent the same disease, disorder, or condition. In another embodiment, the therapeutic proteins fused at the N- and C-termini are different therapeutic proteins which may be used to treat or prevent diseases or disorders which are known in the art to commonly occur in patients simultaneously.

In addition to modified transferrin fusion protein of the invention in which the modified transferrin portion is fused to the N terminal and/or C-terminal of the therapeutic protein portion, transferrin fusion protein of the invention may also be produced by inserting the therapeutic protein or peptide of interest (e.g., a therapeutic protein or peptide as disclosed herein, or a fragment or variant thereof) into an internal region of the modified transferrin. Internal regions of modified transferrin include, but are not limited to, the iron binding sites, the hinge regions, the bicarbonate binding sites, or the receptor binding domain.

Within the protein sequence of the modified transferrin molecule a number of loops or turns exist, which are stabilized by disulfide bonds. These loops are useful for the insertion, or internal fusion, of therapeutically active peptides particularly those requiring a secondary structure to be functional, or therapeutic proteins to essentially generate a modified transferrin molecule with specific biological activity. When therapeutic proteins are inserted into or replace at least one loop of a Tf molecule, insertions may be made within any of the surface exposed loop regions, in addition to other areas of Tf. For instance, insertions may be made within the loops comprising Tf amino acids 32–33, 74–75, 256–257, 279–280 and 288–289 (All et al., supra) (See FIG. 3). As previously described, insertions may also be made within other regions of Tf such as the sites for iron and bicarbonate binding, hinge regions, and the receptor binding domain as described in more detail below. The loops in the Tf protein sequence that are amenable to modification/replacement for the insertion of proteins or peptides may also be used for the development of a screenable library of random peptide inserts. Any procedures may be used to produce nucleic acid inserts for the generation of peptide libraries, including available phage and bacterial display systems, prior to cloning into a Tf domain and/or fusion to the ends of Tf.

The N-terminus of Tf is free and points away from the body of the molecule. Fusions of proteins or peptides on the N-terminus may therefore be a preferred embodiment. Such fusions may include a linker region, such as but not limited to a poly-glycine stretch, to separate the therapeutic protein from Tf. Attention to the junction between the leader sequence, the choice of leader sequence, and the structure of the mRNA by codon manipulation/optimization (no major stem loops to inhibit ribosome progress) will increase secretion and can be readily accomplished using standard recombinant protein techniques.

The C-terminus of Tf appears to be more buried and secured by a disulfide bond 6 amino acids from the C-terminus. In human Tf, the C-terminal amino acid is a proline which, depending on the way that it is orientated, will either point a fusion away or into the body of the molecule. A linker or spacer moiety at the C-terminus may be used in some embodiments of the invention.

In yet other embodiments, small molecule therapeutics may be complexed with iron and loaded on a modified transferrin fusion protein for delivery to the inside of cells and across the BBB. The addition of a targeting peptide or, for example, a SCA will target the payload to a particular cell type, e.g., a cancer cell.

Therapeutic Proteins and Peptides

Any therapeutic molecule may be used as the fusion partner to Tf according to the methods and compositions of the present invention. As used herein, a therapeutic molecule is typically a protein or peptide capable of exerting a beneficial biological effect in vitro or in vivo and includes proteins or peptides that exert a beneficial effect in relation to normal homeostasis, physiology or a disease state. Therapeutic molecules do not include, fusion partners commonly used as markers or protein purification aids, such as galactosidases (see for example, U.S. Pat. No. 5,986,067 and Aldred et al. (1984) *Biochem. Biophys. Res. Commun*. 122: 960–965). For instance, a beneficial effect as related to a disease state includes any effect that is advantageous to the treated subject, including disease prevention, disease stabilization, the lessening or alleviation of disease symptoms or a modulation, alleviation or cure of the underlying defect to produce an effect beneficial to the treated subject.

A modified transferrin fusion protein of the invention includes at least a fragment or variant of a therapeutic protein and at least a fragment or variant of modified serum transferrin, which are associated with one another, preferably by genetic fusion or chemical conjugation.

In one embodiment, the transferrin fusion protein includes a modified transferrin molecule linked to a neuropharmaceutical agent. In another embodiment, the modified transferrin fusion protein includes transferrin at the carboxyl terminus linked to a neuropharmaceutical agent at the amino terminus. In an alternate embodiment, the modified transferrin fusion protein includes transferrin at the amino terminus linked to a neuropharmaceutical agent at the carboxy terminus. In specific embodiments, the neuropharmaceutical agent is either nerve growth factor or ciliary neurotrophic factor.

In further embodiments, a modified transferrin fusion protein of the invention may contain at least a fragment or variant of a therapeutic protein. In a further embodiment, the transferrin fusion proteins can contain peptide fragments or peptide variants of proteins or antibodies wherein the variant or fragment retains at least one biological or therapeutic activity. The transferrin fusion proteins can contain therapeutic proteins that can be peptide fragments or peptide variants at least about 4, at least 5, at least 6, at least 7, at least 8, at least 9, at least 10, at least 11, at least 12, at least 13, at least 14, at least 15, at least 20, at least 25, at least 30, at least 35, or at least about 40, at least about 50, at least about 55, at least about 60 or at least about 70 or more amino acids in length fused to the N and/or C termini, inserted within, or inserted into a loop of a modified transferrin.

The modified transferrin fusion proteins of the present invention may contain one or more peptides. Increasing the number of peptides enhances the function of the peptides fused to transferrin and the function of the entire transferrin fusion protein. The peptides may be used to make a bi- or multi-functional fusion protein by including peptide or protein domains with multiple functions. For instance, a multi-functional fusion protein can be made with a therapeutic protein and a second protein to target the fusion protein to a specific target. Other peptides may be used to induce the immune response of a cellular system, or induce an antiviral, antibacterial, or anti-pathogenic response.

In another embodiment, the modified transferrin fusion molecules contain a therapeutic protein portion that can be fragments of a therapeutic protein that include the full length protein as well as polypeptides having one or more residues deleted from the amino terminus of the amino acid sequence.

In another embodiment, the modified transferrin fusion molecules contain a therapeutic protein portion that can be fragments of a therapeutic protein that include the full length protein as well as polypeptides having one or more residues deleted from the carboxy terminus of the amino acid sequence.

In another embodiment, the modified transferrin fusion molecules contain a therapeutic protein portion that can have one or more amino acids deleted from both the amino and the carboxy termini.

In another embodiment, the modified transferrin fusion molecules contain a therapeutic protein portion that is at least about 80%, 85%, 90%, 95%, 96%, 97%, 98% or 99% identical to a reference therapeutic protein set forth herein, or fragments thereof. In further embodiments, the transferrin fusion molecules contain a therapeutic protein portion that is at least about 80%, 85%, 90%, 95%, 96%, 97%, 98% or 99% identical to reference polypeptides having the amino acid sequence of N- and C-terminal deletions as described above.

In another embodiment, the modified transferrin fusion molecules contain the therapeutic protein portion that is at least about 80%, 85%, 90%, 95%, 96%, 97%, 98%, 99% or 100%, identical to, for example, the native or wild-type amino acid sequence of a therapeutic protein. Fragments, of these polypeptides are also provided.

The therapeutic proteins corresponding to a therapeutic protein portion of a modified transferrin fusion protein of the invention, such as cell surface and secretory proteins, can be modified by the attachment, of one or more oligosaccharide groups. The modification referred to as glycosylation, can significantly affect the physical properties of proteins and can be important in protein stability, secretion, and localization. Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be an amino add except proline. Variables such as protein structure and cell type influence the number and nature of the carbohydrate units within the chains at different glycosylation sites. Glycosylation isomers are also common at the same site within a given cell type. For example, several types of human interferon are glycosylated.

Therapeutic proteins corresponding to a therapeutic protein portion of a transferrin fusion protein of the invention, as well as analogs and variants thereof, may be modified so that glycosylation at one or more sites is altered as a result of manipulation(s) of their nucleic acid sequence by the host cell in which they are expressed, or due to other conditions of their expression. For example, glycosylation isomers may be produced by abolishing or introducing glycosylation sites, e.g., by substitution or deletion of amino acid residues, such as substitution of glutamine for asparagine, or unglycosylated recombinant proteins may be produced by expressing the proteins in host cells that will not glycosylate them, e.g. in glycosylation-deficient yeast. These approaches are known in the art.

Therapeutic proteins and their nucleic acid sequences are well known in the art and available in public databases such as Chemical Abstracts Services Databases (e.g., the CAS Registry), GenBank, and GenSeq. The Accession Numbers and sequences referred to below are herein incorporated by reference in their entirety.

In other embodiments, the transferrin fusion proteins of the invention are capable of a therapeutic activity and/or biologic activity, corresponding to the therapeutic activity and/or biologic activity of the therapeutic protein described elsewhere in this application. In further embodiments, the therapeutically active protein portions of the transferrin fusion proteins of the invention are fragments or variants of the reference sequences cited herein.

The present invention is further directed to modified Tf fusion proteins comprising fragments of the therapeutic proteins herein described. Even if deletion of one or more amino acids from the N-terminus of a protein results in modification or loss of one or more biological functions of the therapeutic protein portion, other therapeutic activities and/or functional activities (e.g., biological activities, ability to multimerize, ability to bind a ligand) may still be retained. For example, the ability of polypeptides with N-terminal deletions to induce and/or bind to antibodies which recognize the complete or mature forms of the polypeptides generally will be retained with less than the majority of the residues of the complete polypeptide removed from the N-terminus. Whether a particular polypeptide lacking N-terminal residues of a complete polypeptide retains such immunologic activities can be assayed by routine methods described herein and otherwise known in the art. It is not unlikely that a mutant with a large number of deleted N-terminal amino acid residues may retain some biological or immunogenic activities. In fact, peptides composed of as few as six amino acid residues may often evoke an immune response.

Also as mentioned above, even if deletion of one or more amino acids from the N-terminus or C-terminus of a therapeutic protein results in modification or loss of one or more biological functions of the protein, other functional activities (e.g., biological activities, ability to multimerize, ability to bind a ligand) and/or therapeutic activities may still be retained. For example the ability of polypeptides with C-terminal deletions to induce and/or bind to antibodies which recognize the complete or mature forms of the polypeptide generally will be retained when less than the majority of the residues of the complete or mature polypeptide are removed from the C-terminus. Whether a particular polypeptide lacking the N-terminal and/or, C-terminal residues of a reference polypeptide retains therapeutic activity can readily be determined by routine methods described herein and/or otherwise known in the art.

Peptide fragments of the therapeutic proteins can be fragments comprising, or alternatively, consisting of, an amino acid sequence that displays a therapeutic activity and/or functional activity (e.g. biological activity) of the polypeptide sequence of the therapeutic protein of which the amino acid sequence is a fragment.

Other polypeptide fragments are biologically active fragments. Biologically active fragments are those exhibiting activity similar, but not necessarily identical, to an activity of a therapeutic protein used in the present invention. The biological activity of the fragments may include an improved desired activity, or a decreased undesirable activity.

Generally, variants of proteins are overall very similar, and, in many regions, identical to the amino acid sequence of the therapeutic protein corresponding to a therapeutic protein portion of a transferrin fusion protein of the invention. Nucleic acids encoding these variants are also encompassed by the invention.

Further therapeutic polypeptides that may be used in the invention are polypeptides encoded by polynucleotides which hybridize to the complement of a nucleic acid molecule encoding an amino acid sequence of a therapeutic protein under stringent hybridization conditions which are known to those of skill in the art. (see, for example, Ausubel, F. M. et al., eds., 1989 Current protocol in Molecular Biology, Green Publishing Associates, Inc., and John Wiley & Sons Inc., New. York). Polynucleotides encoding these polypeptides are also encompassed by the invention.

By a polypeptide-having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence, or in one or more contiguous groups within the reference sequence.

As a practical matter, whether any particular polypeptide is at least about 80%, 85%, 90%,95%, 96%, 97%, 98% or 99% identical to, for instance, the amino acid sequence of a transferrin fusion protein of the invention or a fragment thereof (such, as the therapeutic protein portion of the transferrin fusion protein or the transferrin portion of the transferrin fusion protein), can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brufiag-et al. (Comp. App. Biosci 245-(1990)).

The polynucleotide variants of the invention may contain alterations in the coding regions, non-coding regions, or both. Polynucleotide variants containing alterations which produce silent substitutions, additions, or deletions, but do not alter the properties or activities of the encoded polypeptide may be used to produce modified Tf fusion proteins. Nucleotide variants produced by silent substitutions due to the degeneracy of the genetic code can be utilized. Moreover, polypeptide variants in which less than about 50, less than 40, less than 30, less than 20, less than 10, or 5–50, 5–25, 5–10, 1–5, or 1–2 amino acids are substituted, deleted, or added in any combination can also be utilized. Polynucleotide variants can be produced for a variety of reasons, e.g., to optimize codon expression for a particular host (change codons in the human mRNA to those preferred by a host, such as, yeast or $E.\ Coli$ as described above).

In other embodiments, the therapeutic protein moiety has conservative substitutions compared to the wild-type sequence. By "conservative substitutions" is intended swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Guidance concerning how to make phenotypically silent amino acid substitutions is provided, for example, in Bowie et al., "Deciphering the Message in Protein Sequences: Tolerance to Amino Acid Substitutions," Science 247:1306–1310 (1990). In specific embodiments, the polypeptides of the invention comprise, or alternatively, consist of, fragments or variants of the amino acid sequence of a therapeutic protein described herein and/or serum transferrin, and/modified transferrin protein of the invention, wherein the fragments or variants have 1–5, 5–10, 5–25, 5–50, 10–50 or 50–150 amino acid residue additions, substitutions, and/or deletions when compared to the reference amino acid sequence. In further embodiments, the amino acid substitutions are conservative. Nucleic acids encoding these polypeptides are also encompassed by the invention.

The modified fusion proteins of the present invention can be composed of amino-acids joined to each other by peptide bonds or modified peptide bonds and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, glycosylation, GPI anchor formation, hydroxylation, iodination, methylation, myristylation, oxidation, pegylation, proteolytic processing, phosphorylation, prenylation, racemization, sulfation, transfer-RNA mediated addition of amino acids to proteins such as arginylaltion, and ubiquitination. (See, for instance, PROTEINS—STRUCTURE AND MOLECULAR PROPERTIES, 2nd Ed., T. E. Creighton, W. H. Freeman and Company, New York(1993); POST-TRANSLATIONAL COVALENT MODIFICATION OF PROTEINS, B. C. Johnson, Ed., Academic Press, New York, pgs. 1–12 (1983); Seifter et al. (1990) $Meth.\ Enzymol.$ 182:626–646; Rattan et al., $Ann.\ N.Y\ Acad.\ Sci.$ 663:48–62.

The therapeutic proteins of the present invention include, but are not limited to polypeptide, peptide, antibody, or fragments and variants thereof. Preferably, the therapeutic proteins of the present invention include β-interferon (β-IFN), glucagon-like peptide-1 (GLP-1), EPO mimetic peptide (EMP-1), T-20, and soluble toxin receptor, such as synaptotagmin I.

β-Interferon

Most cytokines, including β-IFN, have relatively short circulation half-lives since they are produced in vivo to act locally and transiently. To use β-IFN as an effective systemic therapeutic, one needs relatively large doses and frequent administrations. Such frequent parenteral administrations are inconvenient and painful. Further, toxic side effects are associated with β-IFN administration which are so severe that some multiple sclerosis patients cannot tolerate the treatment. These side effects are probably associated with administration of a high dosage.

The present invention provides β-IFN/transferrin fusion proteins with increased half-lives and pharmaceutical compositions comprising such fusion proteins with increased stability. Such fusion proteins can be administered to patients at lower doses, thus reducing the toxic side effects associated with β-IFN. The present invention contemplates the use of the β-IFN/transferrin fusion proteins to treat various diseases and conditions associated with β-IFN, such as but not limited to multiple sclerosis, cancer including brain tumors and skin cancer, and viral infections such as hepatitis B and C. Preferably, the β-IFN/transferrin fusion proteins are used to treat subjects suffering from multiple sclerosis.

β-interferon (β-IFN) is a glycoprotein with an apparent molecular weight (MW) of 23 kilodaltons. The gene encoding β-IFN is located on chromosome 9. Its amino acid sequence containing 166 residues was determined by K. Hosoi et al. (J. Interferon Res., 8, pp 375–384 (1988)), and its glucoside sequence was reported by Y. Kagawa et al. ($J.\ Biol.\ Chem.$, 263, pp 17508–17515 (1988)).

β-IFN is secreted by fibroblasts in response to a viral or bacterial infection, or exposure to foreign cells, macromolecules, or RNA. In particular, β-IFN inhibits the proliferation of infected cells and stimulates the immune system. The specific antiviral activity of homogeneous Hu-β-IFN is considered to be between $3 \times 10^8$ and $1 \times 10^9$ iu/mg (international units per milligram of total protein) inclusive (see U.S. Pat. No. 4,289,689 and EP-A-94 672).

"Interferon-beta" (IFN-β) or "beta-interferon" (β-IFN) includes native and recombinant Type I interferons exhibiting the same or similar pharmaceutical characteristics as the Type I interferons commonly known as IFN-β-1a and IFN-β-1b.

Any β-IFN sequence may be used to prepare Tf fusion proteins of the present invention. For instance, U.S. Pat. No. 4,738,931 discloses the human β-IFN gene derived from human chromosomal DNA. A 1.8 Kb EcoRI fragment, containing the nucleic acid encoding the human β-IFN, introduced into *Escherichia coli* has been deposited with the American Type Culture Collection in U.S.A. as *Escherichia coli* C14 under accession number ATCC 31905. The GenBank accession number for the amino acid sequence of Human β-IFN amino acid sequence is AAA72588. The β-IFN could also be a mutein as described in U.S. Pat. No. 4,588,585, in which the cysteine (Cys) normally occurring at position 17 of the wild-type or native molecule has been replaced by a neutral amino acid, such as serine or alanine. Mark et al. (Proc. Natl. Acad. Sci. 81: 5662–5666 (1984)) showed that when Cys 17 was changed for serine, the IFN exhibited the same spectrum of biological activities as β-IFN, such as anticellular and antiproliferative activity, activation of NK cells and neutralization of anti-human IFN antibodies. The mutein also exhibited greater stability than natural human (Hu) β-IFN when incubated at 70° C.

Because of its activity, β-IFN is regarded as an active principle not only in the treatment and prophylaxis of viral diseases such as herpes, influenza etc, but also in the treatment of tumoral conditions such as encephaloma and leukemia. β-IFN is used to treat multiple sclerosis, brain tumor, skin cancer and hepatitis B and C. β-IFN fusion proteins of the present invention may be used to treat any of these diseases.

Human β-IFN is also effective in treating coronary restenosis in humans by selectively inhibiting the proliferation of coronary smooth muscle cell at the site of vascular injury following a surgical procedure while having no inhibitory effect on the normal proliferation of coronary endothelial cells following the procedure. U.S. Pat. No. 5,681,558 discloses a method of treating restenosis comprising administering β-IFN to the patient. Accordingly, β-IFN fusion proteins of the present invention may be used to treat restenosis.

β-IFN has an erythropoietic effect on the growth of progenitor cells from individuals suffering from several diseases with a very low production of red blood cells. Additionally, β-IFN increases burst formation as well as promotes a more rapid maturation toward normoblasts and even late reticulocytes. U.S. Pat. No. 5,104,653 discloses a method for the stimulation of erythropoiesis in a patient suffering from a disorder characterized by lack of maturation of progenitor blood cells to red blood cells comprising administering to said patient an erythropoietic effective amount of human β-IFN. Therefore, β-IFN fusion proteins of the present invention may be used to stimulate erythropoiesis.

β-IFN, acting via STAT1 and STAT2, is known to upregulate and downregulate a wide variety of genes, most of which are involved in the antiviral immune response. Although most IFN responses are induced by the presence of dsRNA, both DNA and RNA viruses are sensitive to the effects of β-IFN (Biron, Seminars in Immunology, 10: 383–390 (1998)).

β-IFN is generally produced in response to a viral infection. Interferon β-IFN exerts its biological effects by binding to specific receptors on the surface of human cells. This binding initiates a complex cascade of intracellular events that leads to the expression of numerous interferon-induced gene products and markers, for example, 2',5'-oligoadenylate synthetase, b$_2$-microglobulin, and neopterin.

(2'-5')-Oligoadenylate synthetase and dsRNA dependent protein kinase are the two best-known IFN-β-induced proteins (Biron, 1998, supra). (2'-5')-oligoadenylate synthetase polymerizes ATP in a unique 2'-5' fashion (Janeway et al., Immunobiology: The Immune System in Health and Disease, 4th Edition, New York, Elsevier Science/Garland Publishing pp 385–386(1999)); the resultant oligomers activate RNase L, which cleaves mRNA (Biron, 1998, supra). dsRNA dependent protein kinase phosphorylates and inactivates elF2, a transcriptional initiator. Both (2'-5')-oligoadenylate synthetase and dsRNA dependent protein kinase act only in the presence of dsRNA, i.e. in virally infected cells. The net result of the action of these two proteins is to inhibit protein translation, which will retard viral replication (Biron, 1998, supra).

β-IFN dependent upregulation of TAP (transporter associated with antigen processing), Lmp2, Lmp7 serves to increase presentation of viral peptides by MHC class I molecules in order to facilitate CD8 T cell recognition and destruction of infected cells. TAP is the molecule responsible for loading peptide fragments onto MHC class I molecules in the ER; the Lmp proteins are components of the proteasome which cleave proteins specifically for MHC class I presentation (Janeway et al., 1999, supra).

β-IFN is known to both activate and induce some proliferation in natural killer (NK) cells (Janeway et al., 1999, supra). However, interferons themselves are not mitogens. The proliferation of NK cells is probably caused by an intermediary cytokine which is induced by IFN-β (Biron, 1998, supra). NK cells can kill cells which exhibit atypical patterns of MHC class I expression; such cells are generally virally infected (Janeway et al., 1999, supra).

Although at the end of a successfully defeated infection, T cells die by apoptosis as the immune system returns to a homeostatic balance, some T cells must avoid apoptosis and enter a G$_0$/G$_1$ memory state to preserve immunological memory. These memory T cells are rescued from apoptosis by interacting with stromal cells, which secrete β-IFN and some IFN-α (Pilling et al., European Journal of Immunology 29:1041–1050 (1999)). T cell apoptosis may be induced by either cytokine deprivation or ligation of Fas on the cell surface, but β-IFN is able to block both apoptotic pathways. The former apoptotic pathway is blocked by β-IFN dependent upregulation of Bcl-x, an apoptotic inhibitor. Fas ligation-induced apoptosis occurs much too quickly to be blocked by upregulation of a gene, so β-IFN must block that apoptotic pathway by different means (Scheel-Toellner et al., European Journal of Immunology 29:2603–2612 (1999)). The existence of a second blocking mechanism is supported by the results of Marrack et al. (Journal of Experimental Medicine 189:521–529(1999)), who found that β-IFN prevented T cell apoptosis without increased production of Bcl-x.

Der et al. (Proceedings of the National Academy of Sciences, USA 95: 15623–15628 (1998)) found that β-IFN increased transcription of well over 100 proteins in human fibrosarcoma cells. Induced proteins ranged in function from cytochromes and cell scaffolding proteins to immunologically active proteins such as Complement components and dsRNA adenosine deaminase. These results indicate that β-IFN has truly pleiotropic effects, many of which are not fully understood.

Much clinical research on β-IFN is currently focused on its use as a treatment for multiple sclerosis (MS). MS is an autoimmune disease in which T cells mount an immune response against self myelin antigens in the glial cells of the central nervous system (Goodkin, 1999. Multiple sclerosis: Treatment options for patients with relapsing-remitting and secondary progressive multiple sclerosis.). In 1993, the FDA approved subcutaneous injections of IFN-β1b for treatment of MS (Revelle M., 1993, FDA licenses interferon beta-1b.). β-IFN 1b is a non-glycosylated form of IFN-β produced by E. coli (Arduini et al., Protein Science 8:1867–1877 (1999)). Adverse experiences associated with β-IFN 1b therapy include: injection site reactions (inflammation, pain, hypersensitivity and necrosis), and a flu-like symptom complex (fever, chills, anxiety and confusion). These adverse side effects may be, in fact, reduced or alleviated by fusing β-IFN 1b to transferrin as described above.

Currently, β-IFN 1a (a eukaryotic, glycosylated form obtained from hamsters) is also available (Goodkin, 1999, supra). β-IFN 1a is produced by recombinant DNA technology. Interferon beta-1a is a 166 amino acid glycoprotein with a predicted molecular weight of approximately 22,500 daltons. It is produced by mammalian cells (Chinese Hamster Ovary cells) into which the human IFN-β gene has been introduced. The amino acid sequence of β-IFN 1a is identical to that of natural human β-IFN and may be used to make Tf fusion proteins of the present invention.

β-IFN/transferrin fusion proteins treatment may also ameliorate autoimmune attacks by restoring suppressor T cell function; cotreatment with all-trans-retinoic acid seems to increase this restorative action for unknown reasons (Qu et al., 1998. All-trans retinoic acid potentiates the ability of interferon beta-1b. β-IFN may also inhibit the induction of inducible nitric oxide synthase (INOS) expression by IL-1 and IFN-γ. Production of nitric oxide by INOS in astrocytes has been implicated as a factor in the parthenogenesis of MS (Hua et al. 1998. Beta interferon prevents nitric oxide/peroxynitrate from damaging the central nervous system.

In one aspect, the present invention includes the use of β-IFN analogs that are therapeutically effective for treating various diseases associated with β-IFN for generating β-IFN/transferrin fusion proteins.

In another aspect, the present invention includes the use of the β-IFN/transferrin fusion protein in the methods described above to inhibit or stimulate various cellular processes and for the treatment and prevention of the various disease and conditions described above. In particular, the β-IFN/transferrin fusion protein may be used to treat multiple sclerosis, herpes, influenza, brain tumor, and skin cancer.

The β-IFN/transferrin fusion protein of the present invention can be formulated into pharmaceutical compositions by well known methods. See, e.g., Remington's Pharmaceutical Sciences by E. W. Martin, hereby incorporated by reference, describes suitable formulations. The pharmaceutical composition of the β-IFN/transferrin fusion protein of the present invention may be formulated in a variety of forms, including liquid, gel, lyophilized, or any other suitable form. The preferred form will depend upon the particular indication being treated and will be apparent to one of skill in the art.

The β-IFN/transferrin fusion protein can be administered in pure form or in an appropriate pharmaceutical composition. Administration can be carried out via any of the accepted modes. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and the β-IFN/transferrin fusion protein as the active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of the β-IFN/transferrin fusion protein, and 99% to 1% by weight of a suitable pharmaceutical excipient. The composition could be about 5% to 75% by weight of the β-IFN/transferrin fusion protein with the rest being suitable pharmaceutical excipients.

The route of administration could be parenterally, using a convenient daily dosage regimen which can be adjusted according to the degree of severity of the disease, preferably multiple sclerosis, to be treated. For such parenteral administration, a pharmaceutically acceptable composition containing the β-IFN/transferrin fusion protein may be formed by the methods disclosed in U.S. Pat. Nos. 4,462,940, 4,588,585 and 4,992,271.

Alternatively, the β-IFN/transferrin fusion protein pharmaceutical compositions may be administered orally, intravenously, intramuscularly, intraperitoneally, intradermally or subcutaneously or in any other acceptable manner. The preferred mode of administration will depend upon the particular indication being treated and will be apparent to one of skill in the art.

U.S. Pat. No. 6,333,032 describes effective methods of using β-IFN to treat diseases in warm-blooded vertebrates, such as multiple sclerosis. Treatment of multiple sclerosis comprises administering β-IFN at a dosage of 0.01 to about 5 IU/lb per day in a dosage form adapted to promote contact of said dosage of interferon with the oral and pharyngeal mucosa of said animal. The dosage of interferon could be from 0.1 to about 4.0 IU/lb per day, or from 0.5 to about 1.5 IU/lb of body weight per day.

The present invention contemplates administering the β-IFN in a dosage form adapted to assure maximum contact of the interferon in said dosage form with the oral and pharyngeal mucosa of the human or animal undergoing treatment. Contact of interferon with the mucosa can be enhanced by maximizing residence time of the treatment solution in the oral or pharyngeal cavity. Thus, best results seem to be achieved in human patients when the patient is requested to hold said solution of interferon in the mouth for a period of time. Contact of interferon with the oral and pharyngeal mucosa and thereafter with the lymphatic system of the treated human or animal is unquestionably the most efficient method administering immunotherapeutic amounts of interferon.

Further, the present invention contemplates the use of the β-IFN/transferrin protein for the manufacture of a medicament which is useful for the treatment of diseases associated with β-IFN. The diseases contemplated by the present invention include but are not limited to those described above.

Glucagon-Like Peptide-1 (GLP-1)

Glucagon-Like Peptide-1 (GLP-1) is a gastrointestinal hormone that regulates insulin secretion belonging to the so-called enteroinsular axis. The enteroinsular axis designates a group of hormones, released from the gastrointestinal mucosa in response to the presence and absorption of nutrients in the gut, which promote an early and potentiated release of insulin. The incretin effect which is the enhancing effect on insulin secretion is probably essential for a normal glucose tolerance. GLP-1 is a physiologically important insulinotropic hormone because it is responsible for the incretin effect.

GLP-1 is a product of proglucagon (Bell, et al., Nature, 1983, 304: 368–371). It is synthesized in intestinal endocrine cells in two principal major molecular forms, as GLP-1(7–36)amide and GLP-1(7–37). The peptide was first identified following the cloning of cDNAs and genes for proglucagon in the early 1980s.

Initial studies done on the full length peptide GLP-1(1–37 and 1–36$^{amide}$) concluded that the larger GLP-1 molecules are devoid of biological activity. In 1987, three independent research groups demonstrated that removal of the first six amino acids resulted in a GLP-1 molecule with enhanced biological activity.

The amino acid sequence of GLP-1 is disclosed by Schmidt et al. (1985 Diabetologia 28 704–707). Human GLP-1 is a 37 amino acid residue peptide originating from preproglucagon which is synthesized in the L-cells in the distal ileum, in the pancreas, and in the brain. Processing of preproglucagon to GLP-1(7–36)amide, GLP-1(7–37) and GLP-2 occurs mainly in the L-cells. The amino acid sequence of GLP-1(7–36) and GLP-1(7–37) is (SEQ ID NO: 6):

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X wherein X is $NH_2$ for GLP-1(7–36) and X is Gly for GLP-1(7–37).

GLP-1 like molecules possesses anti-diabetic activity in human subjects suffering from Type II (non-insulin-dependent diabetes mellitus (NIDDM)) and, in some cases, even Type I diabetes. Treatment with GLP-1 elicits activity, such as increased insulin secretion and biosynthesis, reduced glucagon secretion, delayed gastric emptying, only at elevated glucose levels, and thus provides a potentially much safer therapy than insulin or sulfonylureas. Postprandial and glucose levels in patients can be moved toward normal levels with proper GLP-1 therapy. There are also reports suggesting GLP-1-like molecules possess the ability to preserve and even restore pancreatic beta cell function in Type-II patients.

Any GLP-1 sequence may be used to make Tf fusion proteins of the present invention, including GLP-1(7–35), GLP-1(7–36), and GLP-1(7–37). GLP-1 also has powerful actions on the gastrointestinal tract. Infused in physiological amounts, GLP-1 potently inhibits pentagastrin-induced as well as meal-induced gastric acid secretion (Schjoldager et al., Dig. Dis. Sci. 1989, 35:703–708; Wettergren et al., Dig Dis Sci 1993; 38:665–673). It also inhibits gastric emptying rate and pancreatic enzyme secretion (Wettergren et al., Dig Dis Sci 1993; 38:665–673). Similar inhibitory effects on gastric and pancreatic secretion and motility may be elicited in humans upon perfusion of the ileum with carbohydrate- or lipid-containing solutions (Layer et al., Dig Dis Sci 1995, 40:1074–1082; Layer et al., Digestion 1993, 54: 385–38). Concomitantly, GLP-I secretion is greatly stimulated, and it has been speculated that GLP-1 may be at least partly responsible for this so-called "ileal-brake" effect (Layer et al., Digestion 1993; 54: 385–38). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (Nauck et al., Gut 1995; 37 (suppl. 2): A124).

GLP-1 seems to have an effect on food intake. Intraventricular administration of GLP-1 profoundly inhibits food intake in rats (Schick et al. in Ditschuneit et al. (eds.), Obesity in Europe, John Libbey & Company ltd, 1994; pp. 363–367; Turton et al., Nature 1996, 379: 69–72). This effect seems to be highly specific. Thus, N-terminally extended GLP-1 (PG 72–107) amide is inactive and appropriate doses of the GLP-1 antagonist, exendin 9–39, abolish the effects of GLP-1 (Tang-Christensen et al., Am. J. Physiol., 1996, 271(4 Pt 2):R848–56). Acute, peripheral administration of GLP-1 does not inhibit food intake acutely in rats (Tang-Christensen et al., Am. J. Physiol., 1996, 271(4 Pt 2):R848–56; Turton et al., Nature 1996, 379: 69–72). However, it remains possible that GLP-1 secreted from the intestinal L-cells may also act as a satiety signal.

In diabetic patients, GLP's insulinotropic effects and the effects of GLP-1 on the gastrointestinal tract are preserved (Willms et al, Diabetologia 1994; 37, suppl. 1: A118), which may help curtail meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (Larsen et al., Diabetes 1996; 45, suppl. 2: 233A.).

GLP-1/transferrin fusion proteins comprising at least one analog of GLP-1 and fragments thereof are useful in the treatment of Type 1 and Type 2 diabetes and obesity.

As used herein, the term "GLP-1 molecule" means GLP-1, a GLP-1 analog, or GLP-1 derivative.

As used herein, the term "GLP-1 analog" is defined as a molecule having one or more amino acid substitutions, deletions, inversions, or additions compared with GLP-1. Many GLP-1 analogs are known in the art and include, for example, GLP-1(7–34), GLP-1(7–35), GLP-1(7–36), Val$^8$-GLP-1(7–37), Gln$^9$-GLP1(7–37), D-Gln$^9$-GLP-1(7–37), Thr$^{16}$-Lys$^{18}$-GLP1(1–37), and Lys$^{18}$-GLP-1(7–37). U.S. Pat. No. 5,118,666 discloses examples of GLP-1 analogs such as GLP-1(7–34) and GLP-1(7–35).

The term "GLP-1 derivative" is defined as a molecule having the amino acid sequence of GLP-1 or a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties.

As used herein, the term "GLP-1 related compound" refers to any compound falling within the GLP-1, GLP-1 analog, or GLP-1 derivative definition.

WO 91/11457 discloses analogs of the active GLP-1 peptides 7–34, 7–35, 7–36, and 7–37 which can also be useful as GLP-1 moieties.

EP 0708179-A2 (Eli Lilly & Co.) discloses GLP-1 analogs and derivatives that include an N-terminal imidazole group and optionally an unbranched $C_6$–$C_{10}$ acyl group in attached to the lysine residue in position 34.

EP 0699686-A2 (Eli Lilly & Co.) discloses certain N-terminal truncated fragments of GLP-1 that are reported to be biologically active.

U.S. Pat. No. 5,545,618 discloses GLP-1 molecules consisting essentially of GLP-1(7–34), GLP1(7–35), GLP-1

(7–36), or GLP-1(7–37), or the amide forms thereof, and pharmaceutically-acceptable salts thereof, having at least one modification selected from the group consisting of: (a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36; (b) substitution of an oxidation-resistant amino acid for tryptophan at position 31; (c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

U.S. Pat. No. 5,118,666 discloses a GLP-1 molecule having insulinotropic activity. Such molecule is selected from the group consisting of a peptide having the amino acid sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys (SEQ ID NO: 7) or His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly (SEQ ID NO: 8); and a derivative of said peptide and wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

U.S. Pat. No. 6,277,819 teaches a method of reducing mortality and morbidity after myocardial infarction comprising administering GLP-1, GLP-1 analogs, and GLP-1 derivatives to the patient. The GLP-1 analog being represented by the following structural formula (SEQ ID NO: 9): $R_1$-$X_1$-Glu-Gly-Thr-Phe-Thr-Ser-Asp-Val-Ser-Ser-Tyr-Leu-$X_2$-Gly-Gln-Ala-Ala-Lys-$X_3$-Phe-Ile-Ala-Trp-Leu-Val-Lys-Gly-Arg-$R_2$ and pharmaceutically-acceptable salts thereof, wherein: $R_1$ is selected from the group consisting of L-histidine, D-histidine, desamino-histidine, 2-amino-histidine, .beta.-hydroxy-histidine, homohistidine, alpha-fluoromethyl-histidine, and alpha-methyl-histidine; $X_1$ is selected from the group consisting of Ala, Gly, Val, Thr, Ile, and alpha-methyl-Ala; $X_2$ is selected from the group consisting of Glu, Gln, Ala, Thr, Ser, and Gly; $X_3$ is selected from the group consisting of Glu, Gln, Ala, Thr, Ser, and Gly; $R_2$ is selected from the group consisting of $NH_2$, and Gly-OH; provided that the GLP-1 analog has an isoelectric point in the range from about 6.0 to about 9.0 and further providing that when $R_1$ is His, $X_1$ is Ala, $X_2$ is Glu, and $X_3$ is Glu, $R_2$ must be $NH_2$.

Ritzel et al. (Journal of Endocrinology, 1998, 159: 93–102) disclose a GLP-1 analog, [Ser$^8$]GLP-1, in which the second N-terminal alanine is replaced with serine. The modification did not impair the insulinotropic action of the peptide but produced an analog with increased plasma stability as compared to GLP-1.

U.S. Pat. No. 6,429,197 teaches that GLP-1 treatment after acute stroke or hemorrhage, preferably intravenous administration, can be an ideal treatment because it provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects. The present invention provides a method of treating the ischemic or reperfused brain with GLP-1 or its biologically active analogues after acute stroke or hemorrhage to optimize insulin secretion, to enhance insulin effectiveness by suppressing glucagon antagonism, and to maintain euglycemia or mild hypoglycemia with no risk of severe hypoglycemia.

U.S. Pat. No. 6,277,819 provides a method of reducing mortality and morbidity after myocardial infraction, comprising administering to a patient in need thereof, a compound selected from the group consisting of GLP-1, GLP-1 analogs, GLP-1 derivatives and pharmaceutically-acceptable salts thereof, at a dose effective to normalize blood glucose.

U.S. Pat. No. 6,191,102 discloses a method of reducing body weight in a subject in need of body weight reduction by administering to the subject a composition comprising a glucagon-like peptide-1 (GLP-1), a glucagon-like peptide analog (GLP-1 analog), a glucagon-like peptide derivative (GLP-1 derivative) or a pharmaceutically acceptable salt thereof in a dose sufficient to cause reduction in body weight for a period of time effective to produce weight loss, said time being at least 4 weeks.

GLP-1 is fully active after subcutaneous administration (Ritzel et al., Diabetologia 1995; 38: 720–725), but is rapidly degraded mainly due to degradation by dipeptidyl peptidase IV-like enzymes (Deacon et al., J Clin Endocrinol Metab 1995, 80: 952–957; Deacon et al.,1995, Diabetes 44: 1126–1131). Thus, unfortunately, GLP-1 and many of its analogues have a short plasma half-life in humans (Orskov et al., Diabetes 1993; 42:658–661). Accordingly, it is an objective of the present invention to provide transferrin fusion proteins comprising GLP-1 or analogues thereof which have a protracted profile of action relative to GLP-1 (7–37). It is a further object of the invention to provide derivatives of GLP-1 and analogues thereof which have a lower clearance than GLP-1(7–37). Moreover, it is an object of the invention to provide pharmaceutical compositions comprising GLP-1/transferrin fusion proteins or GLP-1 analog/transferrin fusion proteins with improved stability. Additionally, the present invention includes the use of GLP-1/transferrin fusion proteins or GLP-1 analog/transferrin fusion proteins to treat diseases associated with GLP-1 such as but not limited to those described above.

In one aspect of the present invention, the pharmaceutical compositions comprising the GLP-1 peptide/transferrin fusion proteins and GLP-1 analog/transferrin fusion proteins may be formulated by any of the established methods of formulating pharmaceutical compositions, e.g. as described in Remington's Pharmaceutical Sciences, 1985. The composition may be in a form suited for systemic injection or infusion and may, as such, be formulated with a suitable liquid vehicle such as sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The GLP-1/transferrin fusion proteins and GLP-1 analog/transferrin fusion proteins of the present invention may also be adapted for nasal, transdermal, pulmonal or rectal administration. The pharmaceutically acceptable carrier or diluent employed in the composition may be any conventional solid carrier. Examples of solid carriers are lactose, terra alba, sucrose, talc, gelatin, agar, pectin, acacia, magnesium stearate and stearic acid. Similarly, the carrier or diluent may include any sustained release material known in the art, such as glyceryl monostearate or glyceryl distearate, alone or mixed with a wax.

It may be of particular advantage to provide the composition of the invention in the form of a sustained release formulation. As such, the composition may be formulated as microcapsules or microparticles containing the GLP-1/transferrin fusion protein or GLP-1 analog/transferrin fusion protein encapsulated by or dispersed in a suitable pharmaceutically acceptable biodegradable polymer such as polylactic acid, polyglycolic acid or a lactic acid/glycolic acid copolymer.

For nasal administration, the preparation may contain GLP-1/transferrin fusion proteins or GLP-1 analog/transferrin fusion proteins dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidyleholine) or cyclodextrin, or preservatives such as parabenes.

Generally, the compounds of the present invention are dispensed in unit dosage form comprising 0.5–500 mg of the fusion protein together with a pharmaceutically acceptable carrier per unit dosage.

Moreover, the present invention contemplates the use of the GLP-1/transferrin and GLP-1 analog/transferrin fusion proteins for the manufacture of a medicinal product which can be used in the treatment of diseases associated with elevated glucose level, such as but not to limited to those described above. Specifically, the present invention contemplates the use of GLP-1/transferrin fusion protein for the treatment of diabetes including type II diabetes, obesity, severe burns, and heart failure, including congestive heart failure and acute coronary syndrome.

The N-terminus of GLP-1 is normally amidated. In yeast, amidation does not occur. In one aspect of the invention, in order to compensate for amidation on the N-terminus which does not occur in yeast, an extra amino acid is added on the N-terminus of GLP-1. The addition of an amino acid to the N-terminus of GLP-1 may prevent dipeptidyl peptidase from cleaving at the second amino acid of GLP-1 due to steric hindrance. Therefore, GLP-1 will remain functionally active. Any one of the 20 amino acids may be added to the N-terminus of GLP-1. In some instances, an uncharged or positively charged amino acid may be used and preferably, a smaller amino acid such as Glycine is added. The GLP-1 with the extra amino acid is then fused to transferrin. Accordingly, the GLP-1 with the added amino acid will be fused at the N-terminus of the GLP-1/transferrin fusion protein.

GLP-mTf Fusion Protein for Treating Type 2 Diabetes

As discussed above, GLP-1 activates and regulates important endocrine hormone systems in the body and plays a critical management role in the metabolism of glucose. Unlike all other diabetic treatments on the market GLP-1 has the potential to be restorative by acting as a growth factor for B-cells thus improving the ability of the pancreas to secrete insulin and also, to make the existing insulin levels act more efficiently by improving sensitivity and better stabilizing glucose levels. This reduces the burden on daily monitoring of glucose levels and potentially offers a delay in the serious long term side effects caused by fluctuations in blood glucose due to diabetes. Furthermore, GLP-1 can reduce appetite and reduce weight. Obesity is an inherent consequence of poor control of glucose metabolism and this only serves to aggravate the diabetic condition.

Clinical application of natural GLP-1 is limited because it is rapidly degraded in the circulation (half-life is several minutes). To maintain therapeutic levels in the circulation requires constant administration of high doses using pumps or patch devices which adds to the cost of treatment. This is inconvenient for long term chronic use especially in conjunction with all the other medications for treating diabetes and monitoring of glucose levels. The GLP-1 fusion proteins retain the activity of GLP-1 but have the long half-life (14–17 days), solubility, and biodistribution properties of transferrin (mTf). These properties could provide for a low cost, small volume, monthly s.c. (subcutaneous) injection and this type of product is absolutely needed for long term chronic use.

EPO Mimetic Peptide (EMP)

Erythropoietin (EPO) is a glycoprotein hormone that is synthesized in the kidneys of mammals for stimulating mitotic cell division and differentiation of erythrocyte precursor cells. Accordingly, EPO acts to stimulate and regulate the production of erythrocytes. Because of its role in red blood cell formation, EPO is useful in both the diagnosis and the treatment of blood disorders characterized by low or defective red blood cell production.

Studies have shown the efficacy of EPO therapy in a variety of disease states, disorders, and states of hematologic irregularity, for example, beta-thalassemia (Vedovato et al. (1984) Acta. Haematol. 71:211–213); cystic fibrosis (Vichinsky et al. (1984) J. Pediatric 105:15–21); pregnancy and menstrual disorders (Cotes et al. (1983) Brit. J. Ostet. Gyneacol. 90:304–311); early anemia of prematurity (Haga et al. (1983) Acta Pediatr. Scand. 72:827–831); spinal cord injury (Claus-Walker et al. (1984) Arch. Phys. Med. Rehabil. 65:370–374); space flight (Dunn et al. (1984) Eur. J. Appl. Physiol. 52:178–182); acute blood loss (Miller et al. (1982) Brit. J. Haematol. 52:545–590); aging (Udupa et al. (1984) J. Lab. Clin. Med. 103:574–588); various neoplastic disease states accompanied by abnormal erythropoiesis (Dainiak et al. (1983) Cancer 5:1101–1106); and renal insufficiency (Eschbach et al. (1987) N. Eng. J. Med. 316:73–78). During the last fifteen years, EPO has been used for the treatment of the anemia of renal failure, anemia of chronic disease associated with rheumatoid arthritis, inflammatory bowel disease, AIDS, and cancer, as well as for the treatment of anemia in hematopoietic malignancies, post-bone marrow transplantation, and autologous blood donation.

The activity of EPO is mediated by its receptor. The EPO-receptor (EPO-R) belongs to the class of growthfactor-type receptors which are activated by a ligand-induced protein dimerization. Other hormones and cytokines such as human growth hormone (hGH), granulocyte colony stimulating factor (G-CSF), epidermal growth factor (EGF) and insulin can cross-link two receptors resulting in juxtaposition of two cytoplasmic tails. Many of these dimerization-activated receptors have protein kinase domains within the cytoplasmic tails that phosphorylate the neighboring tail upon dimerization. While some cytoplasmic tails lack intrinsic kinase activity, these function by association with protein kinases. The EPO receptor is of the latter type. In each case, phosphorylation results in the activation of a signaling pathway.

There has been an increasing interest in molecular mimicry with EPO potency. For example, dimerization of the erythropoietin receptor (EPOR) in the presence of either natural EPO or synthetic EPO mimetic peptides (EMPs) is the extracellular event that leads to activation of the receptor and downstream signal transduction events. In general, there is an interest in obtaining mimetics with equivalent potency to EPO.

Wrighton et al (1996, Science, 273:458–463) employed phage display where random peptides are to be exposed on coat proteins of filamentous phage. A library of random peptide-phage was allowed to bind to and subsequently eluted from the extracellular domain of EPO receptor in the screening system. They used weak-binding system to first fish out EPO domain-weak-binding (Kd 10 mM) CRIGPITWVC (SEQ ID NO: 10) as the consensus sequence. Consequently, a 20-amino acid peptide, EMP1, (GGTYSCHFGPLTWVCKPQGG, SEQ ID NO: 11) with an affinity (Kd) of 200 nM, compared to 200 pM for EPO was isolated, the sequence of which does not actually exist in the native EPO. The crystal structure at 2.8 A resolution of a complex of this mimetic agonist peptide with the extracellular domain of EPO receptor revealed that a peptide dimer induces an almost perfect twofold dimerization of the receptor (Livnah et al., 1996 Science, 273 (274): 464–471). This 20-amino acid peptide has a b-sheet structure and is stabilized by the C—C disulfide bond.

The biological activity of EMP1 indicates that EMP1 can act as an EPO mimetic. For example, EMP1 competes with EPO in receptor binding assays to cause cellular proliferation of cell lines engineered to be responsive to EPO (Wrighton et al., 1996, Science, 273:458–463). Both EPO and EMP1 induce a similar cascade of phosphorylation events and cell cycle progression in EPO responsive cells (Wrighton et al., 1996, Science, 273:458–463). Further, EMP1 demonstrates significant erythropoietic effects in mice as monitored by two different in vivo assays of nascent red blood cell production (Wrighton et al., 1996, Science, 273:458–463).

Johnson et al. (1998, Biochemistry, 37:3699–3710) identified the minimal peptide that retained activity in the assays for EPO mimetic action. Using N- and C-terminal deletions, they found that the minimal active peptide is EMP20 having the sequence, YSCHFGPLTWVCK (SEQ ID NO: 12), namely amino acids 4 through 16 of EMP1. They also found Tyr4 and Trp13 of EMP1 are critical for mimetic action.

The present invention provides EMP1/transferrin fusion proteins with increased half-life and pharmaceutical compositions comprising such fusion proteins. The present invention contemplates the use of the fusion protein to treat various diseases and conditions associated with EPO such as but not limited to those described above.

In one embodiment of the present invention, the pharmaceutical compositions comprising the EMP1/transferrin fusion protein and may be formulated by any of the established methods of formulating pharmaceutical compositions, e.g. as described in Remington's Pharmaceutical Sciences, 1985. The composition may be in a form suited for systemic injection or infusion and may, as such, be formulated with a suitable liquid vehicle such as sterile water or an isotonic saline or glucose solution. These pharmaceutical compositions may contain buffers, salts and other excipients to stabilize the composition or assist in the delivery of the transferrin fusion proteins.

In a preferred embodiment, the present invention provides a method for treating disorders associated with EPO. The method is accomplished by administering a EMP1/transferrin fusion protein provided herein for a time and under conditions sufficient to alleviate the symptoms of the disorder, i.e. sufficient to effect dimerization or biological activation of EPO receptors. In the case of EPO such methodology is useful in the treatment of end-stage renal failure/dialysis; anemia, especially associated with AIDS or chronic inflammatory diseases such as rheumatoid arthritis and chronic bowel inflammation; auto-immune disease; and for boosting the red blood cell count of patient when necessary, e.g. prior to surgery or as pretreatment to transfusion. The EMP1/transferrin fusion protein of the present invention which behave as EPO agonists can be used to activate megakaryocytes.

Since EPO has been shown to have a mitogenic and chemotactic effect on vascular endothelial cells as well as an effect on central cholinergic neurons (Amagnostou et al. (1990) Proc. Natl. Acad. Sci. USA 87:597805982; Konishi et al. (1993) Brain Res. 609:29–35), the compounds of this invention can also be used to treat a variety of vascular disorders, such as promoting wound healing, growth of collateral coronary blood vessels (such as those that may occur after myocardial infarction), trauma, and post vascular graft treatment, and a variety of neurological disorders, generally characterized by low absolute levels of acetyl choline or low relative levels of acetyl choline as compared to other neuroactive substances e.g., neurotransmitters.

Accordingly, the present invention includes pharmaceutical compositions comprising, as an active ingredient, the EMP1/transferrin fusion protein of the present invention in association with a pharmaceutical carrier or diluent. The EMP1/transferrin fusion protein of this invention can be administered by oral, parenteral (intramuscular, intraperitoneal, intravenous (IV) or subcutaneous injection), transdermal (either passively or using iontophoresis or electroporation) or transmucosal (nasal, vaginal, rectal, or sublingual) routes of administration in dosage forms appropriate for each route of administration.

Solid dosage forms for oral administration include capsules, tablets, pill, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals.

Moreover, the present invention also contemplates the use of the transferrin fusion protein comprising EMP 1 or analogs thereof for the manufacture of a medicinal product which can be used in the treatment of diseases associated with low or defective red blood cell production. Examples of such diseases are not limited to those described above.

T-20 and T-1249

HIV infection is pandemic and HIV associated diseases represent a major world health problem. Although considerable effort is being put into the successful design of effective therapeutics, currently no curative anti-retroviral drugs against AIDS exist. In attempts to develop such drugs, several stages of the HIV life cycle have been considered as targets for therapeutic intervention (Mitsuya, H. et al., 1991, FASEB J. 5:2369–2381). For example, virally encoded reverse transcriptase has been one focus of drug development. A number of reverse-transcriptase-targeted drugs, including 2',3'-dideoxynucleoside analogs such as AZT, ddI, ddc, and d4T have been developed which have been shown to been active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often exhibit toxic side effects, such as bone marrow suppression, vomiting, and liver function abnormalities.

Entry inhibitors are distinct from the existing classes of drugs that fight HIV. Other drugs work inside the infected cell. Nucleoside reverse transcriptase inhibitors such as AZT and abacavir and non-nucleoside reverse transcriptase inhibitors like nevirapine and efavirenz all act by shutting down the reverse transcriptase enzyme that HIV uses to replicate itself once it is inside the cell. Protease inhibitors shut down the viral protease enzyme HIV uses to package itself up for export. By contrast, entry inhibitors are drugs that interfere with the processes involved in the virus' initial assault on the cell's outer membrane.

T-20 is the most studied of all the entry inhibitors and is the first member of the fusion inhibitor class. Unlike existing AIDS drugs that work inside the cell and target viral enzymes involved in the replication of the virus, T-20 inhibits fusion of HIV with host cells before the virus enters the cell and begins its replication process. T-20 binds to one of the two helical domains of gp41. Gp41 is a spring-loaded HIV-1 protein that is activated when CD4 binds to HIV gp-120. The fusion action of gp41 is inhibited if its two helical domains cannot fold together. T-20 binds to gp41, effectively keeping the protein from functioning. It has been shown in early, single-arm clinical studies to be about as potent as a protease inhibitor by itself-giving greater than 10 fold reductions in viral load-and to be safe in combination with other antiretrovirals.

U.S. Pat. No. 5,464,933 discloses T-20 (pentafuside, DP-178) as a 36 amino acid synthetic peptide. Since this drug is a peptide, it cannot be given orally because it is readily broken down by the digestive system. When administered by subcutaneous injection, T-20 achieves sufficient levels in the blood to have anti-HIV activity. It is administered by subcutaneous injection twice daily. However, patients develop skin reactions at the injection site. The most frequently reported treatment related adverse events were mild to moderate local injection site reactions. These consist of mild pain, temporary swelling and redness at the site of injection.

U.S. Pat. No. 6,479,055 discloses peptide analogs of the DP-178 (peptides corresponding to amino acid residues 638 to 673 of transmembrane protein gp41 of HIV-$1_{LAI}$, which exhibit anti-membrane fusion capability, antiviral activity, such as the ability to inhibit HIV transmission to uninfected CD-$4^+$ cells, or an ability to modulate intracellular processes involving coiled-coil peptide structures. Further, the patent relates to the use of DP-178 and DP-178 portions and/or analogs as antifusogenic or antiviral compounds or as inhibitors of intracellular events involving coiled-coil peptide structures. Further, the patent teaches the use of the peptides as diagnostic agents. For example, a DP 178 peptide may be used as an HIV subtype-specific diagnostic.

T-1249 is a sister compound of T-20. Like T-20, T-1249 targets the HIV glycoprotein known as gp41 which HIV uses to bind onto CD4 cells. T-1249 has shown potent anti-HIV effects in animal and laboratory studies. Preliminary safety, dosing and efficacy studies in humans have provided support for ongoing research.

T-1249 is currently administered by subcutaneous (under the skin) injection once or twice daily. The first safety study of T-1249 conducted in humans found two serious adverse events: hypersensitivity reaction (oral ulcers, maculopapular rash, fever) and severe neutropenia. Forty percent of recipients developed injection site reactions but these were deemed to be mild. Dizziness, diarrhea, headache and fever have also been reported by recipients. No dose-limiting toxicity was identified and experiments with higher doses are likely.

T-1249 has completed phase I/II safety and dosing studies. Initial results indicated that higher doses produced an average viral load drop of 1.3 log.

Dose-dependent decreases in HIV RNA have been reported. In the study of T-1249, the average reduction from baseline ranged from 0.29 to 1.96 log copies/ml (Gulick 2002).

The present invention provides transferrin fusion proteins comprising T-20, T-1249, or analogs thereof with increased half-life and pharmaceutical compositions comprising such fusion proteins. The present invention also provides pharmaceutical compositions comprising these transferrin fusion proteins for therapeutic purposes. The present invention contemplates the use of such fusion proteins as inhibitors of human and non-human retroviral, especially HIV, transmission to uninfected cells. The human retroviruses whose transmission may be inhibited by the peptides of the invention include, but are not limited to all strains of HIV-1 and HIV-2 and the human T-lymphocyte viruses (HTLV-I, II, III). The non-human retroviruses whose transmission may be inhibited by the peptides of the invention include, but are not limited to bovine leukosis virus, feline sarcoma and leukemia viruses, simian sarcoma and leukemia viruses, and sheep progress pneumonia viruses.

With respect to HIV, the transferrin fusion protein of the present invention comprising T-20, T-1249 or analogs thereof may be used as a therapeutic in the treatment of AIDS. These transferrin fusion proteins may be administered using techniques well known to those in the art. Preferably, the pharmaceutical compositions comprising these transferrin fusion proteins are formulated and administered systemically. Techniques for formulation and administration may be found in "Remington's Pharmaceutical Sciences" 18th ed., 1990 Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the transferrin fusion proteins comprising T-20, T1249, or analogs thereof may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In addition, the transferrin fusion protein comprising T-20, T1249, or analogs thereof may be used as a prophylactic measure in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The transferrin fusion proteins of the present invention comprising T-20, T-1249, or analogs thereof in such cases may serve the role of a prophylactic vaccine, wherein the host raises antibodies against the fusion proteins of the invention, which then serve to neutralize HIV viruses by, for example, inhibiting further HIV infection. Administration of the transferrin fusion proteins of the invention as a prophylactic vaccine, therefore, would comprise administering to a host a concentration of transferrin fusion protein effective in raising an immune response which is sufficient to neutralize HIV, by, for example, inhibiting HIV ability to infect cells. The exact concentration will depend upon the specific peptide in the transferrin fusion protein to be administered, but may be determined by using standard techniques for assaying the development of an immune response which are well known to those of ordinary skill in the art. The transferrin fusion protein to be used as vaccines are usually administered intramuscularly.

Effective dosages of the transferrin fusion proteins comprising T-20, T-1249, or analogs thereof to be administered may be determined through procedures well known to those in the art which address such parameters as biological half-life, bioavailability, and toxicity. Given the data presented below in Section 6, DP-178, for example, may prove efficacious in vivo at doses required achieve circulating levels of 10 ng per ml of peptide.

Furthermore, the present invention contemplates the use of the transferrin fusion proteins comprising T-20, T-1249, or analogs thereof for the manufacture of a medicinal product for the treatment of diseases associated with the transmission of a virus.

Soluble Toxin Receptors

The present invention provides fusion proteins comprising soluble toxin receptor and transferrin or modified transfentin. As used herein, the term "toxin" refers to a poisonous substance of biological origin. The fusion proteins comprising a soluble toxin receptor may be used to treat patients suffering from diseases associated with toxins. Such fusion proteins may also be used for diagnostic purposes.

Examples of toxins include, but are not limited to, Pseudomonas exotoxins (PE), Diphtheria toxins (DT), ricin toxin, abrin toxin, anthrax toxins, shiga toxin, botulism toxin, tetanus toxin, cholera toxin, maitotoxin, palytoxin, ciguatoxin, textilotoxin, batrachotoxin, alpha conotoxin, taipoxin, tetrodotoxin, alpha tityustoxin, saxitoxin, anatoxin, microcystin, aconitine, exfoliatin toxins A and B, enterotoxins, toxic shock syndrome toxin (TSST-1), Y pestis toxin, gas gangrene toxin, and others. Because of the seriousness of the diseases that some of these toxins cause and the ease of obtaining some of them for biological warfare, there is a need to develop methods to obtain large quantities of potent anti-toxins at a low cost.

The present invention contemplates the use of soluble toxin receptors as anti-toxins for treatment and prevention of diseases associated with various toxins. Toxin receptors are molecules that bind to a specific toxin. A soluble toxin receptor is one that is capable of being dissolved. Usually peptides or fragments of a receptor are soluble. The present invention is directed to soluble peptides or fragments of a toxin receptor that bind a specific toxin.

Similar to other peptides discussed above, these peptides have a short half-life. The present invention provides fusion proteins comprising a soluble peptide of a toxin receptor fused to a transferrin or modified transferrin molecule. The resulting fusion protein has an increased half-life as compared to the soluble toxin receptor peptide. The fusion protein is also easy to produce in large quantities by recombinant means. Since the binding properties of the soluble peptide has not been altered, it will bind the toxin in circulation and prevent the toxin from binding to the target receptor, thus inactivating the toxin. Accordingly, the fusion protein is a potent anti-toxin.

In one embodiment, the present invention provides pharmaceutical composition comprising soluble toxin receptor fused to transferrin or modified transferrin and a pharmaceutically acceptable carrier. In another embodiment, the present invention provides the use of transferrin fusion protein comprising soluble toxin receptor for the manufacture of a medicament for the treatment or prevention of diseases or conditions associated with a toxin.

Unlike antibodies which are difficult and expensive to produce in large quantities, the present transferrin/anti-toxin fusion protein is highly potent and less costly to manufacture. Additionally, immunization is not expected to maintain the antibody titers required to protect in instances of mass exposure following an act of bioterrorism. It is unrealistic for the population to be immunized on a mass scale in anticipation of an exposure.

*Bacillus Anthracis* Toxin Receptor

Anthrax toxin is a well-known agent of biological warfare derived from *Bacillus anthracis*. *Bacillus anthracis* produces three proteins which when combined appropriately form two potent toxins, collectively designated anthrax toxin. Protective antigen (PA, 82,684 Da (Dalton)) and edema factor (EF, 89,840 Da) combine to form edema toxin (ET), while PA and lethal factor (LF, 90,237 Da) combine to form lethal toxin (LT) (Leppla, S. H. Alouf, J. E. and Freer, J. H., eds. Academic Press, London 277–302, 1991). ET and LT each conform to the AB toxin model, with PA providing the target cell binding (B) function and EF or LF acting as the effector or catalytic (A) moieties. A unique feature of these toxins is that LF and EF have no toxicity in the absence of PA, apparently because they cannot gain access to the cytosol of eukaryotic cells.

Recently, two of the targets of Lethal factor (LF) were identified in cells. LF is a metalloprotease that specifically cleaves Mek1 and Mek2 proteins, kinases that are part of the MAP-kinase signaling pathway. LF's proteolytic activity inactivates the MAP-kinase signaling cascade through cleavage of mitogen activated protein kinase kinases 1 or 2 (MEK1 or MEK2). (Leppla, S. A. In The Comprehensive Sourcebook of Bacterial Protein Toxins. J. E. Alouf and J. H. Freer, Eds. $2^{nd}$ edition, San Diego, Academic Press, 1999; pp 243–263.).

PA is capable of binding to the surface of many types of cells. After PA binds to a specific receptor (Leppla, supra, 1991) on the surface of susceptible cells, it is cleaved at a single site by a cell surface protease, probably furin, to produce an amino-terminal 19-kDa fragment that is released from the receptor/PA complex (Singh et al., J. Biol. Chem. 264:19103–19107, 1989). Removal of this fragment from PA exposes a high-affinity binding site for LF and EF on the receptor-bound 63-kDa carboxyl-terminal fragment (PA63). The complex of PA63 and LF or EF enters cells and probably passes through acidified endosomes to reach the cytosol.

PA, the non-toxic, cell-binding component of the toxin, is the essential component of the currently available human vaccine. The vaccine is usually produced from batch cultures of the Sterne strain of *B. anthracis*, which although avirulent, is still required to be handled as a Class III pathogen. In addition to PA, the vaccine contains small amounts of the anthrax toxin moieties, edema factor and lethal factor, and a range of culture derived proteins. All these factors contribute to the recorded reactogenicity of the vaccine in some individuals. The vaccine is expensive and requires a six month course of four vaccinations. Futhermore, present evidence suggests that this vaccine may not be effective against inhalation challenge with certain strains (M. G. Broster et al., Proceedings of the International Workshop on Anthrax, Apr. 11–13, 1989, Winchester UK. Salisbury med Bull Suppl No 68, (1990) 91–92).

Bradley et al. (Nature, 2001, 414: 225–229) disclose cloning of the human anthrax receptor that binds to PA. The receptor, ATR (anthrax toxin receptor) is a type I membrane protein consisting of 368 amino acids. The protein has a predicted signal peptide of 27 amino acids, an extracellular domain of 293 amino acids containing three putative N-linked glycosylation sites, a putative transmembrane region of 23 amino acids and a short cytoplasmic tail of 25 amino acids. A notable feature of ATR is that the extracellular domain consists of a von willebrand factor type A (VWA) domain which is known to be important in protein-protein interactions. This VWA domain is located at amino acids 44 to 216. A soluble version of ATR comprising amino acids 41–227 was shown to bind the anthrax toxin. Accordingly, the VWA domain of ATR binds directly to PA.

The present invention provides an anthrax antitoxin comprising the extracellular domain of ATR fused to transferrin or modified transferrin molecule. The present invention also contemplates fusion proteins comprising fragments thereof of the extracellular domain of ATR that binds PA fused to transferrin or modified transferrin molecule. Moreover, the present invention contemplates fusion proteins comprising small molecule mimetics of the extracellular domain of ATR that binds PA fused to transferrin or modified transferrin molecule. Preferably, the present invention provides amino acids 41–227 of ATR fused to transferrin or modified transferrin molecule.

*Clostridium Botulinum* Toxin

The clostridial neurotoxins are the most poisonous substance. Humans are exposed to the neurotoxin produced by *Clostridium tetani* (tetanus toxin) as a result of wounds. Although the tetanus toxin remains a serious public health problem in developing countries around the world, nearly everyone in the western world is protected from tetanus toxin as a consequence of childhood immunizations. Humans usually come into contact with the neurotoxin produced by *Clostridium botulinum* (botulinum toxin) through food poisoning. However, there are rare incidents of wound botulism and colonizing infection of neonates known as infant botulism. Since botulinum poisoning is rare, immunization of the general population is not warranted on the basis of cost and the expected rates of adverse reaction to the vaccine. Therefore, humans are not protected from botulinum toxins. Additionally, these toxins are relatively to produce. Consequently, botulinum toxins are likely biological warfare agents.

As discussed, the anaerobic, gram positive bacterium *Clostridium botulinum* produces the most poisonous biological neurotoxin known with a lethal human dose in the nanogram range. The effect of the toxin ranges from diarrheal diseases that can cause destruction of the colon, to paralytic effects that can cause death. The spores of *Clostridium botulinum* are found in soil and can grow in improperly sterilized and sealed food containers of home based canneries, which are the cause of many of the cases of botulism. The symptoms of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulism disease may be grouped into four types, based on the method of introduction of toxin into the bloodstream. Food-borne botulism results from ingesting improperly preserved and inadequately heated food that contains botulinal toxin (i.e., the toxin is pre-formed prior to ingestion). Wound-induced botulism results from *C. botulinum* penetrating traumatized tissue and producing toxin that is absorbed into the bloodstream. Since 1950, thirty cases of wound botulism have been reported (Swartz, "Anaerobic Spore-Forming Bacilli: The Clostridia," pp. 633–646, in Davis et al., (eds.), Microbiology, 4th edition, J. B. Lippincott Co. (1990)). Inhalation botulism results when the toxin is inhaled. Inhalation botulism has been reported as the result of accidental exposure in the laboratory (Holzer, Med. Kiln., 41:1735 [1962]) and is a potential danger if the toxin is used as an agent of biological warfare (Franz et al., in Botulinum and Tetanus Neurotoxins, DasGupta (ed.), Plenum Press, New York [1993], pp. 473–476). Infectious infant botulism results from *C. Botulinum* colonization of the infant intestine with production of toxin and its absorption into the bloodstream.

Different strains of *Clostridium botulinum* each produce antigenically distinct toxin designated by the letters A-G. Serotype A toxin has been implicated in 26% of the cases of food botulism; types B, E, and F have also been implicated in a smaller percentage of the food botulism cases (Sugiyama, Microbiol. Rev., 44:419 (1980)). Wound botulism has been reportedly caused by only types A or B toxins (Sugiyama, supra). Nearly all cases of infant botulism have been caused by bacteria producing either type A or type B toxin (exceptionally, one New Mexico case was caused by *Clostridium botulinum* producing type F toxin and another by *Clostridium botulinum* producing a type B-type F hybrid) (Arnon, Epidemiol. Rev., 3:45 (1981)). Type C toxin affects waterfowl, cattle, horses and mink. Type D toxin affects cattle, and type E toxin affects both humans and birds.

*Clostridium botulinum* neurotoxin acts on nerve endings to block acetylcholine release. Binding of the neurotoxin to a membrane receptor through its heavy chain is the first essential step in its mode of toxin action. Li et al. (J Nat Toxins 1998, 7(3):215–26) purified Type E botulinum neurotoxin (BoNT/E) or type A botulinum neurotoxin (BoNT/A) from rat brain synaptosomes employing a neurotoxin affinity column chromatography. The protein fraction eluted from the affinity column with 0.5 M NaCl contained a 57 kDa protein as a major eluant. Immunoblotting the eluant with anti-synaptotagmin antibodies revealed that the 57 kDa protein was synaptotagmin I. Rat synaptotagmin I has been suggested as the receptor for BoNT/B (Nishiki et al., J. Biol. Chem. 269, 10498–10503, 1994) in rat brain. Li et al. investigated the binding of BoNT/A and BoNT/E to synaptotagmin I by a microtiter plate-based method. Binding of synaptotagmin I to BoNT/A coated on the plate was competitively reduced upon preincubation of the proteins with BoNT/E, suggesting a competitive binding of BoNT/A and BoNT/E to the receptor. Taken together, these results suggest that the same receptor protein binds to all three BoNT serotypes tested.

Synaptotagmin I is a broad acting receptor of *Clostridium botulinum* neurotoxin serotypes A, B, and E and possibly C, D, F, and G. It is located on the motor neuronal cell. The N-terminal fragment of synaptotagmin I, amino acids 1–53 (SEQ ID NO: 4), is responsible for binding to the various neurotoxin serotypes. The binding mediates translocation of the neurotoxin into the cell and blocks neurotransmitter release which results in paralysis and in extreme cases fatality. The N-terminal fragment may be produced by recombinant means and used to bind neurotoxins in circulation. The binding of the fragment to the neurotoxin prevents the neurotoxin from binding its target receptor which results in neutralization of the toxin.

The goal of the present invention is to provide an anti-toxin of *Clostridium botulinum* with significantly increased half-life as compared to the recombinantly produced 53 amino acid fragment, so that the anti-toxin has sufficient time to find and bind the neurotoxins as they enter the circulation. The present invention provides a fusion protein comprising the N-terminal 53 amino acid fragment of synaptotagmin I fused to transferrin or modified transferrin, thereby increasing the half-life of the fragment without altering the binding properties of the fragment. Alternatively, the fragment could be chemically pegylated to prolong circulating life. The longer half-life of the anti-toxin will make a given dose more effective. Unlike antibodies, the present anti-toxin fusion protein is broad acting and bind to several neurotoxin serotypes, specifically neurotoxin A, B, and E.

In a preferred embodiment, the fusion protein is produced in a highly efficient microbial production system which can provide large quantities of the anti-toxin at a reasonable cost to treat the population following mass exposure in acts of bioterrorism. This fusion protein can also be used in a prophylactic mode prior to exposure The present invention also contemplates anti-toxins comprising peptide fragments of amino acids 1–53 of synaptotagmin I or small molecule mimetics of amino acids 1–53 of snynaptotagmin I fused to transferrin or modified transferrin molecule.

The fusion protein can also be used to block botulism spread through food or air contamination among the civilian population.

In one aspect of the invention, the anti-toxin fusion protein is used to treat wound botulism resulting from drug use and accidental overdose of botulinum neurotoxin following the treatment of various diseases such as migraine dystonia, and hyperhidrosis.

In another aspect of the invention, the anti-toxin fusion protein is used to treat botulism from food poisoning.

*Diptheria Toxin* Receptor

Diphtheria is caused by a bacterium, *Corynebacterium diphtheriae*, which typically infects mucous membranes: the nose and throat are favorite places for the infection to take hold, but mucous membranes of the eyes or genitalia can be infected also. The bacteria produce a toxin which causes damage to tissue both at the site of the original infection and in other parts of the body once the toxin is spread via the bloodstream. The most serious effects of diphtheria toxin are on the heart (muscle damage leading to loss of pumping ability), kidneys, and the nervous system.

Diphtheria can be treated by giving penicillin or other antibiotics to kill the bacteria, and antitoxin to clear free toxin in the body. However the antitoxin will not clear toxin that has already bound to cells and started to damage them. The better approach is to give toxoid to stimulate immunity to the toxin, thus enabling the body to clear toxin as soon as it appears. Immunity to a bacterial toxin such as diphtheria toxin (DT) may be acquired naturally during the course of an infection, or artificially by injection of a detoxified form of the toxin (i.e., a toxoid) (Germanier, ed., Bacterial Vaccines, Academic Press, Orlando, Fla., 1984). Toxoids have traditionally been prepared by chemical modification of native toxins (e.g., with formalin or formaldehyde (Lingood et al., Brit. J. Exp. Path. 44:177, 1963)), rendering them nontoxic while retaining an antigenicity that protects the vaccinated animal against subsequent challenges by the natural toxin: an example of a chemically-inactivated DT is that described by Michel and Dirkx (Biochem. Biophys. Acta 491:286–295, 1977), in which Trp-153 of Fragment A is the modified residue. The toxoid is given initially at ages 2, 4, and 6 months, again at ages 18 months and 5 years, and regularly every 10 years after that.

Several years it appeared that diptheria was no longer a major public health threat. However, recently, there has been a resurgence of diphtheria in the New Independent States of the former Soviet Union, Ecuador, Thailand, Algeria and other countries. Although diphtheria patients have been treated with equine antitoxin, which neutralizes unbound toxin, surviving patients have often developed serum sickness, an immune complex-type disease. Thus, there is a need to develop a better treatment for diphtheria patients.

The DT molecule is produced as a single polypeptide of 535 amino acids that is readily spliced to form two subunits linked by a disulfide bond, Fragment A (N-terminal of about 21 Kda) and Fragment B (C-terminal of about 37 Kda), as a result of cleavage at residue 190, 192, or 193 (Moskaug, et al., Biol Chem 264:15709–15713, 1989; Collier et al., Biol Chem, 246:1496–1503, 1971). Fragment A is the catalytically active portion of DT. It is an NAD-dependent ADP-ribosyltransferase which specifically targets a protein synthesis factor termed elongation factor 2 (EF-2), thereby inactivating EF2 and shutting down protein synthesis in the cell. Fragment A consists of the diphtheria toxin C domain. Fragment A is linked to the diphtheria toxin Fragment B by a polypeptide loop. Fragment B of DT possesses a receptor-binding domain (the R domain) which recognizes and binds the toxin molecule to a particular receptor structure found on the surfaces of many types of mammalian cells. Once DT is bound to the cell via this receptor structure, the receptor/DT complex is taken up by the cell via receptor-mediated endocytosis. A second functional region on Fragment B (the T domain) acts to translocate DT across the membrane of the endocytic vesicle, releasing catalytically active Fragment A into the cytosol of the cell. A single molecule of Fragment A is sufficient to inactivate the protein synthesis machinery in a given cell.

Naglich et al. (Cell, 1992, 69: 1051–1061) describe expression cloning of diphtheria toxin receptor from highly toxin-sensitive monkey Vero cells. The amino acid sequence of the receptor was found to be identical to that of the cell surface-expressed heparin-binding epidermal growth factor-like growth factor (HB-EGF) precursor (proHB-EGF). Although proHB-EGF is cleaved and released as soluble mature HB-EGF (Goishi et al., Mol. Biol. Cell, 1995, 6:967–980), a significant amount of proHB-EGF remains on the cell surface and functions as a juxtacrine growth factor (Hagashiyama et al., Science, 251: 929–938) and as a DT receptor (Iwamoto et al., EMBO J., 1994, 13:2322–2330; Naglich et al., Cell, 1992, 69: 1051–1061).

Hooper et al. (Biochem. Biophys. Res. Commun., 1995, 206: 710–717) show that recombinant mature human HB-EGF consisting of residues 63–148 (the extracellular domain or the mature growth factor) strongly inhibits the binding of radiolabeled DT to toxin receptor-bearing cells. This result suggests that it would be possible to treat diphtheria patients with mature HB-EGF, a natural growth factor which will not cause serum sickness. However, mature HB-EGF might produce side effects due to its growth factor activity.

Cha et al. (Infection and Immunity, 2002, 70(5): 2344–2350) developed a treatment based on human DT receptor/HB-EGF precursor. They teach a recombinant truncated HB-EGF, consisting of residues 106–149 and lacking most of the heparin binding domain, capable of inhibiting binding of radioiodinated DT to cells. Moreover, they showed that it was a more effective inhibitor of DT binding than the recombinant mature HB-EGF. Further the investigators mutated some residues in the EGF like domain of the recombinant truncated HB-EGF to destroy some of its mitogenic effect. It was demonstrated that the receptor analog (I117A/L148A) displayed a low mitogenic effect. The truncated (I117A/L148A) HB-EGF protein retained high DT binding affinity. The work of Cha et al. suggest that truncated (I117A/L148A) HB-EGF protein could be a safe anti-toxin for EGF receptor.

The present invention provides anti-toxin fusion protein comprising truncated (I117A/L148A) HB-EGF protein fused to transferrin or modified transferrin. The present invention also provides transferrin/anti-toxin fusion proteins comprising fragments thereof of truncated (I117A/L148A) HB-EGF protein that bind DT and has minimal mitogenic activity. Additionally, the invention provides transferrin/anti-toxin fusion proteins comprising analogs of truncated HB-EGF protein that bind DT and has minimal mitogenic activity.

Other Toxin Receptors

Bacterium *Bacillus thuringiensis* (BT) produces bacteriocidal proteins that are toxic to a limited range of insects, mostly in the orders Lepidoptera, Coleoptera and Diptera. Bt toxins have been used to control pests, by applying *Bacillus thuringiensis* to plants or transforming plants themselves so that they generate the toxins by virtue of their transgenic character. The toxins themselves are glycoprotein products of the cry gene as described by Hofte, H. et al. Microbiol Rev (1989) 53:242. U.S. Pat. No. 5,693,491 discloses the cDNA encoding a glycoprotein receptor from the tobacco hormworm that binds a *Bacillus thuringiensis* toxin. The availability of this cDNA permits the retrieval of DNAs encoding homologous receptors in other insects and organisms as well as the design of assays for the cytotoxicity and binding affinity of potential pesticides and the development of methods to manipulate natural and/or introduced homologous receptors and, thus, to destroy target cells, tissues and/or organisms.

Most *Vibrio cholerae* vaccine candidates constructed by deleting the ctxA gene encoding cholera toxin (CT) are able to elicit high antibody responses, but more than one-half of the vaccines still develop mild diarrhea (Levine et al., Infect. Immun., 56(1):161–167 (1988)). Given the magnitude of the diarrhea induced in the absence of CT, it was hypothesized that *V. cholerae* produce other enterotoxigenic factors, which are still present in strains deleted of the ctxA sequence (Levine et al., supra). As a result, a second toxin, zonula occludens toxin (hereinafter "ZOT") elaborated by *V. cholerae*, and which contribute to the residual diarrhea, was discovered (Fasano et al., Proc. Nat. Acad. Sci., USA, 8:5242–5246 (1991)). The zot gene is located immediately adjacent to the ctx genes. The high percent concurrence of the zot gene with the ctx genes among *V. cholerae* strains (Johnson et al., J. Clin. Microb., 31/3:732–733 (1993); and Karasawa et al, FEBS Microbiology Letters, 106:143–146 (1993)) suggests a possible synergistic role of ZOT in the causation of acute dehydrating diarrhea typical of cholera. The zot gene has also been identified in other enteric pathogens (Tschape, 2nd Asian-Pacific Symposium on Typhoid fever and other *Salomellosis*, 47(Abstr.) (1994)). U.S. Pat. No. 5,864,014 discloses the purified receptor for zonula occludens toxin.

Diarrhea can be caused by small, heat stable peptide toxins (ST) produced by various pathogenic bacteria (Thompson, M. R., 1987, Pathol. Immunopathol. Res. 6, 103–116). In developing countries, such toxins may be responsible for 50% to 80% of the reported cases of diarrhea (Giannella, R. A., 1981, Ann. Rev. Med. 32, 341–357). ST are also a major cause of diarrhea in laboratory and domestic animals (Burgess et al., 1978, Infect. Immun. 21, 526–531). It has been shown that heat stable enterotoxins bind to a cell surface receptor in the intestine which subsequently leads to an activation of guanylyl cyclase (Field et al., 1978, Proc. Natl. Acad. Sci. USA 75, 2800–2804; Guerrant et al., 1980, J. Infectios Diseases 142, 220–228). The rise in cyclic GMP then stimulates fluid secretion thereby causing diarrhea. It has been reported that the ST receptor is a distinctly different protein than quanylyl cyclase based on partial chromatographic separation of a detergent-solubilized ST-binding protein from guanylyl cyclase activity (Kuno et al., 1986, J.

Biol. Chem. 261, 1470–1476; Waldman, et al., 1986, Infect. Immun. 51, 320–326). U.S. Pat. No. 5,237,051 discloses cloning of the nucleic acid encoding the intestinal receptor which recognizes heat stable enterotoxins and has guanylyl cylase activity. Data shows that the receptor binds enterotoxin and signals normally through the cyclic GMP second messenger system.

Sepsis is most commonly caused by infection or trauma induced by a toxin. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure. Sepsis-inducing toxins have been found associated with pathogenic bacteria, viruses, plants and venoms. Among the well described bacterial toxins are the endotoxins or lipopolysaccharides (LPS) of the gram-negative bacteria. These molecules are glycolipids that are ubiquitous in the outer membrane of all gram-negative bacteria. It has been reported that report that membrane-fixed CD14 acts as a receptor for the protein-bound endotoxin (LPS) complex and mediates the cellular effects of endotoxin (Wright et al., 1990, Science, 249: 1431). Soluble CD14 truncated at amino acid 71(N71) contains the lipolysaccharide binding sequence. N71 has been shown to neutralize circulating LPS, i.e., acting as an endotoxin antagonist (Higuchi et al., Pathobiology, 2002, 70: 103).

Methods of Delivering Antitoxin Fusion Protein

In one embodiment, the anti-toxin fusion proteins of the present invention will be packaged in a single piston syringe with two contiguous chambers. The first chamber will contain diluent and the second will contain the lyophilized anti-toxin fusion protein. As the plunger is pushed down the diluent will be driven into the next chamber to dissolve the anti-toxin fusion protein which will be expelled through a needle for direct intramuscular delivery. The diluent can contain an anti-freeze such glycerol to act in freezing conditions. The lyophilized product will remain stable in tropical conditions.

The present invention contemplates deliverying the anti-toxin fusion proteins of the present invention in this manner to soldiers entering into a combat situation where the risk of exposure to toxins is high. The anti-toxin fusion protein can be used for immediate treatment on the battlefied and as a prophylactic before going on the battlefield.

Nucleic Acids

The present invention also provides nucleic acid molecules encoding transferrin fusion proteins comprising a transferrin protein or a portion of a transferrin protein covalently linked or joined to a therapeutic protein, preferably a therapeutic protein. As discussed in more detail below, any therapeutic protein may be used. The fusion protein may further comprise a linker region, for instance a linker less than about 50, 40, 30, 20, or 10 amino acid residues. The linker can be covalently linked to and between the transferrin protein or portion thereof and the therapeutic protein, preferably the therapeutic protein. Nucleic acid molecules of the invention may be purified or not.

Host cells and vectors for replicating the nucleic acid molecules and for expressing the encoded fusion proteins are also provided. Any vectors or host cells may be used, whether prokaryotic or eukaryotic, but eukaryotic expression systems, in particular yeast expression systems, may be preferred. Many vectors and host cells are known in the art for such purposes. It is well within the skill of the art to select an appropriate set for the desired application.

DNA sequences encoding transferrin, portions of transferrin and therapeutic proteins of interest may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA or protein sequences (see, for example, Baldwin, G. S. (1993) Comparison of Transferrin Sequences from Different Species. Comp. Biochem. Physiol. 106B/1:203–218 and all references cited therein, which are hereby incorporated by reference in their entirety). Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

As known in the art "similarity" between two polynucleotides or polypeptides is determined by comparing the nucleotide or amino acid sequence and its conserved nucleotide or amino acid substitutes of one polynucleotide or polypeptide to the sequence of a second polynucleotide or polypeptide. Also known in the art is "identity" which means the degree of sequence relatedness between two polypeptide or two polynucleotide sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity or similarity between two sequences include, but are not limited to those disclosed in Guide to Huge Computers, Martin J. Bishop, ed., Academic Press, San Diego, 1994, and Carillo, H., and Lipman, D., SIAM J. Applied Math. 48:1073 (1988).

Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., Nucleic Acids Research 12(1):387 (1984)), BLASTP, BLASTN, FASTA (Atschul, et al., J. Molec. Biol. 215:403 (1990)). The degree of similarity or identity referred to above is determined as the degree of identity between the two sequences indicating a derivation of the first sequence from the second. The degree of identity between two nucleic acid sequences may be determined by means of computer programs known in the art such as GAP provided in the GCG program package (Needleman and Wunsch (1970) Journal of Molecular Biology 48:443–453). For purposes of determining the degree of identity between two nucleic acid sequences for the present invention, GAP is used with the following settings: GAP creation penalty of 5.0 and GAP extension penalty of 0.3.

Codon Optimization

The degeneracy of the genetic code permits variations of the nucleotide sequence of a transferrin protein and/or therapeutic protein of interest, while still producing a polypeptide having the identical amino acid sequence as the polypeptide encoded by the native DNA sequence. The procedure, known as "codon optimization" (described in U.S. Pat. No. 5,547,871 which is incorporated herein by reference in its entirety) provides one with a means of designing such an altered DNA sequence. The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. In particular, available methods may be used to alter the codons encoding a given fusion protein with those most readily recognized by yeast when yeast expression systems are used.

The degeneracy of the genetic code permits the same amino acid sequence to be encoded and translated in many different ways. For example, leucine, serine and arginine are each encoded by six different codons, while valine, proline, threonine, alanine and glycine are each encoded by four different codons. However, the frequency of use of such synonymous codons varies from genome to genome among eukaryotes and prokaryotes. For example, synonymous codon-choice patterns among mammals are very similar, while evolutionarily distant organisms such as yeast (*S. cerevisiae*), bacteria (such as *E. coli*) and insects (such as *D. melanogaster*) reveal a clearly different pattern of genomic codon use frequencies (Grantham, R., et al., Nucl. Acids Res., 8, 49–62 (1980); Grantham, R., et al., Nucl. Acids Res., 9, 43–74 (1981); Maroyama, T., et al., Nucl. Acids Res., 14, 151–197 (1986); Aota, S., et al., Nucl. Acids Res., 16, 315–402 (1988); Wada, K., et al., Nucl. Acids Res., 19 Supp., 1981–1985 (1991); Kurland, C. G., FEBS Letters, 285, 165–169 (1991)). These differences in codon-choice patterns appear to contribute to the overall expression levels of individual genes by modulating peptide elongation rates. (Kurland, C. G., FEBS Letters, 285, 165–169 (1991); Pedersen, S., EMBO J., 3, 2895–2898 (1984); Sorensen, M. A., J. Mol. Biol., 207, 365–377 (1989); Randall, L. L., et al., Eur. J. Biochem., 107, 375–379 (1980); Curran, J. F., and Yarus, M., J. Mol. Biol., 209, 65–77 (1989); Varenne, S., et al., J. Mol, Biol., 180, 549–576 (1984), Varenne, S., et al., J. Mol, Biol., 180, 549–576 (1984); Garel, J.-P., J. Theor. Biol., 43, 211–225 (1974); Ikemura, T., J. Mol. Biol., 146, 1–21 (1981); Ikemura, T., J. Mol. Biol., 151, 389–409 (1981)).

The preferred codon usage frequencies for a synthetic gene should reflect the codon usages of nuclear genes derived from the exact (or as closely related as possible) genome of the cell/organism that is intended to be used for recombinant protein expression, particularly that of yeast species. As discussed above, in one preferred embodiment the human Tf sequence is codon optimized, before or after modification as herein described for yeast expression as may be the nucleotide sequence of the therapeutic protein.

Vectors

Expression units for use in the present invention will generally comprise the following elements, operably linked in a 5' to 3' orientation: a transcriptional promoter, a secretory signal sequence, a DNA sequence encoding a modified Tf fusion protein comprising transferrin protein or a portion of a transferrin protein joined to a DNA sequence encoding a therapeutic protein or peptide of interest, preferably a therapeutic protein, and a transcriptional terminator. As discussed above, any arrangement of the therapeutic protein or peptide fused to or within the Tf portion may be used in the vectors of the invention. The selection of suitable promoters, signal sequences and terminators will be determined by the selected host cell and will be evident to one skilled in the art and are discussed more specifically below.

Suitable yeast vectors for use in the present invention are described in U.S. Pat. No. 6,291,212 and include YRp7 (Struhl et al., Proc. Natl. Acad. Sci. USA 76: 1035–1039, 1978), YEp13 (Broach et al., Gene 8: 121–133, 1979), pJDB249 and pJDB219 (Beggs, Nature 275:104–108, 1978), pPPC0005, pSeCHSA, pScNHSA, pC4 and derivatives thereof. Useful yeast plasmid vectors also include pRS403–406, pRS413–416 and the Pichia vectors available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, 7RPI, LEU2 and URA3. Plasmids pRS413~41.6 are Yeast Centromere plasmids (Ycps).

Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., Gene 8: 17, 1979), HIS3 (Struhl et al., ibid.) or POT1 (Kawasaki and Bell, EP 171,142). Other suitable selectable markers include the CAT gene, which confers chloramphenicol resistance on yeast cells. Preferred promoters for use in yeast include promoters from yeast glycolytic genes (Hitzeman et al., J Biol. Chem. 225: 12073–12080, 1980; Alber and Kawasaki, J. Mol. Appl. Genet. 1: 419–434, 1982; Kawasaki, U.S. Pat. No. 4,599,311) or alcohol dehydrogenase genes (Young et al., in Genetic Engineering of Microorganisms for Chemicals, Hollaender et al., (eds.), p. 355, Plenum, N.Y., 1982; Ammerer, Meth. Enzymol. 101: 192–201, 1983). In this regard, particularly preferred promoters are the TPI1 promoter (Kawasaki, U.S. Pat. No. 4,599,311) and the ADH2-4ᶜ (see U.S. Pat. No. 6,291,212) promoter (Russell et al., Nature 304: 652–654, 1983). The expression units may also include a transcriptional terminator. A preferred transcriptional terminator is the TPI1 terminator (Alber and Kawasaki, ibid.).

In addition to yeast, modified fusion proteins of the present invention can be expressed in filamentous fungi, for example, strains of the fungi *Aspergillus*. Examples of useful promoters include those derived from *Aspergillus nidulans* glycolytic genes, such as the ADH3 promoter (McKnight et al., EMBO J. 4: 2093–2099, 1985) and the tpiA promoter. An example of a suitable terminator is the ADH3 terminator (McKnight et al., ibid.). The expression units utilizing such components may be cloned into vectors that are capable of insertion into the chromosomal DNA of *Aspergillus*, for example.

Mammalian expression vectors for use in carrying out the present invention will include a promoter capable of directing the transcription of the modified Tf fusion protein, preferably a transferrin fusion protein comprising a modified Tf. Preferred promoters include viral promoters and cellular promoters. Preferred viral promoters include the major late promoter from adenovirus 2 (Kaufman and Sharp, Mol. Cell. Biol. 2: 1304–13199, 1982) and the SV40 promoter (Subramani et al, Mol. Cell. Biol. 1: 854–864, 1981).

Preferred cellular promoters include the mouse metallothionein-1 promoter (Palmiter et al., Science 222: 809–814, 1983) and a mouse VK (see U.S. Pat. No. 6,291,212) promoter (Grant et al., Nuc. Acids Res. 15: 5496, 1987). A particularly preferred promoter is a mouse VH (see U.S. Pat. No. 6,291,212) promoter. Such expression vectors may also contain a set of RNA splice sites located downstream from the promoter and upstream from the DNA sequence encoding the transferrin fusion protein. Preferred RNA splice sites may be obtained from adenovirus and/or immunoglobulin genes.

Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., Nuc. Acids Res. 9: 3719–3730, 1981). A particularly preferred polyadenylation signal is the $V_H$ (see U.S. Pat. No. 6,291,212) gene terminator. The expression vectors may include a noncoding viral leader sequence, such as the adenovirus 2 tripartite leader, located between the promoter and the RNA splice sites. Preferred vectors may also include enhancer sequences, such as the SV40 enhancer and the mouse μ (see U.S. Pat. No. 6,291,212) enhancer (Gillies, Cell 33: 717–728, 1983). Expression vectors may also include sequences encoding the adenovirus VA RNAs.

Transformation

Techniques for transforming fungi are well known in the literature, and have been described, for instance, by Beggs (ibid.), Hinnen et al. (Proc. Natl. Acad. Sci. USA 75: 1929–1933, 1978), Yelton et al., (Proc. Natl. Acad. Sci. USA 81: 1740–1747, 1984), and Russell (Nature 301: 167–169, 1983). The genotype of the host cell will generally contain a genetic defect that is complemented by the selectable marker present on the expression vector. Choice of a particular host and selectable marker is well within the level of ordinary skill in the art.

Cloned DNA sequences comprising modified Tf fusion proteins of the invention may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841–845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFR (see U.S. Pat. No. 6,291,212) cDNA (Simonsen and Levinson, Proc. Natl. Acad. Sci. USA 80: 2495–2499, 1983). Selectable markers are reviewed by Thilly (Mammalian Cell Technology, Butterworth Publishers, Stoneham, Mass.) and the choice of selectable markers is well within the level of ordinary skill in the art.

Host Cells

The present invention also includes a cell, preferably a yeast cell transformed to express a modified transferrin fusion protein of the invention. In addition to the transformed host cells themselves, the present invention also includes a culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away.

Host cells for use in practicing the present invention include eukaryotic cells, and in some cases prokaryotic cells, capable of being transformed or transfected with exogenous DNA and grown in culture, such as cultured mammalian, insect, fungal, plant and bacterial cells.

Fungal cells, including species of yeast (e.g., Saccharomyces spp., Schizosaccharomyces spp., Pichia spp.) may be used as host cells within the present invention. Exemplary genera of yeast contemplated to be useful in the practice, of the present invention as hosts for expressing the transferrin fusion protein, preferably the transferrin fusion protein, of the inventions are Pichia (formerly classified as Hansenula), Saccharomyces, Kluyveromyces, Aspergillus, Candida, Torulopsis, Torulaspora, Schizosaccharomyces, Citeromyces, Pachysolen, Zygosaecharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopyis, and the like. Examples of Saccharomyces spp. are S. cerevisiae, S. italicus and S. rouxii. Examples of Kluyveromyces spp. are K. fragilis, K. lactis and K. marxianus. A suitable Tõrulasppra species is T delbrueckii. Examples of Pichia (Hansenula) spp. are P. angusta (formerly H. polymorpha), P. anomala (formerly H. anomala) and P. pastoris.

Particularly useful host cells to produce the Tf fusion proteins of the invention are the methanoltrophic Pichia pastoris (Steinlein et al. (1995) Protein Express. Purif. 6:619–624). Pichia pastoris has been developed to be an outstanding host for the production of foreign proteins since its alcohol oxidase promoter was isolated and cloned; its transformation was first reported in 1985. P. pastoris can utilize methanol as a carbon source in the absence of glucose. The P. pastoris expression system can use the methanol-induced alcohol oxidase (AOX1) promoter, which controls the gene that codes for the expression of alcohol oxidase, the enzyme which catalyzes the first step in the metabolism of methanol. This promoter has been characterized and incorporated into a series of P. pastoris expression vectors. Since the proteins produced in P. pastoris are typically folded correctly and secreted into the medium, the fermentation of genetically engineered P. pastoris provides an excellent alternative to E. coli expression systems. A number of proteins have been produced using this system, including tetanus toxin fragment, Bordatella pertussis pertactin, human serum albumin and lysozyme.

The transformation of F. oxysporum may, for instance, be carried out as described by Malardier et al. (1989) Gene 78:147–156.

Strains of the yeast Saccharomyces cerevisiae are another preferred host. In a preferred embodiment, a yeast cell, or more specifically, a Saccharomyces cerevisiae host cell that contains a genetic deficiency in a gene required for asparagine-linked glycosylation of glycoproteins is used. S. cerevisiae host cells having such defects may be prepared using standard techniques of mutation and selection, although many available yeast strains have been modified to prevent or reduce glycosylation or hypermannosylation. Ballou et al. (J. Biol. Chem. 255: 5986–5991, 1980) have described the isolation of mannoprotein biosynthesis mutants that are defective in genes which affect asparagine-linked glycosylation.

To optimize production of the heterologous proteins, it is also preferred that the host strain carries a mutation, such as the *S. cerevisiae* pep4 mutation (Jones, Genetics 85: 23–33, 1977), which results in reduced proteolytic activity. Host strains containing mutations in other protease encoding regions are particularly useful to produce large quantities of the Tf fusion proteins of the invention.

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which are complemented by the selectable marker on the DNA construct or co-transfected with the DNA construct. Yeast cells, for example, are preferably grown in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M., preferably at 0.5 M or 1.0 M.

Cultured mammalian cells are generally grown in commercially available serum-containing or serum-free media. Selection of a medium appropriate for the particular cell line used is within the level of ordinary skill in the art. Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Baculovirus/insect cell expression systems may also be used to produce the modified Tf fusion proteins of the invention. The BacPAK™ Baculovirus Expression System (BD Biosciences (Clontech) expresses recombinant proteins at high levels in insect host cells. The target gene is inserted into a transfer vector, which is cotransfected into insect host cells with the linearized BacPAK6 viral DNA. The BacPAK6 DNA is missing an essential portion of the baculovirus genome. When the DNA recombines with the vector, the essential element is restored and the target gene is transferred to the baculovirus genome. Following recombination, a few viral plaques are picked and purified, and the recombinant phenotype is verified. The newly isolated recombinant virus can then be amplified and used to infect insect cell cultures to produce large amounts of the desired protein.

Secretory Signal Sequences

The terms "secretory signal sequence" or "signal sequence" or "secretion leader sequence" are used interchangeably and are described, for example in U.S. Pat. No. 6,291,212 and U.S. Pat No. 5,547,871, both of which are herein incorporated by reference in their entirety. Secretory signal sequences or signal sequences or secretion leader sequences encode secretory peptides. A secretory peptide is an amino acid sequence that acts to direct the secretion of a mature polypeptide or protein from a cell. Secretory peptides are generally characterized by a core of hydrophobic amino acids and are typically (but not exclusively) found at the amino termini of newly synthesized proteins. Very often the secretory peptide is cleaved from the mature protein during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis.

Secretory peptides may be used to direct the secretion of modified Tf fusion proteins of the invention. One such secretory peptide that may be used in combination with other secretory peptides is the third domain of the yeast Barrier protein. Secretory signal sequences or signal sequences or secretion leader sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral, mammalian or yeast expression vectors. In some cases, the native Tf signal sequence may be used to express and secrete fusion proteins of the invention.

Linkers

The Tf moiety and the therapeutic protein of the modified transferrin fusion proteins of the invention can be fused directly or using a linker peptide of various lengths to provide greater physical separation and allow more spatial mobility between the fused proteins and thus maximize the accessibility of the therapeutic protein, for instance, for binding to its cognate receptor. The linker peptide may consist of amino acids that are flexible or more rigid. For example, a linker such as but not limited to a poly-glycine stretch. The linker can be less than about 50, 40, 30, 20, or 10 amino acid residues. The linker can be covalently linked to and between the transferrin protein or portion thereof and the therapeutic protein.

Detection of Tf Fusion Proteins

Assays for detection of biologically active modified transferrin-fusion protein may include Western transfer, protein blot or colony filter as well as activity based assays that detect the fusion protein comprising transferrin and therapeutic protein. A Western transfer filter may be prepared using the method described by Towbin et al. (*Proc. Natl. Acad. Sci. USA* 76: 4350–4354, 1979). Briefly, samples are electrophoresed in a sodium dodecylsulfate polyacrylamide gel. The proteins in the gel are electrophoretically transferred to nitrocellulose paper. Protein blot filters may be prepared by filtering supernatant samples or concentrates through nitrocellulose filters using, for example, a Minifold (Schleicher & Schuell, Keene, N. H.). Colony filters may be prepared by growing colonies on a nitrocellulose filter that has been laid across an appropriate growth medium. In this method, a solid medium is preferred. The cells are allowed to grow on the filters for at least 12 hours. The cells are removed from the filters by washing with an appropriate buffer that does not remove the proteins bound to the filters. A preferred buffer comprises 25 mM Tris-base, 19 mM glycine, pH 8.3, 20% methanol.

Transferrin fusion proteins of the present invention may be labeled with a radioisotope or other imaging agent and used for in vivo diagnostic purposes. Preferred radioisotope imaging agents include iodine-125 and technetium-99, with technetium-99 being particularly preferred. Methods for producing protein-isotope conjugates are well known in the art, and are described by, for example, Eckelman et al. (U.S. Pat. No. 4,652,440), Parker et al. (WO 87/05030) and Wilber et al. (EP 203,764). Alternatively, the transferrin fusion proteins may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026).

Detection of a transferrin fusion protein of the present invention can be facilitated by coupling (i.e., physically linking) the therapeutic protein to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In one embodiment where one is assaying for the ability of a transferrin fusion protein of the invention to bind or compete with an antigen for binding to an antibody, various immunoassays known in the art can be used, including but not limited to, competitive and non-competitive assay systems using techniques such as radioimmunoassays, ELISA (enzyme linked immunosorbent assay), sandwich immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays), complement fixation assays, immunofluorescence assays, protein A assays, and immunoelectrophoresis assays, etc. In one embodiment, the binding of the transferrin fusion protein is detected by detecting a label on the transferrin fusion protein. In another embodiment, the transferrin fusion protein is detected by detecting binding of a secondary antibody or reagent that interacts with the transferrin fusion protein. In a further embodiment, the secondary antibody or reagent is labeled. Many means are known in the art for detecting binding in an immunoassay and are within the scope of the present invention.

Fusion proteins of the invention may also be detected by assaying for the activity of the therapeutic protein moiety. Specifically, transferrin fusion proteins of the invention may be assayed for functional activity (e.g., biological activity or therapeutic activity) using assays known to one of ordinary skill in the art. Additionally, one of skill in the art may routinely assay fragments of a therapeutic protein corresponding to a therapeutic protein portion of a fusion protein of the invention, for activity using well-known assays. Further, one of skill in the art may routinely assay fragments of a modified transferrin protein for activity using assays known in the art.

For example, in one embodiment where one is assaying for the ability of a transferrin fusion protein of the invention to bind or compete with a therapeutic protein for binding to an anti-therapeutic polypeptide antibody and/or anti-transferrin antibody, various immunoassays known in the art can be used, including but not limited to, competitive and non-competitive assay systems using techniques such as radioimmunoassays, ELISA (enzyme linked immunosorbent assay), sandwich immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In a further embodiment, where a binding partner (e.g., a receptor or a ligand) of a therapeutic protein is identified, binding to that binding partner by a transferrin fusion protein containing that therapeutic protein as the therapeutic protein portion of the fusion can be assayed, e.g., by means well-known in the art, such as, for example, reducing and non-reducing gel chromatography, protein affinity chromatography, and affinity blotting. Other methods will be known to the skilled artisan and are within the scope of the invention.

Production of Fusion Proteins

The present invention further provides methods for producing a modified fusion protein of the invention using nucleic acid molecules herein described. In general terms, the production of a recombinant form of a protein typically involves the following steps.

A nucleic acid molecule is first obtained that encodes a transferrin fusion protein of the invention. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be accomplished in a variety of ways. For example, the construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier and are otherwise known to persons skilled in the art. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce a desired recombinant protein.

As discussed above, any expression system may be used, including yeast, bacterial, animal, plant, eukaryotic and prokaryotic systems. In some embodiments, yeast, mammalian cell culture and transgenic animal or plant production systems are preferred. In other embodiments, yeast systems that have been modified to reduce native yeast glycosylation, hyper-glycosylation or proteolytic activity may be used.

Isolation/Purification of Modified Transferrin Fusion Proteins

Secreted, biologically active, modified transferrin fusion proteins may be isolated from the medium of host cells grown under conditions that allow the secretion of the biologically active fusion proteins. The cell material is removed from the culture medium, and the biologically active fusion proteins are isolated using isolation techniques known in the art. Suitable isolation techniques include precipitation and fractionation by a variety of chromatographic methods, including gel filtration, ion exchange chromatography and affinity chromatography.

A particularly preferred purification method is affinity chromatography on an iron binding or metal chelating column or an immunoaffinity chromatography using an antigen directed against the transferrin or therapeutic protein of the polypeptide fusion. The antigen is preferably immobilized or attached to a solid support or substrate. A particularly preferred substrate is CNBr-activated Sepharose (Pharmacia LKB Technologies, Inc., Piscataway, N.J.). By this method, the medium is combined with the antigen/substrate under conditions that will allow binding to occur. The complex may be washed to remove unbound material, and the transferrin fusion protein is released or eluted through the use of conditions unfavorable to complex formation. Particularly useful methods of elution include changes in pH, wherein the immobilized antigen has a high affinity for the transferrin fusion protein at a first pH and a reduced affinity at a second (higher or lower) pH; changes in concentration of certain chaotropic agents; or through the use of detergents.

Delivery of a Drug or Therapeutic Protein to the Inside of a Cell and/or Across the Blood Brain Barrier (BBB)

Within the scope of the invention, the modified transferrin fusion proteins may be used as a carrier to deliver a molecule or small molecule therapeutic complexed to the ferric ion of transferrin to the inside of a cell or across the blood brain barrier. In these embodiments, the transferrin will typically be engineered or modified to inhibit, prevent or remove glycosylation to extend the serum half-life of the transferrin fusion protein and/or therapeutic protein. The addition of a targeting peptide is specifically contemplated to further target the transferrin fusion protein to a particular cell type, e.g., a cancer cell.

In one embodiment, the iron-containing, anti-anemic drug, ferric-sorbitol-citrate complex is loaded onto a modified Tf fusion protein of the invention. Ferric-sorbitol-citrate (FSC) has been shown to inhibit proliferation of various murine cancer cells in vitro and cause tumor regression in vivo, while not having any effect on proliferation of non-malignant cells (Poljak-Blazi et al. (June 2000) *Cancer Biotherapy and Radiopharmaceuticals* (United States), 15/3:285–293).

In another embodiment, the antineoplastic drug adriamycin (Doxorubicin) and/or the chemotherapeutic drug bleomycin, both of which are known to form complexes with ferric ion, is loaded onto a transferrin fusion protein of the invention. In other embodiments, a salt of a drug, for instance, a citrate or carbonate salt, may be prepared and complexed with the ferric iron that is then bound to Tf. As tumor cells often display a higher turnover rate for iron; transferrin modified to carry at least one anti-tumor agent, may provide a means of increasing agent exposure or load to the tumor cells. (Demant, E. J., (1983) *Eur. J. of Biochem.* 137/(1–2):113–118, Padbury et al. (1985) J. Biol. Chem. 260/13:7820–7823).

Pharmaceutical Formulations and Treatment Methods

The modified fusion proteins comprising a modified transferrin of the invention may be administered to a patient in need thereof using standard administration protocols. For instance, the modified Tf fusion proteins of the present invention can be provided alone, or in combination, or in sequential combination with other agents that modulate a particular pathological process. As used herein, two agents are said to be administered in combination when the two agents are administered simultaneously or are administered independently in a fashion such that the agents will act at the same or near the same time.

The fusion proteins of the present invention can be administered via parenteral, subcutaneous, intravenous, intramuscular, intraperitoneal, transdermal and buccal routes. For example, an agent may be administered locally to a site of injury via microinfusion. Alternatively, or concurrently, administration may be noninvasive by either the oral, inhalation, nasal, or pulmonary route. The dosage administered will be dependent upon the age, health, and weight of the recipient, kind of concurrent treatment, if any, frequency of treatment, and the nature of the effect desired.

The present invention further provides compositions containing one or more fusion proteins of the invention. While individual needs vary, determination of optimal ranges of effective amounts of each component is within the skill of the art. Typical dosages comprise about 1 pg/kg to about 100 mg/kg body weight. The preferred dosages for systemic administration comprise about 100 ng/kg to about 100 mg/kg body weight or about 100–200 mg of protein/dose. The preferred dosages for direct administration to a site via microinfusion comprise about 1 ng/kg to about 1 mg/kg body weight. When administered via direct injection or microinfusion, modified fusion proteins of the invention may be engineered to exhibit reduced or no binding of iron to prevent, in part, localized iron toxicity.

In addition to the pharmacologically active fusion protein, the compositions of the present invention may contain suitable pharmaceutically acceptable carriers comprising excipients and auxiliaries that facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient. Suitable formulations for oral administration include hard or soft gelatin capsules, pills, tablets, including coated tablets, elixirs, suspensions, syrups or inhalations and controlled release forms thereof.

The pharmaceutical composition of the present invention can be in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the physician.

In practicing the methods of this invention, the fusion proteins of this invention may be used alone or in combination, or in combination with other therapeutic or diagnostic agents. In certain preferred embodiments, the compounds of this invention may be co-administered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

Transgenic Animals

The production of transgenic non-human animals that contain a modified transferrin fusion construct with increased serum half-life increased serum stability or increased bioavailability of the instant invention is contemplated in one embodiment of the present invention. In some embodiments, lactoferrin may be used as the Tf portion of the fusion protein so that the fusion protein is produced and secreted in milk.

The successful production of transgenic, non-human animals has been described in a number of patents and publications, such as, for example U.S. Pat. No. 6,291,740 (issued Sep. 18, 2001); U.S. Pat. No. 6,281,408 (issued Aug. 28, 2001); and U.S. Pat. No. 6,271,436 (issued Aug. 7, 2001) the contents of which are hereby incorporated by reference in their entireties.

The ability to alter the genetic make-up of animals, such as domesticated mammals including cows, pigs, goats, horses, cattle, and sheep, allows a number of commercial applications. These applications include the production of animals which express large quantities of exogenous proteins in an easily harvested form (e.g., expression into the milk or blood), the production of animals with increased weight gain, feed efficiency, carcass composition, milk production or content, disease resistance and resistance to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos (Wall et al., J. Cell. Biochem. 49:113 [1992]). Other methods for the production of transgenic animals include the infection of embryos with retroviruses or with retroviral vectors. Infection of both pre- and post-implantation mouse embryos with either wild-type or recombinant retroviruses has been reported (Janenich, Proc. Natl. Acad. Sci. USA 73:1260 [1976]; Janenich et al., Cell 24:519 [1981]; Stuhlmann et al., Proc. Natl. Acad. Sci. USA 81:7151 [1984]; Jahner et al., Proc. Natl. Acad Sci. USA 82:6927 [1985]; Van der Putten et al., Proc. Natl. Acad Sci. USA 82:6148–6152 [1985]; Stewart et al., EMBO J. 6:383–388 [1987]).

An alternative means for infecting embryos with retroviruses is the injection of virus or virus-producing cells into the blastocoele of mouse embryos (Jahner, D. et al., Nature 298:623 [1982]). The introduction of transgenes into the germline of mice has been reported using intrauterine retroviral infection of the midgestation mouse embryo (Jahner et al., supra [1982]). Infection of bovine and ovine embryos with retroviruses or retroviral vectors to create transgenic animals has been reported. These protocols involve the microinjection of retroviral particles or growth arrested (i.e., mitomycin C-treated) cells which shed retroviral particles into the perivitelline space of fertilized eggs or early embryos (PCT International Application WO 90/08832 [1990]; and Haskell and Bowen, Mol. Reprod. Dev., 40:386 [1995]. PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

U.S. Pat. No. 6,291,740 (issued Sep. 18, 2001) describes the production of transgenic animals by the introduction of exogenous DNA into pre-maturation oocytes and mature, unfertilized oocytes (i.e., pre-fertilization oocytes) using retroviral vectors which transduce dividing cells (e.g., vectors derived from murine leukemia virus [MLV]). This patent also describes methods and compositions for cytomegalovirus promoter-driven, as well as mouse mammary tumor LTR expression of various recombinant proteins.

U.S. Pat. No. 6,281,408 (issued Aug. 28, 2001) describes methods for producing transgenic animals using embryonic stem cells. Briefly, the embryonic stem cells are used in a mixed cell co-culture with a morula to generate transgenic animals. Foreign genetic material is introduced into the embryonic stem cells prior to co-culturing by, for example, electroporation, microinjection or retroviral delivery. ES cells transfected in this manner are selected for integrations of the gene via a selection marker such as neomycin.

U.S. Pat. No. 6,271,436 (issued Aug. 7, 2001) describes the production of transgenic animals using methods including isolation of primordial germ cells, culturing these cells to produce primordial germ cell-derived cell lines, transforming both the primordial germ cells and the cultured cell lines, and using these transformed cells and cell lines to generate transgenic animals. The efficiency at which transgenic animals are generated is greatly increased, thereby allowing the use of homologous recombination in producing transgenic non-rodent animal species.

Gene Therapy

The use of modified transferrin fusion constructs for gene therapy wherein a modified transferrin protein or transferrin domain is joined to a therapeutic protein or peptide is contemplated in one embodiment of this invention. The modified transferrin fusion constructs with increased serum half-life or serum stability of the instant invention are ideally suited to gene therapy treatments.

The successful use of gene therapy to express a soluble fusion protein has been described. Briefly, gene therapy via injection of an adenovirus vector containing a gene encoding a soluble fusion protein consisting of cytotoxic lymphocyte antigen 4 (CTLA4) and the Fe portion of human immunoglubulin G1 was recently shown in Ijima et al. (Jun. 10, 2001) Human Gene Therapy (United States) 12/9:1063–77. In this application of gene therapy, a murine model of type II collagen-induced arthritis was successfully treated via intraarticular injection of the vector.

Gene therapy is also described in a number of U.S. patents including U.S. Pat. No. 6,225,290 (issued May 1, 2001); U.S. Pat. No. 6,187,305 (issued Feb. 13, 2001); and U.S. Pat. No. 6,140,111 (issued Oct. 31, 2000).

U.S. Pat. No. 6,225,290 provides methods and constructs whereby intestinal epithelial cells of a mammalian subject are genetically altered to operatively incorporate a gene which expresses a protein which has a desired therapeutic effect. Intestinal cell transformation is accomplished by administration of a formulation composed primarily of naked DNA, and the DNA may be administered orally. Oral or other intragastrointestinal routes of administration provide a simple method of administration, while the use of naked nucleic acid avoids the complications associated with use of viral vectors to accomplish gene therapy. The expressed protein is secreted directly into the gastrointestinal tract and/or blood stream to obtain therapeutic blood levels of the protein thereby treating the patient in need of the protein. The transformed intestinal epithelial cells provide short or long term therapeutic cures for diseases associated with a deficiency in a particular protein or which are amenable to treatment by overexpression of a protein.

U.S. Pat. No. 6,187,305 provides methods of gene or DNA targeting in cells of vertebrate, particularly mammalian, origin. Briefly, DNA is introduced into primary or secondary cells of vertebrate origin through homologous recombination or targeting of the DNA, which is introduced into genomic DNA of the primary or secondary cells at a preselected site.

U.S. Pat. No. 6,140,111 (issued Oct. 31, 2000) describes retroviral gene therapy vectors. The disclosed retroviral vectors include an insertion site for genes of interest and are capable of expressing high levels of the protein derived from the genes of interest in a wide variety of transfected cell types. Also disclosed are retroviral vectors lacking a selectable marker, thus rendering them suitable for human gene therapy in the treatment of a variety of disease states without the co-expression of a marker product, such as an antibiotic. These retroviral vectors are especially suited for use in certain packaging cell lines. The ability of retroviral vectors to insert into the genome of mammalian cells have made them particularly promising candidates for use in the genetic therapy of genetic diseases in humans and animals. Genetic therapy typically involves (1) adding new genetic material to patient cells in vivo, or (2) removing patient cells from the body, adding new genetic material to the cells and reintroducing them into the body, i.e., in vitro gene therapy. Discussions of how to perform gene therapy in a variety of cells using retroviral vectors can be found, for example, in U.S. Pat. Nos. 4,868,116, issued Sep. 19, 1989, and 4,980,286, issued Dec. 25, 1990 (epithelial cells), WO89/07136 published Aug. 10, 1989 (hepatocyte cells), EP 378,576 published Jul. 25, 1990 (fibroblast cells), and WO89/05345 published Jun. 15, 1989 and WO/90/06997, published Jun. 28, 1990 (endothelial cells), the disclosures of which are incorporated herein by reference.

Kits Containing Transferrin Fusion Proteins

In a further embodiment, the present invention provides kits containing transferrin fusion proteins, which can be used, for instance, for the therapeutic or non-therapeutic applications. The kit comprises a container with a label. Suitable containers include, for example, bottles, vials, and test tubes. The containers may be formed from a variety of materials such as glass or plastic. The container holds a composition which includes a transferrin fusion protein that is effective for therapeutic or non-therapeutic applications, such as described above. The active agent in the composition is the therapeutic protein. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

Without further description, it is believed that a person of ordinary skill in the art can, using the preceding description and the following illustrative examples, make and utilize the present invention and practice the claimed methods. For example, a skilled artisan would readily be able to determine the biological activity, both in vitro and in vivo, for the fusion protein constructs of the present invention as compared with the comparable activity of the therapeutic moiety in its unfused state. Similarly, a person skilled in the art could readily determine the serum half life and serum stability of constructs according to the present invention. The following working examples therefore, specifically point out the preferred embodiments of the present invention, and are not to be construed as limiting in any way the remainder of the disclosure.

EXAMPLES

Example 1

T-20/Transferrin Fusion Protein

T-20 is a HIV fusogenic inhibitor peptide with the following amino acid sequence: YTSLIHSLIEESQN-QQEKNEQELLELDKWASLWNWF (SEQ ID NO: 17). The present invention provides fusion proteins comprising T-20 peptide and modified transferrin (mTf) with increased half-life and pharmaceutical compositions of such fusion proteins for the treatment of diseases associated with the transmission of a virus. The example described below may also be used to generate transferrin fusion proteins with analogs of the T-20 peptides.

The transferrin fusion protein with anti-HIV activity of the present invention was produced by fusing T-20 to modified transferrin (mTf) using *Saccharomyces cerevisiae*. Accordingly, in the first step, SEQ ID NO: 17 was back translated into DNA codon optimized for *Saccharomyces cerevisiae* and used to produce fusion constructs of T-20 at the n- or C-terminus of mTf.

5'Fusion

As an example, T-20 is fused to the 5' end of mTf using overlapping primers with restriction site overhangs at each end, such as XbaI and KpnI sites for ligation into an appropriate vector. Alternatively, overlapping primers with other restriction site overhangs could be generated or the primers could be annealed to adapters with appropriate restriction site overhangs for ligation into a specifically designed vector.

A vector is specifically designed with restriction sites such as XbaI and KpnI sites to allow fusion of therapeutic molecules into the N-terminus of mTf. The primers are annealed and cloned into this vector using the XbaI and KpnI sites or other appropriate rrestriction sites at the 5' end of the modified transferrin (mTf) vector. The cassette encoding the T-20/mTf fusion protein is then removed from the vector and cloned into a yeast vector for protein expression Specifically, the following overlapping primers with restriction overhangs are designed for producing the 5' T-20 fusion:

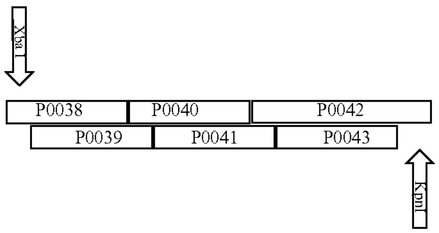

The overlapping primers have the following sequences:

P0038:
CTAGAGAAAAGGTACACTAGCTTAATACAC (SEQ ID NO: 18)

P0039:
TGCGATTCTTCAATTAAGGAGTGTATTAAGCTAGTGTACCTTTTCT (SEQ ID NO: 19)

P0040:
TCCTTAATTGAAGAATCGCAAAACCAGCAAGAAAAGAATG (SEQ ID NO: 20)

P0041:
TAATTCCAATAATTCTTGTTCATTCTTTTCTTGCTGGTTT (SEQ ID NO: 21)

P0042:
AACAAGAATTATTGGAATTAGATAAATGGGCAAGTTTGTGGAATTGGTTTGTAC (SEQ ID NO: 22)

P0043:
AAACCAATTCCACAAACTTGCCCATTTATC (SEQ ID NO: 23)

The primers are annealed at 65° C. and ligated into the specifically designed vector pREX5004, cut with XbaI and KpnI to create pREX5016. Following identification of a correct clone by sequencing, the correct clone is bulked up and digested with another pair of appropriate restriction enzymes such as PsiI and AgeI to remove the cassette encoding the T-20/mTf fusion protein out of pREX5016. The cassette is ligated into a yeast vector, such as pSAC3, cut with PsiI and AgeI. pSAC3 containing the T-20/mTf N-terminus fusion protein is then electroporated into yeast for protein production.

3' Fusion

In the same manner, T-20 fusion is fused to the 3' end of T-20 using overlapping primers with restriction site overhangs, such as SalI and HindIII or other restriction enzymes, at each end. Once annealed, this fragment is cloned into a specifically designed vector, pREX5001, using restriction sites such as SalI and HindIII sites. Following identification of the correct clone through sequencing, the plasmid is cut with SalI and HindIII and the fragment is sub-cloned into pREX5004 which is specifically designed to with unique SalI and HindIII sites to allow fusion of therapeutic protein to the C-terminus of mTf. The resulting plasmid is pREX5017. pREX5017 is then cut with appropriate enzymes such as PsiI and AgeI to remove the T-20/mTf cassette out of the vector. The T-20/m-Tf cassette is subcloned into a yeast vector, such as pSAC3, for expression in yeast.

Specifically, the following overlapping primers with restriction overhangs are designed for producing the T-20 fusion to the C-terminus of mTf:

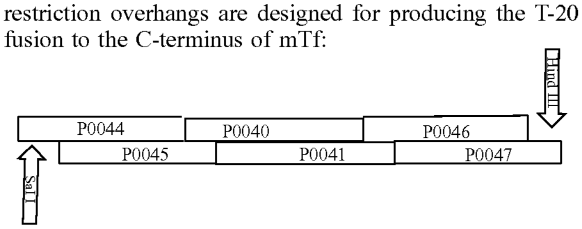

The overlapping primers have the following sequences:

P0044:
TCGACCTTACACTAGCTTAATACAC (SEQ ID NO: 24)

P0045:
TGCGATTCTTCAATTAAGGAGTGTATTAAGCTAGTGTAAGG (SEQ ID NO: 25)

P0040:
TCCTTAATTGAAGAATCGCAAAACCAGCAAGAAAAGAATG (SEQ ID NO: 26)

P0041:
TAATTCCAATAATTCTTGTTCATTCTTTTCTTGCTGGTTT (SEQ ID NO: 27)

P0046:
AACAAGAATTATTGGAATTAGATAAATGGGCAAGTTTGTGGAATTGGTTTTTAATA (SEQ ID NO: 28)

```
P0047:
AGCTTATTAAAACCAATTCCACAAACTTGCCCATTTATC                    (SEQ ID NO: 29)
```

The primers are annealed at 65° C. and ligated into the specifically designed vector cut with SalI and HindIII. Following identification of a correct clone by sequencing, the correct clone is bulked up and digested with another pair of appropriate restriction enzymes such as PsiI and AgeI to remove the cassette encoding the T-20/mTf C-terminus fusion protein out of the vector. This cassette is ligated into a yeast vector, such as pSAC3, cut with PsiI and AgeI. pSAC3 containing the T-20/mTf fusion protein is then electroporated into yeast for protein production.

C-terminus Modifications

Modifications are made at the 3' end of mTf to determine if they would effect an increase in fusion expression levels, T-20 fusion activity, and/or improve mobility of the peptide at the C terminus of mTf.

RRP Deletion

In the first step, proline at the 3' end of mTf is removed. In addition to the proline, the adjoining two arginine residues are removed since they may present a potential Kex2p protease cleavage site. The deleted sequence is shown in the alignment below of unmodified 3' T-20 mTf fusion insert (pREX5017, SEQ ID NO: 31) and 3' T-20 mTf fusion insert with RRP deletion (pREX5032, SEQ ID NO: 30):

```
caaggctgttggtaacctgagaaaatgctccacctcatcactcctggaagcctgcacttt (pREX5032: SEQ ID NO: 30)
caaggctgttggtaacctgagaaaatgctccacctcatcactcctggaagcctgcacttt (pREX5017: SEQ ID NO: 31)
         ArgArgPro
c---------tacactagcttaatacactccttaattgaagaatcgcaaaaccagcaag
ccgtcgaccttacactagcttaatacactccttaattgaagaatcgcaaaaccagcaag
aaagaatgaacaagaattattggaattagataaatgggcaagtttgtggaattggtttta
aaagaatgaacaagaattattggaattagataaatgggcaagtttgtggaattggtttta
ataa
ataa
```

Specifically, the RRP sequence is deleted using primers homologous to adjoining regions of the sequence. The primers used for generating the deletion are:

P0060:
TCATCACTCCTGGAAGCCTGCACTTTCTACACTAGCTTAATACACTCCTT (SEQ ID NO: 32)

P0061:
AAGGAGTGTATTAAGCTAGTGTAGAAAGTGCAGGCTTCCAGGAGTGATGA (SEQ ID NO: 33)

A mutagenic PCR reaction is performed using the external primers and pREX5017 as the template to generate a product missing the 9 bases coding for RRP. This product is then cut with SphI/HindIII and cloned into SphI/HindIII cut pREX5017 to make pREX5032. pREX5032 was then cut with AgeI/PsiI, sub-cloned into a yeast vector such as pSAC3 and transformed into yeast for protein expression.

C402-C674 Disulfide Removal

In the next step, the disulfide bond that stretches between Cys402 and Cys674 in the mTF molecule, is removed. This is accomplished by mutating both cysteine residues to glycine residues. First, using mutagenic primers Cys402 is mutated to Gly. The mutagenic primers are:

(SEQ ID NO: 34)
P0064: TTGTCTACATAGCGGGCAAGGGTGGTCTGGTGCCTGTCTTG (SEQ ID NO: 35)
P0065: CAAGACAGGCACCAGACCACCCTTGCCCGCTATGTAGACAA

A PCR reaction is performed using the external primers and pREX5017 as the template to generate the product with the desired mutation. This product is then cut with HpaI/PstI and cloned back into pREX5017 making a Gly402 intermediate, pREX5039. Next, Cys674 is mutated into Gly674 following the same procedure and using pREX5004 as a template and the following primers:

P0068:
TCCACCTCATCACTCCTGGAAGCCGGTACTTTCCGTCGACCTTAA   (SEQ ID NO: 36)

P0069:
CTTATTAAGGTCGACGGAAAGTACCGGCTTCCAGGAGTGATGAGGTGG   (SEQ ID NO: 37)

The resulting product is cut with SphI/HindIII and sub-cloned into the new Gly402 intermediate, pREX5039, making pREX5038, This plasmid does not contain the T-20 peptide making it useful in the future for other mTf fusions. To insert the T-20 peptide into pREX5038, the SalI/AgeI fragment of pREX5017 is cloned to form pREX5034. pREX5034 was then cut with AgeI/PsiI. The cassette is sub-cloned into a yeast vector, such as pSAC3, and transformed into yeast for protein expression. The mutations are shown in the alignment below of unmodified 3' T-20 mTf fusion plasmid insert (pREX5017) and 3' T-20 mTf fusion insert with C402–C674 disulfide deletion:

```
                            Cys
pREX5017 1501  tagcgggcaag t gtggtctggtgcctgtcttggcagaaaactacaataag  (SEQ ID NO: 38)
pREX5034 1501  tagcgggcaag g gtggtctggtgcctgtcttggcagaaaactacaataag  (SEQ ID NO: 39)
                            Gly Cys
pREX5017 2301  tgctccacctcatcactcctggaagcc t g c actttccgtcgaccttacac  (SEQ ID NO: 40)
pREX5034 2301  tgctccacctcatcactcctggaagcc g g t actttccgtcgaccttacac  (SEQ ID NO: 41)
                                                 Gly
```

Disulfide and RRP Removal Combination

In the third step, RRP deletion and the C402-C674 disulfide deletion are combined. To begin, an intermediate plasmid, pREX5041, is made in the manner as pREX5032 with the exception that the Cys674 mutation was present in the primers. The following primers are used:

P0066:
TCCACCTCATCACTCCTGGAAGCCGGCACTTTCTACACTAGCTTAATA   (SEQ ID NO: 42)

P0067:
GTGTATTAAGCTAGTGTAGAAAGTACCGGCTTCCAGGAGTGATGAGGT   (SEQ ID NO: 43)

pREX5041 is then cut with SphI/HindIII and sub-cloned into pREX5039 to create pREX5033. pREX5033 is then cut with AgeI/PsiI. The cassette is sub-cloned into a yeast vector, such as pSAC3, and then transformed into yeast for protein expression. The following alignment of the mTf 3'T-20 fusion of pREX5033 with pREX5017 shows the mutations of the resulting product.

```
              Cys
pREX5017 1501 tagcgggcaag t gtggtctggtgcctgtcttggcagaaaactacaataag  (SEQ ID NO: 38)
pREX5034 1501 tagcgggcaag g gtggtctggtgcctgtcttggcagaaaactacaataag  (SEQ ID NO: 39)
              Gly Cys     ArgArgPro
pREX5017 2301 tgctccacctcatcactcctggaagcc t g c actttc cgtcgacct tacac (SEQ ID NO: 40)
pREX5034 2301 tgctccacctcatcactcctggaagcc g g t actttc --------- tacac (SEQ ID NO: 41)
                                              Gly
```

Example 2

EMP1/Transferrin Fusion Protein

EMP1 (SEQ ID NO: 11) has been shown to mimic EPO activity by causing dimerization of the EPO receptor. The peptide, which is cyclic, has no homology to EPO. To become active, the peptide has to act in concert with another peptide, i.e. as a dimer, such that two copies of the receptor are brought in close enough proximity to form an active complex. As with many peptides, the peptide dimer suffers from short half life and would benefit from the longevity that fusion to transferrin would give. The present invention provides fusion protein with EPO mimetic activity. As an example, the fusion protein of the present invention comprises EMP1 peptide (SEQ ID NO: 11) and modified transferrin (mTf) with increased half-life. The present invention also provides pharmaceutical compositions of such fusion proteins for the treatment of diseases associated with low or defective red blood cell production.

EMP1-mTF Fusions and Insertions

The initial fusions to mTf comprises fusions to the N-, C-, and N- and C-termini of mTf. The individual fusions will bind the receptor but not cause activation of the receptor. The dual fusion, one of which must be a different codon composition than the other to prevent recombination, will enable binding to the receptor and cause activation.

Examination of the N-domain of human Tf (PDB identifier 1A8E) and the full Tf model AAAaoTfwo, generated using the ExPasy Swiss Model Server with the rabbit model 1JNF as template, reveals a number of potential sites for insertion of a peptide, either directly or by replacement of a number of residues. These sites are duplicated by their equivalent sites in the C domain.

| $N_1$ | $N_2$ |
|-------|-------|
| Asp33 | Ser105 |
| Asn55 | Glu141 |
| Asn75 | Asp166 |
| Asp90 | Gln184 |
| Gly257 | Asp197 |
| Lys280 | Lys217 |
| His289 | Thr231 |
| Ser298 | Cys241 |

Two of these loops are the preferred sites into which the EMP1 peptide may be inserted: $N_1$ His289 (286–292) and $N_2$ Asp166 (162–170). These positions give the correct orientation required for binding to the two halves of the EPO receptor. As the insertion sites are on the $N_1$ and $N_2$ domains of the N domain, they have the flexibility of the hinge between these two sub domains, which allows them to work their way into the receptor.

Due to the structural similarity between the N and C domain the equivalent insertion sites on the C domain ($C_1$ 489–495, $C_2$ 623–628) may also be used to make the molecule multivalent. This is done using a variety of the potential insert sites indicated above either on just the N or C domain or by a combination of sites on both domains.

```
N2 140  PEPRKPLEKA VANFFSGSCA PC ADGTDFPQ L CQLCP---- -GCGCSTLNQ
C1 472  NH------CR FDEFFSEGCA PG SKKD--SS L CKLCMGSGL NLCEPNNKEG

N2 140  PEP R KPLEKA VAN FFS GS CA P C ADGTDFPQ L CQLC P G C G --- C STL N --Q
C1 472  NHC R ------ FDE FFS EG CA P G SKKD--SS L CKLC M G S G L NL C EPN N KEG

N1 277  D-KSKE--FQ LF SSPHGKD L LFKDSAHGFL KVPPRMDAKM YLGYEYVTAI
C2 611  NVTDCSGNFC LF RSE-TKD L LFRDDTVCLA KLHDRNTYEK YLGEEYVKAV

N1 277  --- D K S KE F Q LF S S PHG KL L LF KD SAHGFL K VPP R MDA K M YLG Y EYV T A I
C2 611  NVT D C S GN F C LF R S ET- KD L LF R D DTVCLA K LHD R NTY E K YLG E EYV K A V
```

$N_1$ = SEQ ID NO: 13

$N_2$ = SEQ ID NO: 14

$C_1$ = SEQ ID NO: 15

$C_2$ = SEQ ID NO: 16

Steps for Producing the EMP1/mTf Fusion Protein In this Example, two EMP1 peptides (SEQ ID NO: 11) are engineered into the transferrin scaffold using the encoding nucleic acids of the peptides and mTf.

```
1 ggtggtactt actcttgtca ttttggtcca ttgacttggg tttgtaagcc acaaggtggt
   g  g  t   y  s  c  h  f  g  p   l  t  w   v  c  k   p  q  g  g nucleic acid sequence: SEQ ID NO: 45
amino acid sequence: SEQ ID NO: 11
```

A EMP1 peptide is engineered into mTf between His289 and Gly290. The duplication inherent to the transferrin molecule, with the two domains mirroring each other, makes it possible to engineer a second EMP1 peptide into the duplicate region of the C domain, between Glu625 and Thr626.

```
N 277 D-KSKE--FQ LFSSPHGKDL LFKDSAHGFL KVPPRMDAKM YLGYEYVTAI
C 611 NVTDCSGNFC LFRSE-TKDL LFRDDTVCLA KLHDRNTYEK YLGEEYVKAV

N domain: SEQ ID NO: 13
C domain: SEQ ID NO: 16
```

As an example, for each insertion two overlapping mutagenic primers are synthesized (see below). Using a vector containing the nucleic acid encoding mTf, such as pREX5010, as a template, reactions are performed with each mutagenic primer and an external primer from the 5' or 3' of the Tf cDNA. The products from these two reactions were then mixed and a further reaction performed with the external primers to join the two products together. The His289-Gly290 insert PCR product is digested with XbaI and HpaI for ligation into XbaI/HpaI digested pREX5010. The resulting vector is then digested with HpaI and SalI for ligation of HpaI/SalI digested Glu625-Thr626 insert PCR product.

```
His289—Gly290 insert                                                 (SEQ ID NO: 46)
                                             <---------------------
2031 agacaaatca[aaagaatttc aactattcag ctctcctcat ggtggtactt actcttgtca ttttggtcca
     tctgtttagt tttcttaaag ttgataagtc gagaggagta ccaccatgaa[tgagaacagt aaaaccaggt
                                               >>...............EMOm............>
     >..................................Tf....................................>
     >..............................N domain..................................>

2101 ttgacttggg tttgtaagcc]acaaggtggt gggaaggacc tgctgtttaa ggactctgcc cacgggtttt
     aactgaaccc aaacattcgg tgttccacca cccttcctgg acgacaaatt cctgagacgg]gtgcccaaaa
                                 ------------>
     >............EMOm............>>
     >..................................Tf....................................>
     >...............................N domain.................................>

Glu625-Thr626 insert                                                 (SEQ ID NO: 47)
                                                              <-------------
3081 cctatttgga agcaacgtaa ctgactgctc[gggcaacttt tgtttgttcc ggtcggaagg tggtacttac
     ggataaacct tcgttgcatt gactgacgag cccgttgaaa acaaacaagg ccagccttcc accatgaat[g
                                                                   >>...EPOm...>
     >...............................C domain.................................>
     >..................................Tf....................................>

Kpn I
                                                     -------
3151 tcttgtcatt ttggtccatt gacttgggtt tgtaagccac]aaggtggtac caaggacctt ctgttcagag
     agaacagtaa aaccaggtaa ctgaacccaa acattcggtg ttccaccatg gttcctggaa gacaagtctc
```

```
                          ------------>
>......................EPOm......................>>
>.................................C domain..................................>
>..................................Tf....................................>

3221 atgacacagt atgtttggcc aaacttcatg acagaaacac atatgaaaaa tacttaggag aagaatatgt
     tactgtgtca]tacaaaccgg tttgaagtac tgtctttgtg tatactttttt atgaatcctc ttcttataca
>.................................C domain..................................>
>..................................Tf....................................>
```

The cassette containing the EMP1/mTF fusion protein is cut out of the vector with appropriate restriction enzymes and ligated into a yeast vector, such as pSAC3. pSAC3 is transformed into yeast for protein expression.

Alternative points for insertion of the EPO mimetic peptide(s), or any other peptide(s) are the two glycosylation sites on the C domain of Transferrin at N413 and N611. The advantage of these sites is that once insertion is achieved, glycosylation is prevented by through disruption of the N-X-S/T sequence.

Example 3

GLP-1/Transferrin Fusion Protein

GLP-1 is a peptide that regulates insulin secretion. It possesses anti-diabetic activity in human subjects suffering diabetes, especially type II diabetes. Like other peptides, GLP-1 has a short plasma half-life in humans. The present invention provides fusion proteins with GLP-1 fused to mTf with increased half-life and pharmaceutical compositions of such fusion proteins for the treatment of diseases associated with abnormal glucose levels.

In this example, the steps for producing a GLP-1/mTf fusion protein are described. The same steps may be used to generate transferrin fusion proteins with analogs of the GLP-1 peptides.

To produce the GLP-1/mTf fusion protein, the amino acid sequence of GLP-1(7–36) and GLP-1(7–37) may be used.

```
haegtftsdvssylegqaakefiawlvkgr    (SEQ ID NO: 48)

haegtftsdvssylegqaakefiawlvkgrg   (SEQ ID NO: 66)
```

For example, the peptide sequence of GLP-1(7–36) is back translated into DNA and codon optimized for yeast:

```
catgctgaaggtacttttacttctgatgtttcttcttatttggaaggtcaagctgctaaagaa   (SEQ ID NO: 49)
 h  a  e  g  t  f  t  s  d  v  s  s  y  l  e  g  q  a  a  k  e   (SEQ ID NO: 48)

tttattgcttggttggttaaaggtaga
 f  i  a  w  l  v  k  g  r
```

The primers used are specifically designed to form a 5' XbaI and 3' KpnI sticky ends after annealing and be directly ligated into XbaI/KpnI cut pREX5004, just 5' of the end of the mating factor α leader sequence and at the N-terminus of mTf. Alternatively, other sticky ends may be engineered for ligations into other vectors.

```
                                                           Xba I
                                                          -+-----
  1   taaatactac tattgccagc attgctgcta aagaagaagg ggtatctcta
      gagaaaaggc
      atttatgatg ataacggtcg taacgacgat ttcttcttcc ccatagagat
      ctcttttccg
         >>..........................'MFa-1 (SEQ ID NO:
      52)............>>
            n  t  i  a  s    i  a  a  k  e  e-
         g  v  s  l  e  k  r 61   atgctgaagg tacttttact tctgatgttt cttcttattt ggaaggtcaa gct-
      gctaaag
      tacgacttcc atgaaaatga agactacaaa gaagaataaa ccttccagtt cgac-
      gatttc
         >.........................GLP-1 (SEQ ID NO:
      48)............>
            h   a   e   g   t   f   t   s   d   v   s-
              s   y   l   e   g   q   a   a   k Kpn I
                                                 ------+
121   aatttattgc ttggttggtt aaaggtaggg tacctgataa aactgtgaga tggt-
      gtgcag
```

```
                            -continued
ttaaataacg aaccaaccaa tttccatccc atggactatt ttgacactct acca-
cacgtc
>............GLP-1............>>
  e  f  i  a  w  l  v  k  g  r
                                >>............mTf'.(SEQ ID NO:
53)>
                                   v  p  d  k  t  v  r-
   w  c  a
```

Top strand: SEQ ID NO: 50
Bottom strand: SEQ ID NO: 51
Top strand primer: P0056 (nucleotides 48–153 of SEQ ID NO: 50)
Bottom strand primer: P0057 (nucleotides 32–129 of SEQ ID NO: 51)

After annealing and ligation, the clones are sequenced to confirm correct insertion. This vector is designated pREX5028. The cassette is cut out of pREX5028 with PsiI/AgeI and sub-cloned into PsiI/AgeI cut yeast vector, such as PSAC3, to make the pREX5030.

pREX5030 is transformed into SMD1168 (his, pep4) and mut⁺ and mutˢ clones selected. Stocks were made at 10 OD/mL:

Y0023=SMD1168 pREX5030 mut⁺
Y0024=SMD1168 pREX5030 mutˢ

Example 4

β-IFN/Transferrin Protein

β-IFN is effective in the treatment of various diseases such as but not limited to multiple sclerosis, brain tumor, skin cancer, and hepatitis B and C. Like most cytokines, β-IFN has a short circulation half-life. The present invention provides fusion proteins comprising β-IFN fused to mTf with increased half-life and efficacy in patients. This example describes the steps in generating β-IFN/mTf fusion protein.

In this example, IFNβ-1 is fused to modified transferrin at both the N- and C-termini. The IFNβ-1 clone is obtained from ATCC (no. 39517). Specifically designed primers are used to confirm the DNA sequence of the IFNβ-1 clone.

These primers are external to the IFNβ-1 DNA sequence and designed to read in from the vector such that the full sequence of the clone were obtained. The primers used are:

P0070  GCTATGACCAACAAGTGTCTC       (SEQ ID NO: 54)

P0071  CGCACCTGTGGCGCCGGTGATG      (SEQ ID NO: 55)

N-terminal Fusion

Once the DNA sequence is confirmed, primers are designed for fusion of IFNβ-1 to mTf. The N-terminal fusion is a two step process. A straight fusion using primers with XbaI and KpnI sites would destroy the KpnI site and clip the beginning of mTf. A linker, primers P0082 (nucleotides 18–48 of SEQ ID NO: 56) and P0083 (nucleotides 17–39 SEQ ID NO: 57), is designed to create an internal KpnI site in the 3' of IFNβ-1, by a single silent mutation of bp 486 from T to G (bold), and with a 5' XbaI overhang and 3' GTAC which would anneal with a KpnI site. The overhang destroys the existing KpnI site in pREX5004. The linkers are annealed and ligated into pREX5004 cut with XbaI/KpnI creating an intermediate vector with mTf untouched and a KpnI site that could be used to fuse the IFNβ-1 gene at the N-terminus of mTf.

```
             XbaI              KpnI
             -+-----           -----+
             >>............P0082................>>
aagaagaagg ggtatctcta gagaaaacag g gtacctccg aaacgtacct gataaaactg
ttcttcttcc ccatagagat ctcttttgtc c catggaggc tttgcatgga ctattttgac <<........P0083.........<<
>>.........MFa-1...........>>
  e  e  g  v  s  l   e  k   (SEQ ID NO: 58)

>>....IFN-B-1.....>>
                                       t   g  y  l   r  n  (SEQ ID NO: 59)

>>......mTf........>
                                                       v  p   d  k  t
                                                       (SEQ ID NO: 60)
```

Top Strand: SEQ ID NO: 56
Bottom Strand: SEQ ID NO: 57

A second set of primers, P0084 (SEQ ID NO: 61) and P0085 (SEQ ID NO: 62), are designed to tailor the ends of the IFNβ-1 gene by mutagenic PCR for subsequent insertion into the intermediate vector via the XbaI and KpnI sites. A XbaI/KpnI digest of this tailored gene removes the last 5 amino acids of IFNβ-1; however, these are already engineered into the intermediate vector. The resulting construct, pREX5048, is created by ligating the IFNβ-1 gene cut with XbaI/KpnI into the XbaI/KpnI cut intermediate vector.

```
P0084 (SEQ ID NO: 61)
>>------MFa-1-------->>
                          >>----IFNβ-1-------->>
                                    XbaI
AGGGGTATC TCTAGA GAAAAGG AGCTACAACTTGCTTGGATT C

P0085 (SEQ ID NO: 62)
<<--------IFNβ-1-------<<
            KpnI
GTTTCGGA GGTACC CTGTAAGTCTG
```

After the pREX5048 construct was created, it was sequenced to confirm correct insertion. The expression cassette, as a PsiI/AgeI fragment, was then sub-cloned into PsiI/AgeI cut yeast vector, pSAC3, to make the pREX5050.

C-terminal Fusion

Specifically designed primers, P0086 (SEQ ID NO: 63) and P0087 (SEQ ID NO: 64), are used to PCR amplify the original clone and in addition tailor the ends of IFNβ-1 to have SalI and HindIII sites at the 5' and 3' ends respectively. The newly tailored product is ligated into SalI/HindIII cut pREX5004 to create pREX5049.

```
P0086                                    (SEQ ID NO: 63)
>>----MtF---->>
              >>------IFNβ-1-------->>
      SalI
ACTTTCC GTCGAC CT AGCTACAACTTGCTTGGATC

P0087                                    (SEQ ID NO: 64)
<<----3'AOX1t-------<<  *  *
                              <<-----IFNβ-1-------<<
                    HindIII
GAGGAACAGTCATGTCT AAGCTT TATTA

GTTTCGGAGGTAACCTGTAAGT
```

After the pREX5049 construct is created, it is sequenced to confirm correct insertion. The expression cassette, as a PsiI/AgeI fragment, is then sub-cloned into PsiI/AgeI cut yeast vector, such as pSAC3, to make pREX5051.

In one embodiment of the invention, β-IFN-1 (GenBank Acc. 002176) is made more stable and soluble by mutating Cys 17 into Ser. The mutation of Cys 17 into Ser can be performed by routine mutagenic reactions such as a mutagenic PCR reaction using specifically designed primers and the nucleic acid encoding β-IFN-1 as the template.

Further, the β-IFN-1 is modified to prevent glycosylation by modifying the N-linked glycosylation site, NXS/T. As an example, N could be mutagenized to Q and S/T could be mutagenized to Ala or other amino acid acids. Such mutagenesis could be performed with mutagenic PCR reaction using specifically designed primers and the nucleic acid encoding β-IFN-1 as the template.

Example 5

Soluble Toxin Receptor/Transferrin Protein

Clostridial neurotoxins are poisonous substance. Synaptotagmin I is a broad acting receptor of *Clostridium botulinum* neurotoxin serotypes. Amino acids 1–53 (SEQ ID NO: 4) of synaptotagmin I is responsible for binding to various neurotoxin serotypes. Like other peptides, a soluble toxin receptor, such as amino acids 1–53, has a short half-life. The present invention provides fusion protein comprising amino acids 1–53 fused mTf with increased half-life as compared to the soluble toxin receptor having SEQ ID NO: 1–53.

The present invention provides fusion proteins with antitoxin activity and increased half-life. Specifically, in this example, a fusion protein comprising modified Tf and a peptide consisting of amino acids 1–53 (SEQ ID NO: 4) of synaptotagmin I, is produced by fusing one or more copies of the nucleotide sequence encoding the peptide to the necleotide sequence of Tf to produce a fusion protein with a peptide fused to the N- or C-terminus of Tf.

To insert the sequence encoding SEQ ID NO: 4, the vector pREX5010 with the modified transferrin cDNA, is digested with the restriction enzymes Xba I/KpnI for insertion at the 5' end and Sal I/Hind III for insertion at the 3' end.

For the 5' insertion, two overlapping oligos that form an Xba I overhang at the 5' end and a Kpn I overhang at the 3' end of the nucleic acid encoding SEQ ID NO: 4 are synthesized. These oligos are then annealed together and ligated into the Xba I/Kpn I digested pREX5010 vector.

Transformation, selection, and expression are then performed in yeast.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

I claim:

1. A fusion protein comprising a transferrin (Tf) protein fused to a glucagon-like peptide-1 (GLP-1).

2. The fusion protein of claim 1, wherein the serum half-life of the GLP-1 peptide is increased over the serum half-life of a GLP-1 peptide in an unfused state.

3. The fusion protein of claim 1, wherein the GLP-1 peptide is GLP-1(7–36) or GLP-1(7–37).

4. The fusion protein of claim 3, wherein the GLP-1 peptide is GLP-1(7–37) consisting of SEQ ID NO: 6 or is GLP-1(7–36) consisting of amino acids 1–30 of SEQ ID NO: 6.

5. The fusion protein of claim 4, wherein the GLP-1 peptide has been modified by mutating Ala at position 2 in SEQ ID NO: 6.

6. The fusion protein of claim 5, wherein Ala at position 2 in SEQ ID NO: 6 has been mutated to Gly, Ser, or Val.

7. The fusion protein of claim 4, wherein the GLP-1 peptide has been modified by mutating Lys at position 28 in SEQ ID NO: 6.

8. The fusion protein of claim 7, wherein Lys at position 28 in SEQ ID NO: 6 has been mutated to Ala, Asn, or Gln.

9. The fusion protein of claim 4, wherein the GLP-1 peptide has been modified by mutating Ala at position 2 in SEQ ID NO: 6 to Gly and Lys at position 28 in SEQ ID NO: 6 to Ala.

10. The fusion protein of claim 1, wherein the GLP-1 peptide consists of the sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 6).

11. The fusion protein of claim 1, wherein GLP-1 has been modified to prevent dipeptidyl peptidase cleavage.

12. The fusion protein of claim 11, wherein GLP-1 has been modified at the N-terminus.

13. The fusion protein of claim 12, wherein GLP-1 has been chemically modified at the N-terminus.

14. The fusion protein of claim 13, wherein the His at the N-terminus of GLP-1 has been chemically modified.

15. The fusion protein of claim 1, wherein the GLP-1 peptide is fused to the N-terminal end of the Tf protein.

16. The fusion protein of claim 1, wherein the transferrin (Tf) protein exhibits reduced glycosylation as compared to a fully glycosylated Tf protein.

17. The fusion protein of claim 16, wherein the Tf protein comprises at least one mutation that prevents glycosylation.

18. The fusion protein of claim 17, wherein the mutation is in an N-linked glycosylation site comprising the sequence N-X-S/T.

19. The fusion protein of claim 18, wherein the Tf protein has been modified to have no affinity for iron.

20. The fusion protein of claim 18, wherein the sequence N-X-S/T sequence begins at an amino acid corresponding to N413 or N611 of SEQ ID NO: 3.

21. The fusion protein of claim 20, wherein N, X, S, or T has been changed to a proline.

22. The fusion protein of claim 1, wherein the Tf protein has been modified to exhibit no glycosylation.

23. The fusion protein of claim 1, wherein the Tf protein has been further modified to have reduced affinity for a transferrin receptor (TfR) as compared to a wild-type Tf protein.

24. The fusion protein of claim 23, wherein the Tf protein has been modified to have no binding for a TfR.

25. The fusion protein of claim 1, wherein the Tf protein has been further modified to have reduced affinity for iron as compared to a wild-type Tf protein.

26. The fusion protein of claim 1, wherein the fusion protein further comprises a linker.

27. The fusion protein of claim 26, wherein the linker links the GLP-1 peptide to the Tf protein.

28. The fusion protein of claim 1, wherein the Tf protein comprises a portion of the N domain of a Tf protein, a bridging peptide, and a portion of the C domain of a Tf protein.

29. The fusion protein of claim 1, wherein the Tf protein is a human protein.

30. The fusion protein of claim 29, wherein the Tf protein comprises SEQ ID NO: 3.

31. A modified Tf fusion protein comprising a Tf protein exhibiting reduced N-linked glycosylation fused at its N-terminus to a GLP-1 moiety comprising the sequence: His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Ala-Gly-Arg-Gly (SEQ ID NO: 67).

32. A pharmaceutical composition comprising the fusion protein of any one of claims 1–31 and a carrier.

33. A fusion protein comprising a GLP-1 peptide fused at its C-terminus to the N-terminus of a Tf protein which exhibits reduced N-linked glycosylation as compared to a fully N-linked glycosylated Tf protein, wherein the serum half-life of the GLP-1 peptide is increased compared to the serum half-life of a GLP-1 peptide in an unfused state.

34. A fusion protein of claim 33, wherein the Tf protein lacks N-linked glycosylation.

35. A composition comprising a fusion protein of claim 33 or 34.

36. A composition of claim 35, wherein the composition is a pharmaceutical composition.

37. A fusion protein comprising lactoferrin or melanotransferrin protein fused to a glucagon-like peptide-1 (GLP-1).

38. A method of treating a disease or condition treatable by GLP-1 in a subject comprising administering to said subject a therapeutically effective amount of a fusion protein of claim 1.

39. The method of claim 38, wherein the disease is a metabolic disease.

40. The method of claim 39, wherein the metabolic disease is diabetes or obesity.

41. The method of claim 40, wherein the diabetes is type II diabetes.

42. The method of claim 38, wherein the disease is congestive heart failure.

43. The method of claim 38, wherein the disease is inflammatory bowel syndrome disease.

44. The method of claim 38, wherein the subject is suffering from elevated level of glucose as compared to a healthy subject.

45. A method of claim 38, wherein the elevated level of glucose is associated with diabetes.

46. A method of claim 45, wherein the diabetes is Type II diabetes.

47. A method of regulating glucose levels in a subject comprising administering to the subject a therapeutically effective amount of a fusion protein of claim 1.

* * * * *

SEQUENCE LISTING

```
<160> NUMBER OF SEQ ID NOS: 66
<210> SEQ ID NO 1
<211> LENGTH: 2318
<212> TYPE: DNA
<213> ORGANISM: Homo sapiens
<220> FEATURE:
<221> NAME/KEY: CDS
<222> LOCATION: (51)..(2147)
<223> OTHER INFORMATION: GenBank Acc. No. NM_001063, transferrin gene
      and protein
<220> FEATURE:
```

-continued

```
<221> NAME/KEY: sig_peptide
<222> LOCATION: (51)..(107)

<400> SEQUENCE: 1
gcacagaagc gagtccgact gtgctcgctg ctcagcgccg cacccggaag atg agg         56
                                                        Met Arg
                                                        1 ctc gcc gtg gga gcc ctg ctg gtc tgc gcc gtc ctg ggg ctg tgt ctg      104
Leu Ala Val Gly Ala Leu Leu Val Cys Ala Val Leu Gly Leu Cys Leu
        5                   10                  15 gct gtc cct gat aaa act gtg aga tgg tgt gca gtg tcg gag cat gag      152
Ala Val Pro Asp Lys Thr Val Arg Trp Cys Ala Val Ser Glu His Glu
 20                  25                  30 gcc act aag tgc cag agt ttc cgc gac cat atg aaa agc gtc att cca      200
Ala Thr Lys Cys Gln Ser Phe Arg Asp His Met Lys Ser Val Ile Pro
35                  40                  45                  50 tcc gat ggt ccc agt gtt gct tgt gtg aag aaa gcc tcc tac ctt gat      248
Ser Asp Gly Pro Ser Val Ala Cys Val Lys Lys Ala Ser Tyr Leu Asp
                55                  60                  65 tgc atc agg gcc att gcg gca aac gaa gcg gat gct gtg aca ctg gat      296
Cys Ile Arg Ala Ile Ala Ala Asn Glu Ala Asp Ala Val Thr Leu Asp
            70                  75                  80 gca ggt ttg gtg tat gat gct tac ctg gct ccc aat aac ctg aag cct      344
Ala Gly Leu Val Tyr Asp Ala Tyr Leu Ala Pro Asn Asn Leu Lys Pro
        85                  90                  95 gtg gtg gca gag ttc tat ggg tca aaa gag gat cca cag act ttc tat      392
Val Val Ala Glu Phe Tyr Gly Ser Lys Glu Asp Pro Gln Thr Phe Tyr
    100                 105                 110 tat gct gtt gct gtg gtg aag aag gat agt ggc ttc cag atg aac cag      440
Tyr Ala Val Ala Val Val Lys Lys Asp Ser Gly Phe Gln Met Asn Gln
115                 120                 125                 130 ctt cga ggc aag aag tcc tgc cac acg ggt cta ggc agg tcc gct ggg      488
Leu Arg Gly Lys Lys Ser Cys His Thr Gly Leu Gly Arg Ser Ala Gly
                135                 140                 145 tgg aac atc ccc ata ggc tta ctt tac tgt gac tta cct gag cca cgt      536
Trp Asn Ile Pro Ile Gly Leu Leu Tyr Cys Asp Leu Pro Glu Pro Arg
            150                 155                 160 aaa cct ctt gag aaa gca gtg gcc aat ttc ttc tcg ggc agc tgt gcc      584
Lys Pro Leu Glu Lys Ala Val Ala Asn Phe Phe Ser Gly Ser Cys Ala
        165                 170                 175 cct tgt gcg gat ggg acg gac ttc ccc cag ctg tgt caa ctg tgt cca      632
Pro Cys Ala Asp Gly Thr Asp Phe Pro Gln Leu Cys Gln Leu Cys Pro
    180                 185                 190 ggg tgt ggc tgc tcc acc ctt aac caa tac ttc ggc tac tcg gga gcc      680
Gly Cys Gly Cys Ser Thr Leu Asn Gln Tyr Phe Gly Tyr Ser Gly Ala
195                 200                 205                 210 ttc aag tgt ctg aag gat ggt gct ggg gat gtg gcc ttt gtc aag cac      728
Phe Lys Cys Leu Lys Asp Gly Ala Gly Asp Val Ala Phe Val Lys His
                215                 220                 225 tcg act ata ttt gag aac ttg gca aac aag gct gac agg gac cag tat      776
Ser Thr Ile Phe Glu Asn Leu Ala Asn Lys Ala Asp Arg Asp Gln Tyr
            230                 235                 240 gag ctg ctt tgc ctg gac aac acc cgg aag ccg gta gat gaa tac aag      824
Glu Leu Leu Cys Leu Asp Asn Thr Arg Lys Pro Val Asp Glu Tyr Lys
        245                 250                 255 gac tgc cac ttg gcc cag gtc cct tct cat acc gtc gtg gcc cga agt      872
Asp Cys His Leu Ala Gln Val Pro Ser His Thr Val Val Ala Arg Ser
    260                 265                 270 atg ggc ggc aag gag gac ttg atc tgg gag ctt ctc aac cag gcc cag      920
Met Gly Gly Lys Glu Asp Leu Ile Trp Glu Leu Leu Asn Gln Ala Gln
```

```
                    -continued
      275           280           285           290 gaa cat ttt ggc aaa gac aaa tca aaa gaa ttc caa cta ttc agc tct    968
Glu His Phe Gly Lys Asp Lys Ser Lys Glu Phe Gln Leu Phe Ser Ser
                295               300               305 cct cat ggg aag gac ctg ctg ttt aag gac tct gcc cac ggg ttt tta   1016
Pro His Gly Lys Asp Leu Leu Phe Lys Asp Ser Ala His Gly Phe Leu
            310               315               320 aaa gtc ccc ccc agg atg gat gcc aag atg tac ctg ggc tat gag tat   1064
Lys Val Pro Pro Arg Met Asp Ala Lys Met Tyr Leu Gly Tyr Glu Tyr
        325               330               335 gtc act gcc atc cgg aat cta cgg gaa ggc aca tgc cca gaa gcc cca   1112
Val Thr Ala Ile Arg Asn Leu Arg Glu Gly Thr Cys Pro Glu Ala Pro
    340               345               350 aca gat gaa tgc aag cct gtg aag tgg tgt gcg ctg agc cac cac gag   1160
Thr Asp Glu Cys Lys Pro Val Lys Trp Cys Ala Leu Ser His His Glu
355               360               365               370 agg ctc aag tgt gat gag tgg agt gtt aac agt gta ggg aaa ata gag   1208
Arg Leu Lys Cys Asp Glu Trp Ser Val Asn Ser Val Gly Lys Ile Glu
                375               380               385 tgt gta tca gca gag acc acc gaa gac tgc atc gcc aag atc atg aat   1256
Cys Val Ser Ala Glu Thr Thr Glu Asp Cys Ile Ala Lys Ile Met Asn
                390               395               400 gga gaa gct gat gcc atg agc ttg gat gga ggg ttt gtc tac ata gcg   1304
Gly Glu Ala Asp Ala Met Ser Leu Asp Gly Gly Phe Val Tyr Ile Ala
            405               410               415 ggc aag tgt ggt ctg gtg cct gtc ttg gca gaa aac tac aat aag agc   1352
Gly Lys Cys Gly Leu Val Pro Val Leu Ala Glu Asn Tyr Asn Lys Ser
        420               425               430 gat aat tgt gag gat aca cca gag gca ggg tat ttt gct gta gca gtg   1400
Asp Asn Cys Glu Asp Thr Pro Glu Ala Gly Tyr Phe Ala Val Ala Val
435               440               445               450 gtg aag aaa tca gct tct gac ctc acc tgg gac aat ctg aaa ggc aag   1448
Val Lys Lys Ser Ala Ser Asp Leu Thr Trp Asp Asn Leu Lys Gly Lys
                455               460               465 aag tcc tgc cat acg gca gtt ggc aga acc gct ggc tgg aac atc ccc   1496
Lys Ser Cys His Thr Ala Val Gly Arg Thr Ala Gly Trp Asn Ile Pro
                470               475               480 atg ggc ctg ctc tac aat aag atc aac cac tgc aga ttt gat gaa ttt   1544
Met Gly Leu Leu Tyr Asn Lys Ile Asn His Cys Arg Phe Asp Glu Phe
            485               490               495 ttc agt gaa ggt tgt gcc cct ggg tct aag aaa gac tcc agt ctc tgt   1592
Phe Ser Glu Gly Cys Ala Pro Gly Ser Lys Lys Asp Ser Ser Leu Cys
        500               505               510 aag ctg tgt atg ggc tca ggc cta aac ctg tgt gaa ccc aac aac aaa   1640
Lys Leu Cys Met Gly Ser Gly Leu Asn Leu Cys Glu Pro Asn Asn Lys
515               520               525               530 gag gga tac tac ggc tac aca ggc gct ttc agg tgt ctg gtt gag aag   1688
Glu Gly Tyr Tyr Gly Tyr Thr Gly Ala Phe Arg Cys Leu Val Glu Lys
                535               540               545 gga gat gtg gcc ttt gtg aaa cac cag act gtc cca cag aac act ggg   1736
Gly Asp Val Ala Phe Val Lys His Gln Thr Val Pro Gln Asn Thr Gly
            550               555               560 gga aaa aac cct gat cca tgg gct aag aat ctg aat gaa aaa gac tat   1784
Gly Lys Asn Pro Asp Pro Trp Ala Lys Asn Leu Asn Glu Lys Asp Tyr
        565               570               575 gag ttg ctg tgc ctt gat ggt acc agg aaa cct gtg gag gag tat gcg   1832
Glu Leu Leu Cys Leu Asp Gly Thr Arg Lys Pro Val Glu Glu Tyr Ala
580               585               590 aac tgc cac ctg gcc aga gcc ccg aat cac gct gtg gtc aca cgg aaa   1880
```

-continued

```
Asn Cys His Leu Ala Arg Ala Pro Asn His Ala Val Val Thr Arg Lys
595                 600                 605                 610 gat aag gaa gct tgc gtc cac aag ata tta cgt caa cag cag cac cta    1928
Asp Lys Glu Ala Cys Val His Lys Ile Leu Arg Gln Gln Gln His Leu
                615                 620                 625 ttt gga agc aac gta act gac tgc tcg ggc aac ttt tgt ttg ttc cgg    1976
Phe Gly Ser Asn Val Thr Asp Cys Ser Gly Asn Phe Cys Leu Phe Arg
            630                 635                 640 tcg gaa acc aag gac ctt ctg ttc aga gat gac aca gta tgt ttg gcc    2024
Ser Glu Thr Lys Asp Leu Leu Phe Arg Asp Asp Thr Val Cys Leu Ala
        645                 650                 655 aaa ctt cat gac aga aac aca tat gaa aaa tac tta gga gaa gaa tat    2072
Lys Leu His Asp Arg Asn Thr Tyr Glu Lys Tyr Leu Gly Glu Glu Tyr
    660                 665                 670 gtc aag gct gtt ggt aac ctg aga aaa tgc tcc acc tca tca ctc ctg    2120
Val Lys Ala Val Gly Asn Leu Arg Lys Cys Ser Thr Ser Ser Leu Leu
675                 680                 685                 690 gaa gcc tgc act ttc cgt aga cct taa aatctcagag gtagggctgc          2167
Glu Ala Cys Thr Phe Arg Arg Pro
                695 caccaaggtg aagatgggaa cgcagatgat ccatgagttt gccctggttt cactggccca  2227 agtggtttgt gctaaccacg tctgtcttca cagctctgtg ttgccatgtg tgctgaacaa  2287 aaaataaaaa ttattattga ttttatattt c                                 2318

<210> SEQ ID NO 2
<211> LENGTH: 698
<212> TYPE: PRT
<213> ORGANISM: Homo sapiens

<400> SEQUENCE: 2

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205
```

-continued

```
Gly Ala Phe Lys Cys Leu Lys Asp Gly Ala Gly Asp Val Ala Phe Val
    210                 215                 220
Lys His Ser Thr Ile Phe Glu Asn Leu Ala Asn Lys Ala Asp Arg Asp
225                 230                 235                 240
Gln Tyr Glu Leu Leu Cys Leu Asp Asn Thr Arg Lys Pro Val Asp Glu
                245                 250                 255
Tyr Lys Asp Cys His Leu Ala Gln Val Pro Ser His Thr Val Val Ala
            260                 265                 270
Arg Ser Met Gly Gly Lys Glu Asp Leu Ile Trp Glu Leu Leu Asn Gln
        275                 280                 285
Ala Gln Glu His Phe Gly Lys Asp Lys Ser Lys Glu Phe Gln Leu Phe
    290                 295                 300
Ser Ser Pro His Gly Lys Asp Leu Leu Phe Lys Asp Ser Ala His Gly
305                 310                 315                 320
Phe Leu Lys Val Pro Pro Arg Met Asp Ala Lys Met Tyr Leu Gly Tyr
                325                 330                 335
Glu Tyr Val Thr Ala Ile Arg Asn Leu Arg Glu Gly Thr Cys Pro Glu
            340                 345                 350
Ala Pro Thr Asp Glu Cys Lys Pro Val Lys Trp Cys Ala Leu Ser His
        355                 360                 365
His Glu Arg Leu Lys Cys Asp Glu Trp Ser Val Asn Ser Val Gly Lys
    370                 375                 380
Ile Glu Cys Val Ser Ala Glu Thr Thr Glu Asp Cys Ile Ala Lys Ile
385                 390                 395                 400
Met Asn Gly Glu Ala Asp Ala Met Ser Leu Asp Gly Gly Phe Val Tyr
                405                 410                 415
Ile Ala Gly Lys Cys Gly Leu Val Pro Val Leu Ala Glu Asn Tyr Asn
            420                 425                 430
Lys Ser Asp Asn Cys Glu Asp Thr Pro Glu Ala Gly Tyr Phe Ala Val
        435                 440                 445
Ala Val Val Lys Lys Ser Ala Ser Asp Leu Thr Trp Asp Asn Leu Lys
    450                 455                 460
Gly Lys Lys Ser Cys His Thr Ala Val Gly Arg Thr Ala Gly Trp Asn
465                 470                 475                 480
Ile Pro Met Gly Leu Leu Tyr Asn Lys Ile Asn His Cys Arg Phe Asp
                485                 490                 495
Glu Phe Phe Ser Glu Gly Cys Ala Pro Gly Ser Lys Lys Asp Ser Ser
            500                 505                 510
Leu Cys Lys Leu Cys Met Gly Ser Gly Leu Asn Leu Cys Glu Pro Asn
        515                 520                 525
Asn Lys Glu Gly Tyr Tyr Gly Tyr Thr Gly Ala Phe Arg Cys Leu Val
    530                 535                 540
Glu Lys Gly Asp Val Ala Phe Val Lys His Gln Thr Val Pro Gln Asn
545                 550                 555                 560
Thr Gly Gly Lys Asn Pro Asp Pro Trp Ala Lys Asn Leu Asn Glu Lys
                565                 570                 575
Asp Tyr Glu Leu Leu Cys Leu Asp Gly Thr Arg Lys Pro Val Glu Glu
            580                 585                 590
Tyr Ala Asn Cys His Leu Ala Arg Ala Pro Asn His Ala Val Val Thr
        595                 600                 605
Arg Lys Asp Lys Glu Ala Cys Val His Lys Ile Leu Arg Gln Gln Gln
    610                 615                 620
```

```
His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
            645                 650                 655

Leu Ala Lys Leu His Asp Arg Asn Thr Tyr Glu Lys Tyr Leu Gly Glu
        660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
690                 695

<210> SEQ ID NO 3
<211> LENGTH: 679
<212> TYPE: PRT
<213> ORGANISM: Homo sapiens
<220> FEATURE:
<221> NAME/KEY: MISC_FEATURE
<223> OTHER INFORMATION: Mature Transferrin Protein

<400> SEQUENCE: 3

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
            85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
            245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285
```

-continued

```
His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
        435                 440                 445

Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Thr Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr Ser Ser Leu Leu Glu
            660                 665                 670

Ala Cys Thr Phe Arg Arg Pro
        675

<210> SEQ ID NO 4
<211> LENGTH: 53
```

```
<212> TYPE: PRT
<213> ORGANISM: Homo sapiens
<220> FEATURE:
<221> NAME/KEY: misc_feature
<223> OTHER INFORMATION: Amino acids 1-53 of synaptotagmin I

<400> SEQUENCE: 4

Met Val Ser Glu Ser His His Glu Ala Leu Ala Ala Pro Pro Val Thr
 1               5                  10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys
    50

<210> SEQ ID NO 5
<211> LENGTH: 12
<212> TYPE: PRT
<213> ORGANISM: Artificial sequence
<220> FEATURE:
<223> OTHER INFORMATION: Neutrophil lactoferrin splice variant

<400> SEQUENCE: 5

Glu Asp Cys Ile Ala Leu Lys Gly Glu Ala Asp Ala
 1               5                  10

<210> SEQ ID NO 6
<211> LENGTH: 31
<212> TYPE: PRT
<213> ORGANISM: Homo sapiens
<220> FEATURE:
<221> NAME/KEY: MISC_FEATURE
<223> OTHER INFORMATION: Glucagon-Like Peptide
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (37)..(37)
<223> OTHER INFORMATION: Xaa can be Gly in GLP-1 or NH2 in GLP-2

<400> SEQUENCE: 6

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
            20                  25                  30

<210> SEQ ID NO 7
<211> LENGTH: 28
<212> TYPE: PRT
<213> ORGANISM: Artificial sequence
<220> FEATURE:
<223> OTHER INFORMATION: GLP-1 molecule having insulinotropic activity

<400> SEQUENCE: 7

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys
            20                  25

<210> SEQ ID NO 8
<211> LENGTH: 29
<212> TYPE: PRT
<213> ORGANISM: Artificial sequence
```

```
<220> FEATURE:
<223> OTHER INFORMATION: GLP-1 molecule having insulinotropic activity

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 9
<211> LENGTH: 29
<212> TYPE: PRT
<213> ORGANISM: Artificial sequence
<220> FEATURE:
<223> OTHER INFORMATION: GLP-1 analog
<220> FEATURE:
<221> NAME/KEY: MISC_FEATURE
<222> LOCATION: (1)..(1)
<223> OTHER INFORMATION: Xaa can be Ala, Gly, Val, Thr, Ile, or alpha
      -methyl-Ala
<220> FEATURE:
<221> NAME/KEY: MISC_FEATURE
<222> LOCATION: (14)..(14)
<223> OTHER INFORMATION: Xaa can be Glu, Gln, Ala, Thr, Ser, or Gly
<220> FEATURE:
<221> NAME/KEY: MISC_FEATURE
<222> LOCATION: (20)..(20)
<223> OTHER INFORMATION: Xaa can be Glu, Gln, Ala, Thr, Ser or Gly

<400> SEQUENCE: 9

Xaa Glu Gly Thr Phe Thr Ser Asp Val Ser Ser Tyr Leu Xaa Gly Gln
1               5                   10                  15

Ala Ala Lys Xaa Phe Ile Ala Trp Leu Val Lys Gly Arg
            20                  25

<210> SEQ ID NO 10
<211> LENGTH: 10
<212> TYPE: PRT
<213> ORGANISM: Artificial sequence
<220> FEATURE:
<223> OTHER INFORMATION: EPO domain

<400> SEQUENCE: 10

Cys Arg Ile Gly Pro Ile Thr Trp Val Cys
1               5                   10

<210> SEQ ID NO 11
<211> LENGTH: 20
<212> TYPE: PRT
<213> ORGANISM: Artificial sequence
<220> FEATURE:
<223> OTHER INFORMATION: EMP1 peptide

<400> SEQUENCE: 11

Gly Gly Thr Tyr Ser Cys His Phe Gly Pro Leu Thr Trp Val Cys Lys
1               5                   10                  15

Pro Gln Gly Gly
            20

<210> SEQ ID NO 12
<211> LENGTH: 13
<212> TYPE: PRT
<213> ORGANISM: Artificial sequence
<220> FEATURE:
<223> OTHER INFORMATION: EMP20 peptide

<400> SEQUENCE: 12
```

```
Tyr Ser Cys His Phe Gly Pro Leu Thr Trp Val Cys Lys
1               5                   10
```

<210> SEQ ID NO 13
<211> LENGTH: 47
<212> TYPE: PRT
<213> ORGANISM: Homo sapiens
<220> FEATURE:
<221> NAME/KEY: misc_feature
<223> OTHER INFORMATION: N1 subdomain of transferrin

<400> SEQUENCE: 13

```
Asp Lys Ser Lys Glu Phe Gln Leu Phe Ser Ser Pro His Gly Lys Asp
1               5                   10                  15

Leu Leu Phe Lys Asp Ser Ala His Gly Phe Leu Lys Val Pro Pro Arg
                20                  25                  30

Met Asp Ala Lys Met Tyr Leu Gly Tyr Glu Tyr Val Thr Ala Ile
            35                  40                  45
```

<210> SEQ ID NO 14
<211> LENGTH: 45
<212> TYPE: PRT
<213> ORGANISM: Homo sapiens
<220> FEATURE:
<221> NAME/KEY: misc_feature
<223> OTHER INFORMATION: N2 subdomain of Transferrin

<400> SEQUENCE: 14

```
Pro Glu Pro Arg Lys Pro Leu Glu Lys Ala Val Ala Asn Phe Phe Ser
1               5                   10                  15

Gly Ser Cys Ala Pro Cys Ala Asp Gly Thr Asp Phe Pro Gln Leu Cys
                20                  25                  30

Gln Leu Cys Pro Gly Cys Gly Cys Ser Thr Leu Asn Gln
            35                  40                  45
```

<210> SEQ ID NO 15
<211> LENGTH: 42
<212> TYPE: PRT
<213> ORGANISM: Homo sapiens
<220> FEATURE:
<221> NAME/KEY: misc_feature
<223> OTHER INFORMATION: C1 subdomain of transferrin

<400> SEQUENCE: 15

```
Asn His Cys Arg Phe Asp Glu Phe Phe Ser Glu Gly Cys Ala Pro Gly
1               5                   10                  15

Ser Lys Lys Asp Ser Ser Leu Cys Lys Leu Cys Met Gly Ser Gly Leu
                20                  25                  30

Asn Leu Cys Glu Pro Asn Asn Lys Glu Gly
            35                  40
```

<210> SEQ ID NO 16
<211> LENGTH: 49
<212> TYPE: PRT
<213> ORGANISM: Homo sapiens
<220> FEATURE:
<221> NAME/KEY: misc_feature
<223> OTHER INFORMATION: C2 subdomain of transferrin

<400> SEQUENCE: 16

```
Asn Val Thr Asp Cys Ser Gly Asn Phe Cys Leu Phe Arg Ser Glu Thr
1               5                   10                  15

Lys Asp Leu Leu Phe Arg Asp Asp Thr Val Cys Leu Ala Lys Leu His
                20                  25                  30
```

```
Asp Arg Asn Thr Tyr Glu Lys Tyr Leu Gly Glu Glu Tyr Val Lys Ala
        35                  40                  45

Val
```

<210> SEQ ID NO 17
<211> LENGTH: 36
<212> TYPE: PRT
<213> ORGANISM: Artificial sequence
<220> FEATURE:
<223> OTHER INFORMATION: DP-178 peptide from US 6,479,055

<400> SEQUENCE: 17

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

<210> SEQ ID NO 18
<211> LENGTH: 30
<212> TYPE: DNA
<213> ORGANISM: Artificial sequence
<220> FEATURE:
<223> OTHER INFORMATION: Primer P0038

<400> SEQUENCE: 18
ctagagaaaa ggtacactag cttaatacac                              30

<210> SEQ ID NO 19
<211> LENGTH: 46
<212> TYPE: DNA
<213> ORGANISM: Artificial sequence
<220> FEATURE:
<223> OTHER INFORMATION: Primer P0039

<400> SEQUENCE: 19
tgcgattctt caattaagga gtgtattaag ctagtgtacc ttttct            46

<210> SEQ ID NO 20
<211> LENGTH: 40
<212> TYPE: DNA
<213> ORGANISM: Artificial sequence
<220> FEATURE:
<223> OTHER INFORMATION: Primer P0040

<400> SEQUENCE: 20
tccttaattg aagaatcgca aaaccagcaa gaaaagaatg                   40

<210> SEQ ID NO 21
<211> LENGTH: 40
<212> TYPE: DNA
<213> ORGANISM: Artificial sequence
<220> FEATURE:
<223> OTHER INFORMATION: Primer P0041

<400> SEQUENCE: 21
taattccaat aattcttgtt cattcttttc ttgctggttt                   40

<210> SEQ ID NO 22
<211> LENGTH: 54
<212> TYPE: DNA
<213> ORGANISM: Artificial sequence
<220> FEATURE:

<223> OTHER INFORMATION: Primer P0042

<400> SEQUENCE: 22
aacaagaatt attggaatta gataaatggg caagtttgtg gaattggttt gtac                54

<210> SEQ ID NO 23
<211> LENGTH: 30
<212> TYPE: DNA
<213> ORGANISM: Artificial sequence
<220> FEATURE:
<223> OTHER INFORMATION: Primer P0043

<400> SEQUENCE: 23
aaaccaattc cacaaacttg cccatttatc                                          30

<210> SEQ ID NO 24
<211> LENGTH: 25
<212> TYPE: DNA
<213> ORGANISM: Artificial sequence
<220> FEATURE:
<223> OTHER INFORMATION: Primer P0044

<400> SEQUENCE: 24
tcgaccttac actagcttaa tacac                                               25

<210> SEQ ID NO 25
<211> LENGTH: 41
<212> TYPE: DNA
<213> ORGANISM: Artificial sequence
<220> FEATURE:
<223> OTHER INFORMATION: Primer P0045

<400> SEQUENCE: 25
tgcgattctt caattaagga gtgtattaag ctagtgtaag g                             41

<210> SEQ ID NO 26
<211> LENGTH: 40
<212> TYPE: DNA
<213> ORGANISM: Artificial sequence
<220> FEATURE:
<223> OTHER INFORMATION: Primer P0040

<400> SEQUENCE: 26
tccttaattg aagaatcgca aaaccagcaa gaaaagaatg                               40

<210> SEQ ID NO 27
<211> LENGTH: 40
<212> TYPE: DNA
<213> ORGANISM: Artificial sequence
<220> FEATURE:
<223> OTHER INFORMATION: Primer P0041

<400> SEQUENCE: 27
taattccaat aattcttgtt cattcttttc ttgctggttt                               40

<210> SEQ ID NO 28
<211> LENGTH: 55
<212> TYPE: DNA
<213> ORGANISM: Artificial sequence
<220> FEATURE:
<223> OTHER INFORMATION: Primer P0046

<400> SEQUENCE: 28
aacaagaatt attggaatta gataaatggg caagtttgtg gaattggttt taata             55

<210> SEQ ID NO 29
<211> LENGTH: 39
<212> TYPE: DNA
<213> ORGANISM: Artificial sequence
<220> FEATURE:
<223> OTHER INFORMATION: Primer P0047

<400> SEQUENCE: 29
agcttattaa aaccaattcc acaaacttgc ccatttatc         39

<210> SEQ ID NO 30
<211> LENGTH: 175
<212> TYPE: DNA
<213> ORGANISM: Artificial sequence
<220> FEATURE:
<223> OTHER INFORMATION: pREX0032 plasmid

<400> SEQUENCE: 30
caaggctgtt ggtaacctga gaaaatgctc cacctcatca ctcctggaag cctgcacttt         60
ctacactagc ttaatacact ccttaattga agaatcgcaa aaccagcaag aaaagaatga         120
acaagaatta ttggaattag ataaatgggc aagtttgtgg aattggtttt aataa         175

<210> SEQ ID NO 31
<211> LENGTH: 184
<212> TYPE: DNA
<213> ORGANISM: Artificial sequence
<220> FEATURE:
<223> OTHER INFORMATION: pREX0017 plasmid

<400> SEQUENCE: 31
caaggctgtt ggtaacctga gaaaatgctc cacctcatca ctcctggaag cctgcacttt         60
ccgtcgacct tacactagct taatacactc cttaattgaa gaatcgcaaa accagcaaga         120
aaagaatgaa caagaattat tggaattaga taaatgggca agtttgtgga attggttttta        180 ataa         184

<210> SEQ ID NO 32
<211> LENGTH: 50
<212> TYPE: DNA
<213> ORGANISM: Artificial sequence
<220> FEATURE:
<223> OTHER INFORMATION: Primer P0060

<400> SEQUENCE: 32
tcatcactcc tggaagcctg cactttctac actagcttaa tacactcctt         50

<210> SEQ ID NO 33
<211> LENGTH: 50
<212> TYPE: DNA
<213> ORGANISM: Artificial sequence
<220> FEATURE:
<223> OTHER INFORMATION: Primer P0061

<400> SEQUENCE: 33
aaggagtgta ttaagctagt gtagaaagtg caggcttcca ggagtgatga         50

<210> SEQ ID NO 34
<211> LENGTH: 41
<212> TYPE: DNA
<213> ORGANISM: Artificial sequence
<220> FEATURE:
<223> OTHER INFORMATION: Primer P0064

<400> SEQUENCE: 34

```
ttgtctacat agcgggcaag ggtggtctgg tgcctgtctt g         41

<210> SEQ ID NO 35
<211> LENGTH: 41
<212> TYPE: DNA
<213> ORGANISM: Artificial sequence
<220> FEATURE:
<223> OTHER INFORMATION: Primer P0065

<400> SEQUENCE: 35
caagacaggc accagaccac ccttgcccgc tatgtagaca a         41

<210> SEQ ID NO 36
<211> LENGTH: 45
<212> TYPE: DNA
<213> ORGANISM: Artificial sequence
<220> FEATURE:
<223> OTHER INFORMATION: Primer P0068

<400> SEQUENCE: 36
tccacctcat cactcctgga agccggtact ttccgtcgac cttaa     45

<210> SEQ ID NO 37
<211> LENGTH: 48
<212> TYPE: DNA
<213> ORGANISM: Artificial sequence
<220> FEATURE:
<223> OTHER INFORMATION: Primer P0069

<400> SEQUENCE: 37
cttattaagg tcgacggaaa gtaccggctt ccaggagtga tgaggtgg  48

<210> SEQ ID NO 38
<211> LENGTH: 50
<212> TYPE: DNA
<213> ORGANISM: Artificial sequence
<220> FEATURE:
<223> OTHER INFORMATION: pREX0017 plasmid starting at 1501

<400> SEQUENCE: 38
tagcgggcaa gtgtggtctg gtgcctgtct tggcagaaaa ctacaataag  50

<210> SEQ ID NO 39
<211> LENGTH: 50
<212> TYPE: DNA
<213> ORGANISM: Artificial sequence
<220> FEATURE:
<223> OTHER INFORMATION: pREX0034 plasmid starting at 1501

<400> SEQUENCE: 39
tagcgggcaa gggtggtctg gtgcctgtct tggcagaaaa ctacaataag  50

<210> SEQ ID NO 40
<211> LENGTH: 50
<212> TYPE: DNA
<213> ORGANISM: Artificial sequence
<220> FEATURE:
<223> OTHER INFORMATION: pREX0017 plasmid starting at 2301

<400> SEQUENCE: 40
tgctccacct catcactcct ggaagcctgc actttccgtc gaccttacac  50

<210> SEQ ID NO 41
<211> LENGTH: 50
<212> TYPE: DNA
<213> ORGANISM: Artificial sequence
```

```
<220> FEATURE:
<223> OTHER INFORMATION: pREX0034 plasmid starting at 2301

<400> SEQUENCE: 41
tgctccacct catcactcct ggaagccggt actttccgtc gaccttacac                50

<210> SEQ ID NO 42
<211> LENGTH: 48
<212> TYPE: DNA
<213> ORGANISM: Artificial sequence
<220> FEATURE:
<223> OTHER INFORMATION: Primer P0066

<400> SEQUENCE: 42
tccacctcat cactcctgga agccggcact ttctacacta gcttaata               48

<210> SEQ ID NO 43
<211> LENGTH: 48
<212> TYPE: DNA
<213> ORGANISM: Artificial sequence
<220> FEATURE:
<223> OTHER INFORMATION: Primer P0067

<400> SEQUENCE: 43
gtgtattaag ctagtgtaga aagtaccggc ttccaggagt gatgaggt                48

<210> SEQ ID NO 44
<211> LENGTH: 41
<212> TYPE: DNA
<213> ORGANISM: Artificial sequence
<220> FEATURE:
<223> OTHER INFORMATION: pREX0033 plasmid starting at 2301

<400> SEQUENCE: 44
tgctccacct catcactcct ggaagccggt actttctaca c                       41

<210> SEQ ID NO 45
<211> LENGTH: 60
<212> TYPE: DNA
<213> ORGANISM: Artificial sequence
<220> FEATURE:
<223> OTHER INFORMATION: synthetic oligonucleotide encoding peptide with
      EPO activity

<400> SEQUENCE: 45
ggtggtactt actcttgtca ttttggtcca ttgacttggg tttgtaagcc acaaggtggt   60

<210> SEQ ID NO 46
<211> LENGTH: 140
<212> TYPE: DNA
<213> ORGANISM: Artificial sequence
<220> FEATURE:
<223> OTHER INFORMATION: His289-Gly290 insert PCR product

<400> SEQUENCE: 46
agacaaatca aaagaatttc aactattcag ctctcctcat ggtggtactt actcttgtca   60
ttttggtcca ttgacttggg tttgtaagcc acaaggtggt gggaaggacc tgctgtttaa  120
ggactctgcc cacgggtttt                                              140

<210> SEQ ID NO 47
<211> LENGTH: 210
<212> TYPE: DNA
<213> ORGANISM: Artificial sequence
<220> FEATURE:
<223> OTHER INFORMATION: Glu625-Thr626 insert PCR product
```

<400> SEQUENCE: 47

```
cctatttgga agcaacgtaa ctgactgctc gggcaacttt tgtttgttcc ggtcggaagg      60
tggtacttac tcttgtcatt tggtccatt gacttgggtt tgtaagccac aaggtggtac     120
caaggacctt ctgttcagag atgacacagt atgtttggcc aaacttcatg acagaaacac    180
atatgaaaaa tacttaggag aagaatatgt                                     210
```

<210> SEQ ID NO 48
<211> LENGTH: 30
<212> TYPE: PRT
<213> ORGANISM: Artificial sequence
<220> FEATURE:
<223> OTHER INFORMATION: glucagon-like peptide-1

<400> SEQUENCE: 48

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 49
<211> LENGTH: 90
<212> TYPE: DNA
<213> ORGANISM: Artificial sequence
<220> FEATURE:
<223> OTHER INFORMATION: sequence encoding glucagon-like peptide-1

<400> SEQUENCE: 49

```
catgctgaag gtactttac ttctgatgtt tcttcttatt tggaaggtca agctgctaaa      60
gaatttattg cttggttggt taaaggtaga                                     90
```

<210> SEQ ID NO 50
<211> LENGTH: 180
<212> TYPE: DNA
<213> ORGANISM: Artificial sequence
<220> FEATURE:
<223> OTHER INFORMATION: Top Strand Synthetic Oligonucleotide
<220> FEATURE:
<221> NAME/KEY: misc_feature
<222> LOCATION: (48)..(153)
<223> OTHER INFORMATION: Top Strand Primer P0056

<400> SEQUENCE: 50

```
taaatactac tattgccagc attgctgcta aagaagaagg ggtatctcta gagaaaaggc      60
atgctgaagg tactttact tctgatgttt cttcttattt ggaaggtcaa gctgctaaag    120
aatttattgc ttggttggtt aaaggtaggg tacctgataa aactgtgaga tggtgtgcag    180
```

<210> SEQ ID NO 51
<211> LENGTH: 180
<212> TYPE: DNA
<213> ORGANISM: Artificial sequence
<220> FEATURE:
<223> OTHER INFORMATION: Bottom Strand Synthetic Oligonucleotide
<220> FEATURE:
<221> NAME/KEY: misc_feature
<222> LOCATION: (32)..(129)
<223> OTHER INFORMATION: Bottom Strand Primer P0057

<400> SEQUENCE: 51

```
ctgcacacca tctcacagtt ttatcaggta ccctaccttt aaccaaccaa gcaataaatt      60
ctttagcagc ttgaccttcc aaataagaag aaacatcaga agtaaaagta ccttcagcat    120
```

```
gccttttctc tagagatacc ccttcttctt tagcagcaat gctggcaata gtagtattta    180
```

<210> SEQ ID NO 52
<211> LENGTH: 19
<212> TYPE: PRT
<213> ORGANISM: Artificial sequence
<220> FEATURE:
<223> OTHER INFORMATION: 'MFa-1 peptide sequence

<400> SEQUENCE: 52

Asn Thr Thr Ile Ala Ser Ile Ala Ala Lys Glu Glu Gly Val Ser Leu
1               5                   10                  15

Glu Lys Arg

<210> SEQ ID NO 53
<211> LENGTH: 10
<212> TYPE: PRT
<213> ORGANISM: Artificial sequence
<220> FEATURE:
<223> OTHER INFORMATION: mTf' peptide sequence

<400> SEQUENCE: 53

Val Pro Asp Lys Thr Val Arg Trp Cys Ala
1               5                   10

<210> SEQ ID NO 54
<211> LENGTH: 21
<212> TYPE: DNA
<213> ORGANISM: Artificial sequence
<220> FEATURE:
<223> OTHER INFORMATION: Primer P0070

<400> SEQUENCE: 54

```
gctatgacca acaagtgtct c                                              21
```

<210> SEQ ID NO 55
<211> LENGTH: 22
<212> TYPE: DNA
<213> ORGANISM: Artificial sequence
<220> FEATURE:
<223> OTHER INFORMATION: Primer P0071

<400> SEQUENCE: 55

```
cgcacctgtg gcgccggtga tg                                             22
```

<210> SEQ ID NO 56
<211> LENGTH: 60
<212> TYPE: DNA
<213> ORGANISM: Artificial sequence
<220> FEATURE:
<223> OTHER INFORMATION: Sequence for fusion of IFN Beta-1 to mTf
<220> FEATURE:
<221> NAME/KEY: misc_feature
<222> LOCATION: (18)

```
<222> LOCATION: (17)..(39)
<223> OTHER INFORMATION: Primer P0083 sequence

<400> SEQUENCE: 57
cagttttatc aggtacgttt cggaggtacc ctgttttctc tagagatacc ccttcttctt      60

<210> SEQ ID NO 58
<211> LENGTH: 8
<212> TYPE: PRT
<213> ORGANISM: Artificial sequence
<220> FEATURE:
<223> OTHER INFORMATION: MFa-1 sequence

<400> SEQUENCE: 58

Glu Glu Gly Val Ser Leu Glu Lys
1               5

<210> SEQ ID NO 59
<211> LENGTH: 6
<212> TYPE: PRT
<213> ORGANISM: Artificial sequence
<220> FEATURE:
<223> OTHER INFORMATION: IFN-B-1 sequence

<400> SEQUENCE: 59

Thr Gly Tyr Leu Arg Asn
1               5

<210> SEQ ID NO 60
<211> LENGTH: 4
<212> TYPE: DNA
<213> ORGANISM: Artificial sequence
<220> FEATURE:
<223> OTHER INFORMATION: mTf sequence

<400> SEQUENCE: 60 vdkt                                                                   4

<210> SEQ ID NO 61
<211> LENGTH: 43
<212> TYPE: DNA
<213> ORGANISM: Artificial sequence
<220> FEATURE:
<223> OTHER INFORMATION: Primer P0084

<400> SEQUENCE: 61
aggggtatct ctagagaaaa ggagctacaa cttgcttgga ttc                        43

<210> SEQ ID NO 62
<211> LENGTH: 25
<212> TYPE: DNA
<213> ORGANISM: Artificial sequence
<220> FEATURE:
<223> OTHER INFORMATION: Primer P0085

<400> SEQUENCE: 62
gtctgaatgt cccatggagg ctttg                                            25

<210> SEQ ID NO 63
<211> LENGTH: 36
<212> TYPE: DNA
<213> ORGANISM: Artificial sequence
<220> FEATURE:
<223> OTHER INFORMATION: Primer P0086

<400> SEQUENCE: 63
```

```
actttccgtc gacctagcta caacttgctt ggattc                            36
```

<210> SEQ ID NO 64
<211> LENGTH: 50
<212> TYPE: DNA
<213> ORGANISM: Artificial sequence
<220> FEATURE:
<223> OTHER INFORMATION: Primer P0087

<400> SEQUENCE: 64

```
tgaatgtcca atggaggctt tgattatttc gaatctgtac tgacaaggag             50
```

<210> SEQ ID NO 65
<211> LENGTH: 3244
<212> TYPE: DNA
<213> ORGANISM: Homo sapiens
<220> FEATURE:
<221> NAME/KEY: misc_feature
<223> OTHER INFORMATION: Synaptotagmin
<220> FEATURE:
<221> NAME/KEY: misc_feature
<222> LOCATION: (669)..(674)
<223> OTHER INFORMATION: KpnI site

<400> SEQUENCE: 65

```
taatagaaca cttcacctga acctaaaatg gtgagcgaga gtcaccatga ggccctggca   60
gccccgcctg tcaccactgt cgcgactgtt ctgccaagca atgccacaga gccagccagt  120
cctggagaag gaaaggaaga tgcatttttct aagctgaagg agaagtttat gaatgagttg  180
cataaaattc cattgccacc gtgggcctta attgcaatag ccatagtcgc agtcctttta  240
gtcctgacct gctgctttttg tatctgtaag aaatgtttgt tcaaaagaa aaacaagaag  300
aagggaaagg aaaaggagg gaagaatgcc attaacatga aagatgtaaa agacttaggg  360
aagacgatga agatcaggc cctcaaggat gatgatgctg aaactggatt gacagatgga  420
gaagaaaaag aagaacccaa agaagaggag aaactgggaa aacttcagta ttcactggat  480
tatgatttcc aaaataacca gctgctggta gggatcattc aggctgctga actgcccgcc  540
ttggacatgg gggcacatc tgatccttac gtgaaagtgt ttctgctacc tgataagaag  600
aagaaatttg agacaaaagt ccaccgaaaa accttaatc ctgtcttcaa tgagcaattt  660
actttcaagg taccatactc ggaattgggt ggcaaaaccc tagtgatggc tgtatatgat  720
tttgatcgtt tctctaagca tgacatcatt ggagaattta agtccctat gaacacagtg  780
gattttggcc atgtaactga ggaatggcgt gacctgcaaa gtgctgagaa ggaagagcaa  840
gagaaattgg gtgatatctg cttctccctt cgctacgtac ctactgctgg taagctgact  900
gttgtcattc tggaggcaaa gaacctgaag aagatggatg tgggtggctt atccgatcct  960
tatgtgaaga ttcatctgat gcagaatggt aagaggctga agaagaaaaa gacaacaatt 1020
aaaaagaaca cacttaaccc ctactacaat gagtcattca gctttgaagt acctttttgaa 1080
caaatccaga aagtgcaggt ggtggtaact gttttttggact atgacaagat tggcaagaac 1140
gatgccatcg gcaaagtctt tgtgggctac aacagcaccg gcgcggagct gcgacactgg 1200
tcagacatgc tggccaaccc caggcgacct attgcccagt ggcacaccct gcaggtagag 1260
gaggaagttg atgccatgct ggccgtcaag aagtaaagga aagaagaagc ctttctgcat 1320
ttgcccatat agtgctcttt agccagtatc tgtaaatacc tcagtaatat gggtcctttc 1380
attttttccag ccatgcattc ctaacacaat tcagtggtac ttggaatcct gttttaattt 1440
gcacaaattt aaatgtagag agcccctaag tccttcatca taccactgcc ctccaaatct 1500
```

-continued

```
actcttcttt taagcaatat gatgtgtaga tagagcatga atgaaattat ttattgtatc    1560
acactgttgt ataccagt atgctaaaga tttatttcta gtttgtgtat ttgtatgttg    1620
taagcgtttc ctaatctgtg tatatctaga tgtttttaat aagatgttct attttaaact    1680
atgtaaattg actgagatat aggagagctg ataatatatt atacggtaaa tatagtatcg    1740
tctgcattcc agcaaaaata tcaactcgta aggcactagt acagttaaac tgacatctta    1800
aaggacaact taaacctgag ctttctattg aatcatttga gtaccaagat aaacttacac    1860
cacatacttg gtgggtgaat ccaattttgt agaattccta cacaggcaaa atagcatgat    1920
ctgagcagca gcatccaggc tgacctcaag gaagcatagc cacaaaacag aatagcacct    1980
gtctgtacat atttacaaag ctaaataat ggcttcactc ttatatttga ggaagcaact    2040
gaacaggagt caatgatttc atattactgc atatagaata caacaaggt gttccgtgtg    2100 tgtgtgtgtg tgtgtgtgtg tgtgtgtgtg tgtgtgtgtg cacatttgtt tggggatggg    2160
ggagaagaag ctaaggggag aagtcaacat ttatgaaata ttgcctgact atttaaaaag    2220
aaaaaagtag ctctccatta tcacctttat acaaaatgta catcctgtga attctgttcc    2280
agatttcaca cctacaataa ttccaaaagg tttgcacatt agagtttgta acaaaatatt    2340
ttattatata aaccaggtt agaaggaatg caggatattt ttaacacaac aatctgtgct    2400
tattacacaa aattactttg tggtaaacag acagtattgt aatcccatca aaagatgaaa    2460 gaaaacaaa aacaaaaacc aacaacaatt agccatagtt ctgaatgcac ttcaattaag    2520
ccaaaacaga cagctagtga tcttttttata tgctcttttt acttaagttt taatttgtcc    2580
tttaaaaaaa ggtgaaacaa accaagaaca agttctagaa aactgaagca acctcttatg    2640
tatactagat gcttgattta ggaggagttt taaacgtttt tcaatgttat tatgtagtaa    2700
atgacactat tatgaagcta ctagtcattc cataagagtc ttaaaggact gctctgtgta    2760
cactgtgact gccgtgtgtg cttagacccg tagtttcctc agtggatagc actcaattta    2820
ttccgtagtg atattgtaac aatactgcca ttcccttcta ctgcactgcc caaggtgtgt    2880
gtagcacaaa cagttctcat tacaaaggac caattcagaa ctgaaaagct atgcatagga    2940
caaggaagat acatagaatg gggtggaaca cagcattttg tcaagcactg tgcaatattc    3000 catattttc cccactatgg tagacaacca tttcgtggaa gggcagccta ttatcccaca    3060
ctgcatctag cctttgtcc cattcacttc tgtgatccat tttaatttcc aggccacaag    3120
acagtagtga tgctctgaaa tgaaagtttg tcttcacaaa tatcaaaaca aaatggagga    3180
aaactaagca ttggcctcat gttcagtctt caggatatca caccacgtct tttcaaaaac    3240
taaa                                                                 3244
```

<210> SEQ ID NO 66
<211> LENGTH: 31
<212> TYPE: PRT
<213> ORGANISM: Artificial sequence
<220> FEATURE:
<223> OTHER INFORMATION: GLP-1(7-37) amino acid sequence

<400> SEQUENCE: 66

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30
```